United States Patent [19]

Maiti et al.

[11] Patent Number: 5,264,429
[45] Date of Patent: Nov. 23, 1993

[54] 2-SPIROCYCLOPROPYL CEPHALOSPORIN SULFONE DERIVATIVES

[75] Inventors: Samarendra N. Maiti; David Czajkowski; Paul Spevak; Kazuo Adachi, all of Edmonton; Ronald G. Micetich, Sherwood Park, all of Canada

[73] Assignee: SynPhar Laboratories, Inc., Edmonton, Canada

[21] Appl. No.: 747,762

[22] Filed: Aug. 20, 1991

Related U.S. Application Data

[63] Continuation-in-part of Ser. No. 685,960, Apr. 8, 1991, which is a continuation-in-part of PCT/CA90/00343, Oct. 5, 1990, and a continuation-in-part of Ser. No. 418,075, Oct. 6, 1989, abandoned.

[51] Int. Cl.$^5$ .................. C07D 501/00; A61K 31/545
[52] U.S. Cl. ..................... 514/202; 514/201; 514/206; 540/222; 540/225; 540/226
[58] Field of Search ............... 540/225, 227, 226, 221; 514/202, 206

[56] References Cited

U.S. PATENT DOCUMENTS

| 3,883,517 | 5/1975 | Heusler et al. ............ 260/243 CX |
| 4,547,371 | 10/1985 | Doherty et al. ................. 514/200 |
| 4,717,722 | 1/1988 | Doherty et al. ................. 514/210 |

FOREIGN PATENT DOCUMENTS

| 80624/87 | 5/1988 | Australia . |
| 32762/89 | 10/1989 | Australia . |
| WO91/04977 | 4/1991 | Canada . |
| 0124081 | 11/1985 | European Pat. Off. . |
| 0267723 | 5/1988 | European Pat. Off. . |
| 0337704 | 10/1989 | European Pat. Off. . |
| 1-226887 | 11/1989 | Japan . |
| WO89/10926 | 11/1989 | PCT Int'l Appl. . |

OTHER PUBLICATIONS

Alpagiani et al., Bioorganic & Medicinal Chemistry Letters, vol. 2, No. 9, pp. 1127-1132, 1992.
Annual Drug Data Report, 10(11), 868 (1988).
Annual Drug Data Report, 11(6), 459 (1989).
Annual Drug Data Report, 12(10), 785 (1990).
Doherty et al, J. Med. Chem., 33, 2513-2521 (1990).
Finke et al, J. Med. Chem., 33, 2522-2528 (1990).
Shah et al, J. Med. Chem., 33, 2529-2535 (1990).
McClintock et al, J. Liquid Chromatography, 12 (15), 2961-296 (1989).
Annual Drug Data Report, 13(1), 24 (1991).
Annual Drug Data Report, 12(2), 116 (1990).
Annual Drug Data Report, 12(6), 458 (1990).
Doherty et al, Nature, 322, 192-194 (Jul. 10, 1986).
Pitlick et al, J. Heterocyclic Chem., 26, 461-464, (1989).
Hagmann et al, Eur. J. Med. Chem., 24 pp. 599-604 (1989).
Blacklock et al, J. Org. Chem., 54, pp. 3907-3913 (1989).
Wright et al, J. Med. Chem., 14, pp. 420-429 (1971).
Fletcher et al, Am. Rev. Resp. Disc., 141, pp. 672-677 (1990).
Gunda; Tamas E., Liebigs Ann. Chem., pp. 311-312 (1990).
Jaszberenyi et al, Magnetic Resonance in Chemistry, 26, pp. 658-664 (1988).
Bonney et al, J. Cell. Biochem., 39, pp. 47-53 (1989).
Annual Reports in Medicinal Chemistry, pp. 68-70 (1989).
Navia et al, Nature, 327, pp. 79-82 (1987).
Kaiser et al, J. Med. Chem., 14, 426-429 (1971).
Annual Drug Data Report, 7(4), 263 (1985).

Primary Examiner—Micholas S. Rizzo
Attorney, Agent, or Firm—Nikaido, Marmelstein, Murray & Oram

[57] ABSTRACT

Derivatives of 2-spirocyclopropyl cephalosporin sulfone of the structural formula I

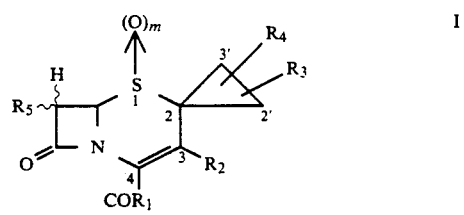

are provided which are useful as potent elastase inhibitors.

16 Claims, No Drawings

2-SPIROCYCLOPROPYL CEPHALOSPORIN SULFONE DERIVATIVES

This application is a continuation-in-part of application Ser. No. 07/685,960, filed Apr. 8, 1991, PCT International Application No. CA90/00343, filed Oct. 5, 1990, and Ser. No. 07/418,075, filed Oct. 6, 1989, now abandoned.

The present invention relates to novel 2-spirocyclopropyl cephalosporin sulfone derivatives and to processes for their preparation.

BACKGROUND OF THE INVENTION

Emphysema is an abnormal and irreversible enlargement of the air spaces around the bronchioles caused by chronic inflammation. It is also characterized by the destruction of the alveolar walls of the lungs. As the damage to the alveolar walls increases the lungs lose their elasticity. The progressive symptoms include shortness of breath upon minimal exertion, frequent respiratory infections and chronic cough. Emphysema is considered to be one of the chronic pulmonary diseases.

The hydrolytic action of the enzyme human leukocyte elastase (HLE) on the connective tissue component elastin is believed to be the cause of pulmonary emphysema. Like other serine proteases, elastase may be inactivated by inhibitors which block the active site of the enzyme by binding tightly thereto. Under normal conditions, these enzymes are prevented from causing damage by the action of the natural inhibitor $\alpha_1$-antitrypsin, which is a glycoprotein present in human serum.

It would appear that the inflammation caused by cigarette smoke provokes the release of a large amount of leukocyte elastase and hence an imbalance between the two enzymes results. The quantity of $\alpha_1$-antitrypsin present is thus insufficient to inhibit enough of the leukocyte elastase. Consequently the excess elastase begins adhering to the surfaces of elastin fibers in the lungs. This eventually leads to the lung damage characteristic of emphysema.

Additionally, it is believed that the action of cigarette smoke functions to inactivate the $\alpha_1$-antitrypsin. Also an $\alpha_1$-antitrypsin deficiency may be caused by hereditary factors.

Cephalosporin drugs are widely used for the treatment and prevention of various infectious diseases caused by pathogenic bacteria.

U.S. Pat. No. 4,547,371, discloses that certain substituted cephalosporin sulfones demonstrate potent elastase inhibitory effects. U.S. Pat. No. 4,711,886, describes β-lactam derivatives which are found to be potent elastase inhibitors. U.K. patent application no. GB 2,198,640A, relates to penicillin derivatives useful as anti-inflammatory and anti-degenerative agents. An article in Nature Vol. 322, 10 Jul. 1986, by J. B. Doherty et al. illustrates that cephalosporin antibiotics can be modified to inhibit human leukocyte elastase. Additionally, a study of 1,3-dipolar cycloaddition reactions of cephalosporin derivatives is provided in a paper entitled, "Cycloaddition Reactions of Cephalosporin Compounds XI" by J. Pitlik et al, *J. Heterocyclic Chem.*, 26, 461 (1989).

BRIEF SUMMARY OF THE INVENTION

In accordance with the present invention, there is provided novel 2-spirocyclopropyl cephalosporin sulfones having anti-elastase activity. Such derivatives, or elastase inhibitors, are useful in the prevention, control and treatment of inflammatory conditions, particularly rheumatoid arthritis, osteoarthritis, cystic fibrosis and emphysema.

In one aspect, the present invention relates to a 2-spirocyclopropyl cephalosporin sulfone compound of formula I:

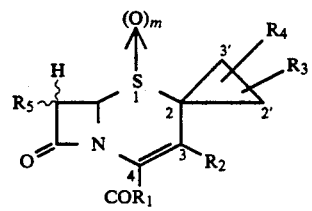

wherein $R_1$ is $OR_6$; or $NR_7R_8$;

$R_2$ is hydrogen; or a halogen; or a hydroxy group; or a $C_{1-6}$ alkoxy group; or an optionally substituted $C_{1-6}$ alkyl group; or an optionally substituted $C_{3-6}$ cycloalkyl group; or an optionally substituted $C_{2-6}$ alkenyl group; or an optionally substituted $C_{2-6}$ alkynyl group; or a trifluoromethyl group, or an aldehyde group, or a carboxylic acid group; or $CH_2X$; or $CH_2YR_9$;

$R_3$ and $R_4$, which may optionally be identical, are hydrogen, or an optionally substituted $C_{1-6}$ alkyl group, or an optionally substituted $C_{6-10}$ aryl group, or an optionally substituted $C_{3-8}$ cycloalkyl group, or an optionally substituted aralkyl group, or an optionally substituted saturated or unsaturated monocyclic or fused polycyclic 3-8 membered heterocyclic group, or a halogenated $C_{1-6}$ alkyl group, or a hydroxy $C_{1-6}$ alkyl group, or a $C_{1-6}$ alkanoyloxy $C_{1-6}$ alkyl group, or a —CH$_2$COOH group, or a —COOH group, or a COOC$_{1-6}$ alkyl group or a —CH$_2$COOC$_{1-6}$ alkyl group;

$R_5$ is hydrogen, or a halogen, or a hydroxy group, or a substituted oxy group, or a substituted thio group, or a substituted sulfinyl group, or a substituted sulfonyl group, or an alkylsulfonyloxy group, or an arylsulfonyloxy group, or a haloalkylsulfonyloxy group, or a $C_{1-6}$ alkanoyloxy group, or a halogenated $C_{1-6}$ alkanoyloxy group, or $R_{10}NH$;

$R_6$ is $C_{1-6}$ alkyl; or $C_{2-6}$ alkenyl; or $C_{2-6}$ alkynyl; or $C_{1-6}$ alkanoyl $C_{1-6}$ alkyl; or $C_{1-6}$ alkanoyloxy $C_{1-6}$ alkyl; or $C_{1-6}$ alkoxy $C_{1-6}$ alkyl; or $C_{3-6}$ cycloalkyl; or halogenated $C_{1-6}$ alkyl; or an optionally substituted phenyl wherein the phenyl may be substituted with at least of $C_{1-6}$ alkyl, $C_{1-6}$ alkoxy, $C_{1-6}$ alkylthio, $C_{1-6}$ alkanoyl, $C_{1-6}$ alkanoyloxy, nitro, $C_{1-6}$ alkylamino, amino, halogen, trifluoromethyl, $C_{1-6}$ alkylsulfinyl and $C_{1-6}$ alkylsulfonyl; or an optionally substituted —CH$_2$-phenyl; or an optionally substituted —CH(phenyl)$_2$, wherein the phenyl groups may be substituted with at least one of $C_{1-6}$ alkyl, $C_{1-6}$ alkoxy, $C_{1-6}$ alkylthio, $C_{1-6}$ alkanoyl, $C_{1-6}$ alkanoyloxy, nitro, $C_{1-6}$ alkylamino, amino, halogen, trifluoromethyl, $C_{1-6}$ alkylsulfinyl, and $C_{1-6}$ alkylsulfonyl;

$R_7$ is the same as $R_6$; or $C_{1-6}$ alkyl COOH; or $C_{1-6}$ alkoxycarbonyl $C_{1-6}$ alkyl; or $C_{2-6}$ alkenyloxy carbonyl $C_{1-6}$ alkyl; or an optionally substituted saturated or unsaturated monocyclic or fused polycyclic 3-8 membered heterocyclic group containing from 1 to 3 of any one or more of N, S or O in each heterocyclic ring, or $R_7$ together with $R_8$ may form an optionally substituted ring wherein the ring may be substituted with at least one of $C_{1-6}$ alkyl, hydroxy $C_{1-6}$ alkyl, halogenated $C_{1-6}$ alkyl, hydroxy, amino, mercaptan, guanidino, $C_{1-6}$ alkanoyloxy, —COOH, straight or branched $C_{1-6}$ alkyl COOH, $C_{1-6}$ alkoxycarbonyl, $C_{2-6}$ alkenyloxycarbonyl, $C_{1-6}$ alkoxycarbonyl $C_{1-6}$ alkyl, $C_{2-6}$ alkenyloxy carbonyl $C_{1-6}$ alkyl, $C_{1-6}$ alkanoyloxy $C_{1-6}$ alkyl, substituted or unsubstituted carboxamido group, and said ring may contain at least another heteroatom selected from N, S or O, in which case the ring may be substituted at the carbon atom or at the nitrogen atom by the groups mentioned above;

$R_8$ is $R_6$; or hydrogen; or, together with $R_7$, forms an optionally substituted ring as defined above;

$R_9$ is hydrogen; or an optionally substituted $C_{1-6}$ alkyl group; or an optionally substituted $C_{2-6}$ alkenyl group; or an optionally substituted $C_{2-6}$ alkynyl group; or an optionally substituted aryl group; or an optionally substituted aralkyl group; or an optionally substituted heterocyclic group; or an optionally substituted alkanoyl group; or an optionally substituted arylcarbonyl group; or an optionally substituted carbamoyl group; or an optionally substituted thiocarbamoyl group; or together with Y forms an optionally substituted heterocyclic group;

$R_{10}$ is hydrogen, or $C_{1-6}$ alkyl; or $R_{11}SO_2$;

$R_{11}$ is hydrogen or an optionally Substituted $C_{1-6}$ alkyl group, or a trifluoromethyl group, or an optionally substituted phenyl group, or an optionally substituted heterocyclic group;

X is hydroxy; or halogen; or an acetate; $C_{1-6}$ alkoxy; or $C_{1-6}$ alkanoyloxy; or arylcarbonyloxy; or an amino group; or $NHC_{1-6}$ alkyl; or $N(C_{1-6}$ alkyl$)_2$ or a triazolyl group; or $CONH_2$; or an N-alkyl derivative of $CONH_2$; or an N,N-dialkyl derivative of $CONH_2$; or

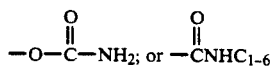

alkyl or a quaternary ammonium group;

Y is oxygen; or sulfur; or nitrogen; and m is 1 or 2;

or a pharmaceutically or veterinarily acceptable salt or ester thereof.

In a second aspect, the present invention relates to a method for preparing 2-spirocyclopropyl cephalosporin sulfone derivatives which comprises the following steps;

(1) providing a compound having the general formula II;

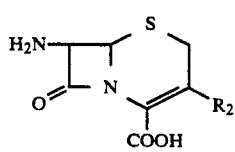

(2) esterifying the compound of formula II to thereby protect the carboxy group thereof and provide a compound having the general formula III;

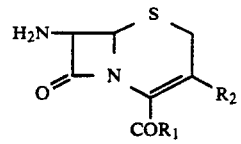

(3) halogenating the compound of formula III to provide a compound having the general formula IV;

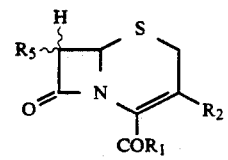

(4) oxidizing the compound of formula IV to provide a compound having the general formula V;

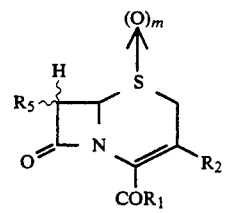

(5) aminomethylating the compound of formula V to provide a compound having the general formula VI; and

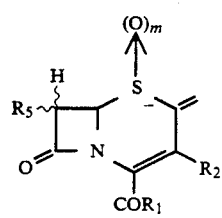

(6) carrying out a cycloaddition reaction to the compound of the general formula VI to provide a compound having the general formula I.

DETAILED DESCRIPTION OF THE PREFERRED EMBODIMENTS

As summarized above, the present invention relates to a 2-spirocyclopropyl cephalosporin sulfone derivative of the structural formula (I):

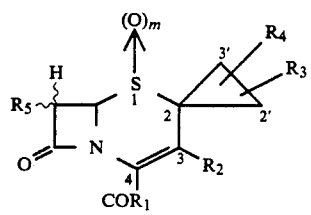

wherein $R_1$ in formula (I) represents $OR_6$ where $R_6$ is $C_{1-6}$ alkyl; $C_{2-6}$ alkenyl; $C_{2-6}$ alkynyl; $C_{1-6}$ alkanoyl $C_{1-6}$ alkyl; $C_{1-6}$ alkanoyl oxy $C_{1-6}$ alkyl; $C_{1-6}$ alkoxy $C_{1-6}$ alkyl; $C_{3-6}$ cycloalkyl; halo $C_{1-6}$ alkyl; aryl; aralkyl; or a heterocyclic group. These groups can be unsubstituted or can be substituted by one or more groups such as chloro, bromo, fluoro, hydroxy, alkoxy, mercapto, amino, substituted amino, nitro, cyano, carboxylic acid and carboxylate, sulfinyl, sulfonyl, alkanoyloxy, carbamoyloxy, alkanoyl carboxamides and N-substituted carboxamides.

$R_1$ in formula (I) also represents $NR_7R_8$, wherein $R_7$ is the same as $R_6$, and $R_8$ is the same as $R_6$ or hydrogen.

In the formula $NR_7R_8$, $R_7$ and $R_8$ may together form part of a heteroaromatic ring selected from a group consisting of:

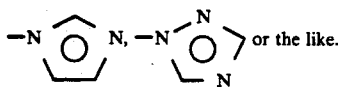

These ring systems can be further substituted by the groups as mentioned above.

In addition $R_7$ and $R_8$ may form part of a heterocyclic ring

containing 3 to 7 carbon atoms, which may in addition also contain at least one hetero atom such as N, S, and O.

Representative examples of such groups are:

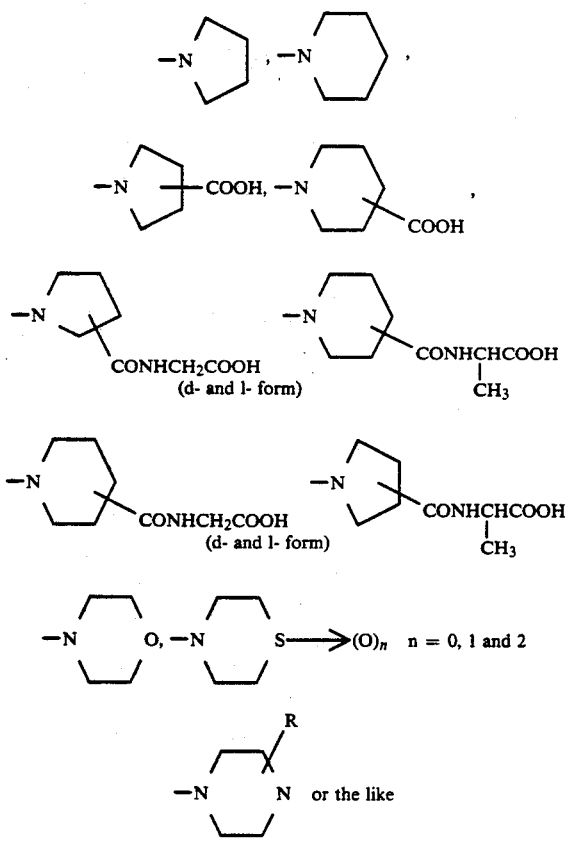

These rings can be further substituted at the carbon or at the nitrogen atom by the groups mentioned above.

Furthermore, the moiety $NR_7R_8$ may represent an amino acid, a dipeptide or a tripeptide moiety.

Preferably $R_6$ and $R_7$ are substituted or unsubstituted straight or branched loweralkyl, straight or branched loweralkenyl, cycloalkyl, haloalkyl, aryl, aralkyl, alkoxyloweralkyl, alkanoylloweralkyl, alkanoyloxyloweralkyl; and $R_8$ is the same as $R_6$ or hydrogen.

Preferred examples of such groups are methyl, ethyl, t-butyl, allyl, methoxyethyl, benzhydryl, benzyl, p-nitrobenzyl, p-methoxybenzyl, 2,2,2-trichloroethyl, pyrrolidine carboxamide, piperidine carboxamide, and the like.

$R_2$ is hydrogen, chloro, hydroxy, $C_{1-6}$ alkyl, $C_{2-6}$ alkenyl, $C_{2-6}$ alkynyl, cycloalkyl, $C_{1-6}$ alkoxy, trifluoromethyl, aldehyde, carboxylic acid; or —$CH_2X$ wherein X is hydroxy, chloro, bromo, fluoro, $C_{1-6}$ alkoxy, $C_{1-6}$ alkanoyloxy; arylcarbonyloxy; amino; —$NHC_{1-6}$ alkyl; —$N(C_{1-6}$ alkyl$)_2$; or a quaternary ammonium group (for example $N^{\oplus}H_3$, $N^{\oplus}HZ_2$, $N^{\oplus}Z_3$ where Z represents lower alkyl, aryl or aralkyl); —$CONH_2$; —$CONHC_{1-6}$ alkyl; —$CON(C_{1-6}$ alkyl$)_2$; —$OCONH_2$ or —O-$CONHC_{1-6}$ alkyl.

When $CH_2X$ is hydroxymethyl, the cephalosporin can also exist as the lactone which is formed by internal esterification with the adjacent carboxyl group.

In the formula $CH_2X$ when X is amino, the cephalosporin compound can also exist in the lactam form by loss of water with the adjacent carboxyl group.

$R_2$ can also be represented by the formula —$CH_2YR_9$ where Y is oxygen; sulfur; or nitrogen. $R_9$ is an acyl group, a straight or branched loweralkyl; alkenyl; alkynyl; aryl; aralkyl; or a heterocyclic group such as heteroaryl, heterocycloalkyl. These groups can be substituted by one or more functional groups, such as alkyl, alkoxy, halo, cyano, carboxy, haloalkyl, amino, substituted amino, hydroxy, carboxyalkyl, carbamoylalkyl, sulfinyl, sulfonyl or the like.

In the formula —$CH_2YR_9$, when Y is nitrogen, $R_9$ may represent the residue of amine. The term "the residue of an amine" for $R_9$ includes aliphatic, aromatic and heterocyclic primary amino residues. Suitable aliphatic amino primary residues include, for example, $C_{1-6}$ alkyl and $C_{3-6}$ cycloalkyl. Suitable primary aromatic amino residues include, for example, aryl and aryl $C_{1-6}$ alkyl. Suitable secondary aliphatic amino residues include, for example, di $C_{1-6}$ alkyl. Suitable secondary aromatic amino residues include for example, diaryl and bis aryl $C_{1-6}$ alkyl. In the formula —$CH_2YR_9$, Y may also be nitrogen which is part of the heterocyclic system, for example, morpholino, 4-methyl (or ethyl) piperazino, pyrrolidino, piperidino, pyridinium, etc.

Some representative examples of such groups are aminomethyl, N,N-dimethylaminomethyl, N,N-diethylaminomethyl, 1,2,3-triazol-1-yl-methyl, 1,2,4-triazol-1-yl-methyl, triazoles substituted with one or more functional groups consisting of chloro, fluoro, bromo, hydroxy, carboxy, carbomethoxy, carboethoxy, hydroxyalkyl, cyano, amino, substituted amino, and the like.

Some representative examples of quaternary ammonium groups are:

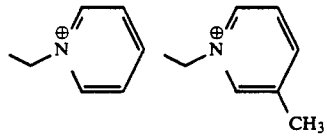

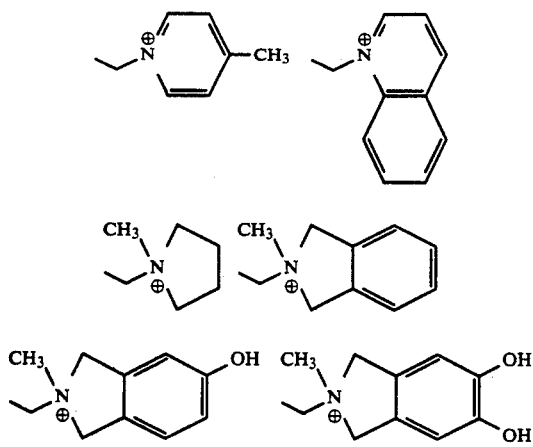

In the formula —CH$_2$YR$_9$ when Y is sulfur, R$_9$ may be hydrogen or the residue of a thiol compound. The term "residue of a thiol compound" means a residue obtained by omitting the —SH group from a thiol compound. Suitable thiol compounds include a cyclic or acyclic aliphatic thiol, aromatic thiol, or a heterocyclic thiol compound. Suitable aliphatic residues include: straight or branched chain alkyl having from 1 to 20 carbon atoms, especially methyl, ethyl, isopropyl, t-butyl, pentyl, hexyl, etc.; cycloalkyl having from 3 to 8 carbon atoms, especially cyclopropyl, cyclobutyl, cyclopentyl, etc.; alkenyl having from 2 to 20 carbon atoms especially C$_{2-6}$ alkenyl, such as vinyl, allyl, etc.; and alkynyl having from 2 to 20 carbon atoms, especially C$_{2-6}$ alkynyl, such as ethynyl, propynyl or hexynyl, etc.

Suitable aromatic residues include: aryl having from 6 to 10 carbon atoms, especially phenyl. Phenyl can be substituted, for example, tolyl; aralkyl, for example, benzyl. Suitable heterocyclic groups include monoheteroaryl, di- or polyheteroaryl, or fused heteroaryl containing from 1 to 3 of any one or more of the heteroatoms N, S, or O, in each heteroaryl ring.

Examples of such heterocyclic groups that might be mentioned are: unsaturated 3 to 8 membered heteromonocyclic systems containing to 4 nitrogen atoms, for example, pyrolyl, pyrrolinyl, imidazolyl, pyrazolyl, pyridyl and its N-oxide, pyrimidyl, pyrazinyl, triazolyl (e.g. 4H-1,2,4-triazolyl, 1H-1,2,3-triazolyl, 2H-1,2,3-triazolyl, etc) and tetrazolyl (e.g. 1H-tetrazolyl, 2H-tetrazolyl, etc) saturated 3 to 8-membered heteromonocyclic groups containing 1 to 4 nitrogen atoms may include, for example, pyrrolidinyl, imidazolidinyl, piperidino, or piperazinyl; unsaturated condensed heterocyclic groups containing 1 to 5 nitrogen atoms may comprise, for example, indolyl, quinolyl, benzimidazolyl, or benzotriazolyl; saturated 3 to 8-membered heteromonocyclic groups containing 1 to 2 oxygen atoms and 1 to 3 nitrogen atoms may comprise, for example, morpholinyl; unsaturated 3 to 8-membered heteromonocyclic groups containing an oxygen atom would be furyl, for example; unsaturated condensed heterocyclic groups containing 1 to 2 oxygen atoms and 1 to 3 nitrogen atoms may include, for example, benzoxazolyl, benzoxadiazolyl; or unsaturated 3 to 8-membered heteromonocyclic groups containing 1 to 2 sulfur atoms and 1 to 3 nitrogen atoms, could comprise thiazolyl, thiadiazolyl, e.g. 1,2,4-thiadiazolyl, 1,3,4-thiadiazolyl, 1,2,5-thiadiazolyl.

A typical saturated 3 to 8-membered heteromonocyclic group containing 1 to 2 sulfur atoms and 1 to 3 nitrogen atoms would be for example, thiazolidinyl. An example of an unsaturated 3 to 8-membered heteromonocyclic group containing a sulfur atom would be thienyl. Unsaturated condensed heterocyclic groups containing 1 to 2 sulfur atoms and 1 to 3 nitrogen atoms may be selected from benzothiazolyl, benzothiadiazolyl or the like.

The above mentioned heterocyclic groups may be substituted with 1 to 6 appropriate substituents such as C$_{1-6}$ alkyl radical (e.g. methyl, ethyl), or a C$_{1-6}$ alkoxy radical (e.g., methoxy, ethoxy), or a halogen atom (e.g., fluorine, chlorine, bromine), or an aryl radical (e.g. phenyl, tolyl), or a substituted aryl radical (e.g. chlorophenyl, nitrophenyl), or a cyano group, or an amino group, or a hydroxy group, or the like.

In the formula CH$_2$YR$_9$ when Y is sulfur, it is also to be understood that the —S— group may be present in the sulfoxide or the sulfone form:

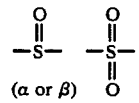

The preferred groups representing R$_2$ are: hydrogen, chloro, hydroxy, methoxy, methyl, trifluoromethyl, cyclopropyl, vinyl, acetoxymethyl, methoxymethyl, methylthiomethyl, chloromethyl, bromomethyl, benzoyloxymethyl, carbamoyloxymethyl, (N-methylcarbamoyl) oxymethyl, (N-ethylcarbamoyl) oxymethyl, hydroxymethyl, N,N-dimethylthiocarbamoylthiomethyl, N,N-diethylthiocarbamoylthiomethyl, N-methylpiperazinium-1-thiocarbonylthiomethyl, N,N-dimethylpiperazinium-1-thiocarbonylthiomethyl, (5-methyl-1,3,4-thiadiazol-2-yl) thiomethyl, 1-methyl-1,2,3,4-tetrazolyl-5-thiomethyl.

More preferably R$_2$ is: hydrogen, chloro, hydroxy, methoxy, methyl, trifluoromethyl, cyclopropyl, vinyl, methoxymethyl, ethoxymethyl, chloromethyl, bromomethyl, hydroxy methyl, acetoxymethyl, carbamoyloxymethyl, (N-methylcarbamoyl)oxymethyl, (N-ethylcarbamoyl)oxymethyl, acylthio,

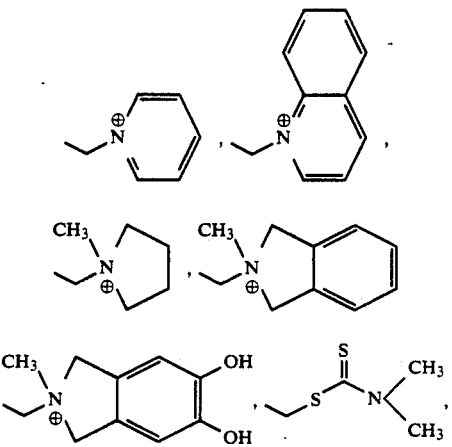

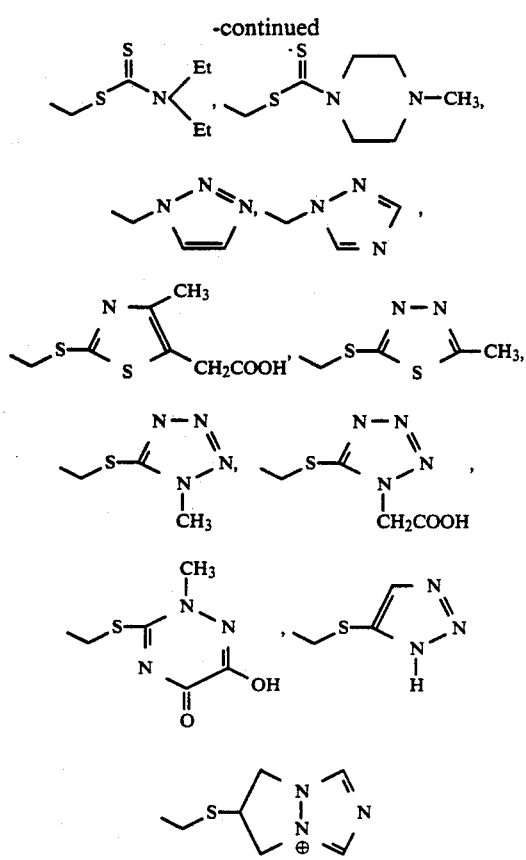

The substituents $R_3$ and $R_4$ in formula (I) may be the same or different and may comprise hydrogen; straight or branched loweralkyl; straight or branched loweralkenyl; cycloalkyl; haloalkyl; hydroxyalkyl; alkoxyloweralkyl, alkanoylloweralkyl; alkanoyloxyloweralkyl; aryl; aralkyl; —COOH; —CH$_2$COOH; —COOC$_{1-6}$ alkyl; —CH$_2$COOC$_{1-6}$ alkyl; trifluoromethyl; unsubstituted or substituted phenylthio C$_{1-6}$ alkyl; phenylsulfonyl C$_{1-6}$ alkyl; a monocyclic (or fused polycyclic) saturated or unsaturated heterocyclic group containing from 1 to 3 of any one or more of the heteroatoms N, S or O in each heterocyclic ring; heteroarylalkyl such as 2-pyridylmethyl, 2-thienylmethyl or the like.

The above groups can be further substituted with one or more groups such as alkyl, alkoxy, hydroxy, halogen, haloalkyl, hydroxyalkyl, nitro, amino, substituted amino, cyano, carboxy, acyloxy, carboxamido, sulfinyl, sulfonyl, etc.

More preferably $R_3$ and $R_4$ are hydrogen; C$_{1-6}$ alkyl, especially methyl, ethyl, isopropyl, t-butyl, n-pentyl; halo C$_{1-6}$ alkyl, especially chloromethyl, fluoromethyl; cyclopropyl, phenyl, p-chlorophenyl, p-fluorophenyl, benzyl, p-carbomethoxybenzyl, p-carbomethoxyphenyl, trifluoromethyl, —COOH, —CH$_2$COOH, —CH$_2$COOC$_{1-6}$ alkyl especially —CH$_2$COOCH$_3$, —CH$_2$COOEt, pyridyl, thienyl, furyl, isoxazolyl, and the like.

$R_5$ is hydrogen, or a halogen, or a hydroxy group, or a substituted oxy group, or a substituted thio group, or a substituted sulfinyl group, or a substituted sulfonyl group, or an alkylsulfonyloxy group, or an arylsulfonyloxy group, or a haloalkylsulfonyloxy group, or a C$_{1-6}$ alkanoyloxy group, or a halogenated C$_{1-6}$ alkanoyloxy group, or R$_{10}$NH; wherein R$_{10}$ is hydrogen, or C$_1$-C$_6$ alkyl, or R$_{11}$SO$_2$ $R_{11}$ is hydrogen or a C$_{1-6}$ alkyl group; or a trifluoromethyl group; or an optionally substituted phenyl group; or an optionally substituted heterocyclic group. Representative members of sulfonamido group are: phenylsulfonamide, trifluoromethane sulfonamide, methylsulfonamide, ethyl sulfonamide, and the like.

Preferably, $R_5$ is hydrogen, chloro, bromo, fluoro, methoxy, ethoxy, methylsulfonamido, trifluoromethyl sulfonamido, methanesulfonyloxy, trifluoromethane sulfonyloxy and m is 2.

The partial structure represented by the formula:

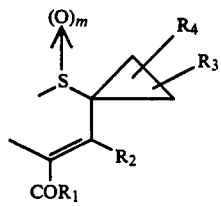

is to be understood to include both the regio isomers as represented by the formula

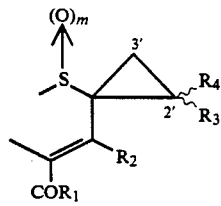

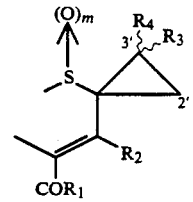

Furthermore, it should be noted that when $R_3$ and $R_4$ in formula (I) are different they may be present in the form of an optical isomer, for example, l-, d- or dl-forms.

The present invention includes the salts of those compounds of formula (I) that have salt forming groups, especially the salts of the compounds having a carboxylic group, a basic group (e.g. an amino, piperazino, or guanidino group) or a quarternary ammonium group. Preferred salts include physiologically tolerable salts, for example, alkali metal and alkaline earth metal salts (e.g. sodium, potassium, lithium, calcium and magnesium salts), ammonium salts and salts with an appropriate organic amine or amino acid (e.g. arginine, procaine salts), and the addition salts formed with suitable organic or inorganic acids, for example, hydrochloric acid, sulfuric acid, carboxylic and sulfonic organic acids (e.g. acetic, trifluoroacetic, p-toluene sulfonic acid). Some compounds of formula (I) which contain a carboxylate and an ammonium group may exist as zwitterions.

The present invention also includes those compounds of formula (I) that have suitably pharmaceutically acceptable in vivo hydrolysable esters namely those esters which hydrolyse in the human body to produce the parent acid or its salt. Examples of suitable in vivo hydrolysable ester groups include acetoxymethyl, pivaloyloxymethyl, α-acetoxymethyl, α-acetoxybenzyl, α-pivaloyloxyethyl, ethoxycarbonyloxymethyl, α-ethoxycarbonyloxyethyl and other such groups which have been or can be used in the penicillin and cephalosporin art.

More specifically the most preferred embodiments of the present invention comprise the following compounds:

Benzhydryl 7α-chloro-2-spiro (2',2'-diphenyl) cyclopropyl-3-methyl-3-cephem-4-carboxylate-1,1-dioxide;

Benzhydryl 7α-bromo-2-spiro (2',2'-diphenyl) cyclopropyl-3-methyl-3-cephem-4-carboxylate-1,1-dioxide;

Benzhydryl 7,7-dihydro-2-spiro (2',2'-diphenyl) cyclopropyl-3-methyl-3-cephem-4-carboxylate-1,1-dioxide;

t-Butyl 7α-bromo-2-spiro (2',2'-diphenyl) cyclopropyl-3-methyl-3-cephem-4-carboxylate-1,1-dioxide;

Benzhydryl 7α-bromo-2-spiro [2',2'-(4',4'-dichloro)-diphenyl] cyclopropyl-3-methyl-3-cephem-4-carboxylate-1,1-dioxide;

Benzhydryl 7α-bromo-2-spiro [2',2'-(4',4'-difluoro) diphenyl] cyclopropyl-3-methyl-3-cephem-4-carboxylate-1,1-dioxide;

t-Butyl 7α-chloro-2-spiro (2',2'-diphenyl) cyclopropyl-3-acetoxymethyl -3-cephem-4-carboxylate-1,1-dioxide;

Benzhydryl 7α-bromo-2-spiro (2'-ethoxycarbonyl) cyclopropyl-3-methyl-3-cephem-4-carboxylate-1,1-dioxide;

Benzhydryl 7α-bromo-2-spiro (2'-phenyl,2'-methyl) cyclopropyl-3-methyl-3-cephem-4-carboxylate-1,1-dioxide;

Benzhydryl 7α -bromo-2-spiro (2'-phenyl) cyclopropyl-3-methyl-3-cephem-4-carboxylate-1,1-dioxide;

Benzhydryl-7α-methoxy-2-spiro (2',2'-diphenyl) cyclopropyl-3-methyl-3-cephem-4-carboxylate-1,1-dioxide;

2,2,2-Trichloroethyl-7α-methoxy-2-spiro (2',2'-diphenyl) cyclopropyl-3-methyl-3-cephem-4-carboxylate-1,1-dioxide;

7α-Methoxy-2-spiro (2',2'-diphenyl) cyclopropyl-3-methyl-3-cephem-4-pyrrolidine carboxamide-1,1-dioxide;

7α-Methoxy-2-spiro (2',2'-diphenyl) cyclopropyl-3-methyl- 3-cephem-4-piperidine carboxamide-1,1-dioxide;

2,2,2-Trichloroethyl-7α-ethoxy-2-spiro (2',2'-diphenyl) cyclopropyl-3-methyl-3-cephem-4-carboxylate-1,1-dioxide;

7α-Bromo-2-spiro (2',2'-diphenyl) cyclopropyl-3-methyl-3-cephem-4-pyrrolidine carboxamide-1,1-dioxide;

p-Methoxybenzyl 7α-bromo-2-spiro (2',2'-diphenyl) cyclopropyl-3-chloromethyl-3-cephem-4-carboxylate-1, 1-dioxide;

Benzhydryl 7α-bromo-2-spiro [2',2'- (4',4'-dichloro)-diphenyl] cyclopropyl-3- [[(5-methyl-1,3,4-thiadiazol-2-yl) sulfonyl] methyl]-3-cephem-4-carboxylate-1,1-dioxide;

7α-methoxy-2-spiro(2',2'-diphenyl)cyclopropyl-3-methyl-3-cephem-4-[2-(s)-t-butoxycarbonyl pyrrolidine carboxamide]-1,1-dioxide; and 7α-methoxy-2-spiro(2',2'-diphenyl) cyclopropyl-3-methyl-3-cephem-4-(N-methyl piperazine carboxamide)-1,1-dioxide.

In accordance with a second broad aspect of the invention, there is provided a process for preparing 2-spirocyclopropyl cephalosporin sulfone derivatives of the structural formula I which comprises the following steps (Scheme I).

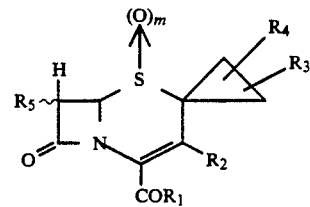

(1) providing a compound having the structural formula II;

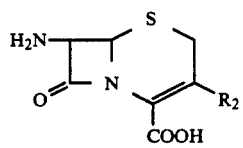

(2) esterifying the compound of formula II to thereby protect the carboxy group thereof and provide a compound having the structural formula III;

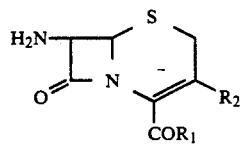

(3) halogenating the compound of formula III to provide a compound having the structural formula IV;

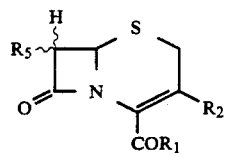

(4) oxidizing the compound of formula IV to provide a compound having the structural formula V;

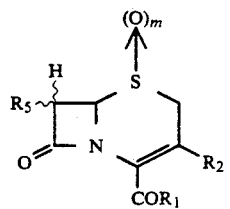

(5) aninomethylating the compound of formula V to provide a compound having the structural formula VI; and

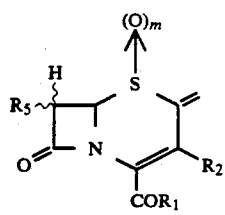

(6) carrying out a cycloaddition reaction of the compound of the structural formula VI to provide a compound having the structural formula I.

Alternatively steps (2) and (3) may be conducted in reverse order.

The following synthetic routes are useful in preparing the compound having the structural formula (I):

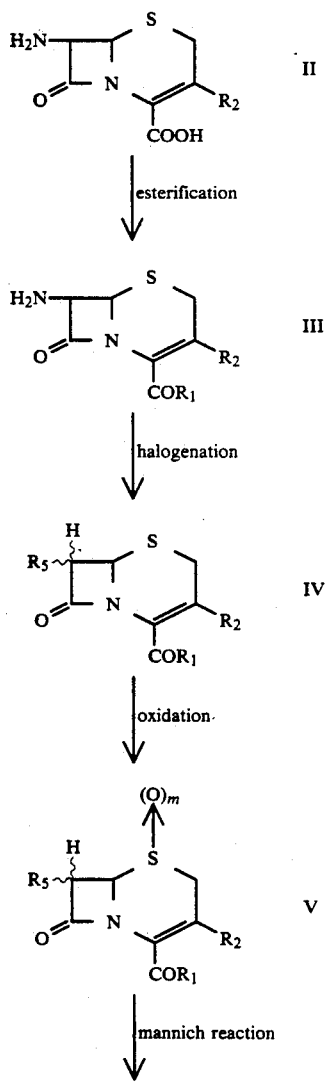

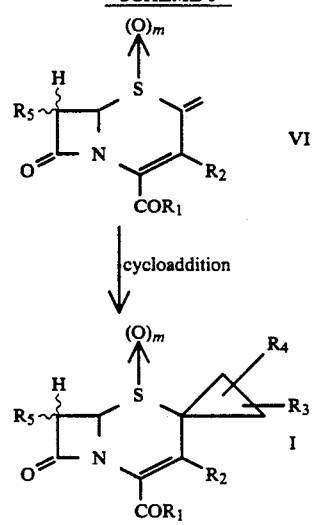

There is also provided a method for preparing 7-substituted cephalosporin derivatives which comprises the following steps: (Scheme II)

(1) providing the compound having the formula VII;

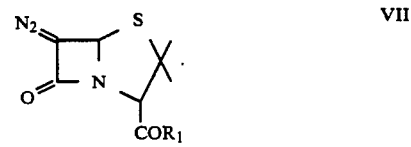

(2) treating the compound VII with an appropriate alcohol (e.g., methanol, ethanol, etc.) to provide a compound having the formula VIII;

(3) oxidizing the compound VIII with a suitable oxidizing agent (e.g., m-chloro peroxy benzoic acid, peracetic acid, etc.) to provide a sulfoxide having the formula IX;

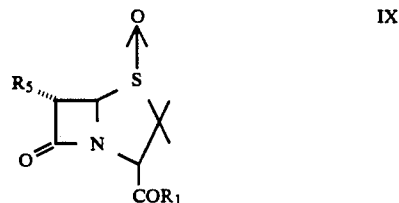

(4) heating the compound IX with a suitable mercaptan (e.g., 2-mercaptobenzothiazole) in a suitable organic solvent (e.g., benzene, toluene, etc.) to provide the compound having the formula X

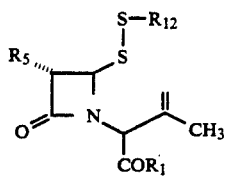

(5) treating the compound X with a suitable halogenating agent (e.g., chlorine, bromine, etc.) to provide a compound having the formula XI

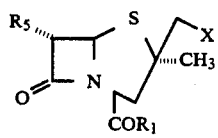

(6) treating the compound XI with an organic base (e.g., pyridine, triethylamine, etc.) in a solvent like dimethyl sulfoxide to provide the 7α- substituted cephalosporin derivative having the formula XII

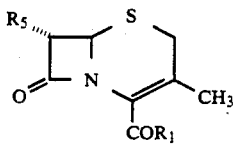

Alternatively, cephalosporin derivative XII can also be obtained by heating the sulfoxide IX with acetic anhydride in dimethyl formamide.

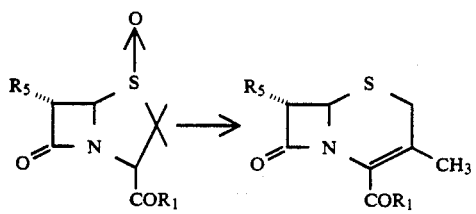

The following synthetic routes are useful in preparing the 7α-substituted cephalosporin derivative XII (Scheme II)

SCHEME II

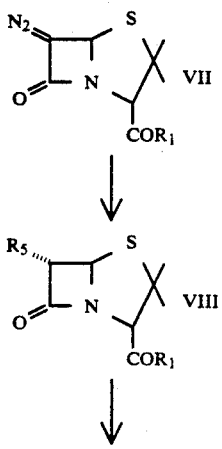

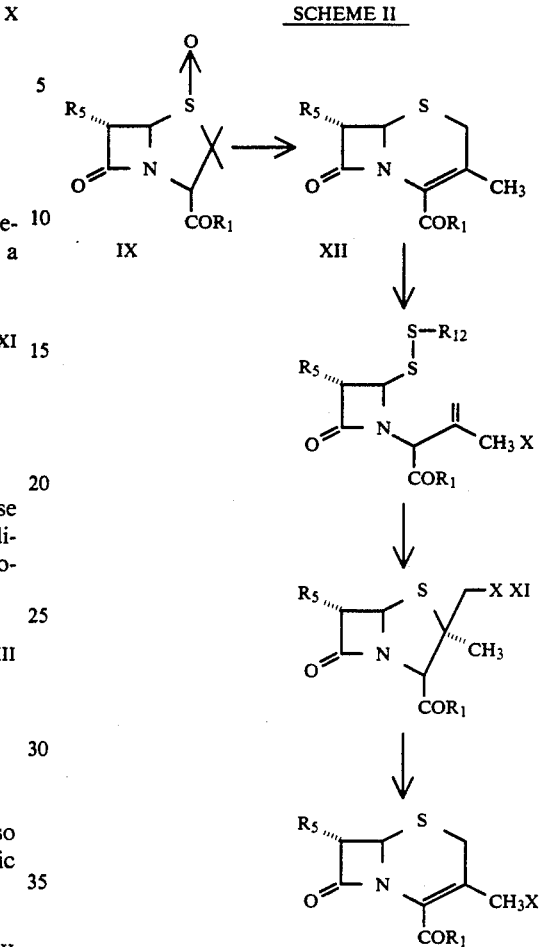

Esterification or Amidation

The carboxyl group of compound II can be protected according to the conventional methods described in the cephalosporin and penicillin literature. For example, a suitable salt of the compound II may be reacted with an alkyl halide, such as, benzyl bromide, 4-nitrobenzyl bromide, methyl iodide, allyl bromide or the like. The salts of compound II may be salts with an inorganic base such as alkali metal salts (e.g., sodium or potassium) or an alkaline earth metal salt (e.g., calcium or magnesium), the hydroxide, carbonate or bicarbonate thereof, a salt with an organic base such as trimethylamine, triethylamine, pyridine, N,N-dialkylamine,1,5-diazabicyclo [4,3,0]non-5-ene,1,4-diazabicyclo[2,2,2]-octane, 1,8-diazabicyclo[5,4,0]undec-7-ene etc.

The carboxyl group of compound II can also be converted into an ester by other alkylation methods, for example, by treatment with diazomethane or diphenyldiazomethane or the like.

The carboxyl group can be converted to an ester by treatment with a lower alkanol e.g., methanol, ethanol, in the presence of a catalyst such as hydrochloric or hydrobromic acid, sulfuric acid, phosphoric acid, trichloracetic acid, trifluoroacetic acid, or p-toluenesulfonic acid and a Lewis acid. Suitable Lewis acids for this reaction include, for example, boron halide (e.g., boron trichloride, boron trifluoride, titanium halide (e.g., titanium chloride, titanium bromide), stannic halide, aluminium halide, zinc chloride, ferric chloride and the like.

Treatment with a lower alkene (e.g., isobutylene), in the presence of a suitable acid catalyst (e.g., sulfuric acid) is also a preferable method of protecting the carboxyl group.

Esterification can also be carried out in the presence of a conventional condensing agent such as N,N-dicyclohexylcarbodiimide, N,N-diethylcarbodiimide, N,N-diisopropylcarbodiimide, or N,N-carbonyldiimidazole.

Another method of esterification (also suitable for amidation) is by conversion of the carboxyl group to a suitable reactive derivative followed by reaction with an appropriate alcohol (or amine). Suitable reactive derivatives of the carboxyl group may include an acid halide, a mixed or symmetrical anhydride, an activated amide or the like. A suitable example may be an acid chloride or bromide via treatment with a halogenating agent such as thionyl chloride, phosphorus pentachloride or phosphorus oxychloride.

The reactions are usually carried out in a conventional solvent such as acetone, dioxane, acetonitrile, chloroform, methylene chloride, ethylene chloride, tetrahydrofuran, ethyl acetate, N,N-dimethylformamide or any other organic solvent which does not adversely influence the reaction.

An interesting class of amides is that where the amine reactant is an amino acid or a peptide. The amino acid may be one of the naturally occurring amino acids, glycine, alanine, valine, leucine, isoleucine, serine, threonine, cysteine, cystine, methionine, asparagine, glutamine, aspartic acid, glutamic acid, lysine, arginine, phenylalanine, tyrosine, proline, hydroxyproline and tryptophan, or peptides containing or made from these amino acids. Of particular interest are amides made from amines which are dipeptides, such as proline-alanine, proline-valine, and proline-glycine.

The procedure used to prepare amides wherein the amine reactant is an amino acid or peptide is essentially the same as that used for the preparation of peptides. Such procedures are well known to those ski)led in the art and involve the selective protection of end groups, a coupling step to form the peptide or amide bond, and a deprotection step. For example, dipeptides are prepared by activation of the carboxyl group in an N-protected amino acid (using Cbz or Boc as the blocking group) and adding an amino acid ester to the activated carboxyl group (the C-protecting group is an alkyl or benzyl ester). Tri- and higher peptides are prepared in a similar manner. It is noted that the carboxylic acid corresponding to the compound of formula I ($R_1$=OH) may optionally contain an amino group, which, if present, would be protected as is customary in peptide synthesis.

Halogenation

It should be noted that when it is appropriate the compound II can be halogenated first and then subjected to esterification according to the procedures as described before.

The compound IV, wherein $R_5$ is a halogen, can be prepared by subjecting the amino group of compound II to the diazotization reaction in accordance with conventional methods in the presence of a hydrogen halide or a metal halide. Suitable hydrogen halides used in the present reaction include, for example, hydrogen chloride, hydrogen bromide, and hydrogen iodide. Suitable metal halides include sodium bromide, potassium bromide, and cupric chloride. The present reaction is preferably carried out under mild conditions such as under cooling, at ambient or slightly elevated temperatures.

Oxidation

The compound V in the present invention can be prepared by oxidizing the compound IV. The present oxidizing reaction is carried out under conditions wherein the —S— group can be converted to the sulfoxide or sulfone, most preferably to the sulfone. Typical oxidizing agents can be utilized such as for example, phenyliodododichloride, ozone, isocyanuroyl chloride, periodic acid, perbenzoic acid, m-chloroperbenzoic acid, performic acid, peracetic acid, trifluoroperacetic acid, or hydrogen peroxide.

The present oxidizing reaction is usually carried out in the presence of a solvent such as chloroform, methylene chloride, dioxane, benzene, ethyl acetate, or other solvents which does not adversely affect the reaction. The reaction is usually carried out at room temperature or under cooling.

Aminomethylation (Mannich Reaction)

The introduction of the exocyclic double bond at the 2-position of compound V can be carried out according to the procedure detailed in the literature; [I. G. Wright et al., *J. Med. Chem.*, 14, 420 (1971), incorporated herein by reference]. The reaction is usually carried out in a solvent such as alcohol (e.g. t-butanol), methylene chloride, chloroform, carbon tetrachloride, mixed solvent thereof, or any other solvent not adversely affecting the reaction.

There is no particular limitation to the reaction temperature and the present reaction is usually carried out from room temperature to about 150° C. with or without reflux until the reaction is complete.

Cycloaddition

For the introduction of the 2-spirocyclopropyl groups which may be substituted with suitable substituents, the reaction is carried out by reacting the compound VI with a compound of the formula $R_3R_4CN_2$ where $R_3$ and $R_4$ may be the same or different and represent the groups as defined earlier herein. The reaction is usually carried out in a solvent such as methylene chloride, chloroform, carbon tetrachloride, benzene, ether, ethyl acetate or any other solvent which does not adversely affect the reaction. The reaction is usually carried out under cooling to ambient temperature.

Biological Evidence

The in vitro test data on anti-elastase activity of exemplary derivatives having the structural formula I are shown in Table I herebelow.

TABLE I

ACTIVITY OF 2-SPIROCYCLOPROPYL CEPHALOSPORIN SULFONES AGAINST HLE

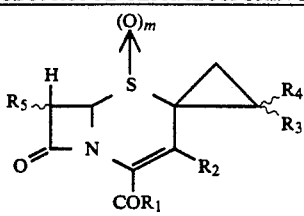

| $R_5$ | m | $R_1$ | $R_2$ | $R_3$(or $R_4$) | $R_4$(or $R_3$) | $IC_{50}$ ($\mu$g ml$^{-1}$) |
|---|---|---|---|---|---|---|
| Cl | 2 | OCHPh$_2$ | CH$_3$ | Ph | Ph | 0.0029 |
| Br | 2 | OCHPh$_2$ | CH$_3$ | Ph | Ph | 0.022 |
| H | 2 | OCHPh$_2$ | CH$_3$ | Ph | Ph | 0.086 |
| Br | 2 | OBu$^t$ | CH$_3$ | Ph | Ph | 0.0027 |
| Br | 2 | OCHPh$_2$ | CH$_3$ | p-Cl.C$_6$H$_4$ | p-Cl.C$_6$H$_4$ | 0.0073 |
| Br | 2 | OCHPh$_2$ | CH3 | p-F.C$_6$H$_4$ | p-F.C$_6$H$_4$ | 0.0035 |
| Cl | 2 | OBu$^t$ | CH$_2$OAc | Ph | Ph | 0.051 |
| Br | 2 | OCHPh$_2$ | CH$_3$ | H | COOEt | 0.037 |
| Br | 2 | OCHPh$_2$ | CH$_3$ | Ph | CH$_3$ | 0.0028 |
| Br | 2 | OCHPh$_2$ | CH$_3$ | Ph | H | 0.0038 |
| Br | 2 | —N(pyrrolidine) | CH$_3$ | Ph | Ph | 0.0058 |
| CH$_3$O | 2 | —N(pyrrolidine) | CH$_3$ | Ph | Ph | 0.022 |
| EtO | 2 | OCH$_2$CCl$_3$ | CH$_3$ | Ph | Ph | 0.0032 |
| CH$_3$O | 2 | OCHPh$_2$ | CH$_3$ | Ph | Ph | 0.0022 |
| CH$_3$O | 2 | OCH$_2$CCl$_3$ | CH$_3$ | Ph | Ph | 0.0025 |
| CH$_3$O | 2 | —N(piperidine) | CH$_3$ | Ph | Ph | 0.0054 |
| Br | 2 | OCH$_2$-C$_6$H$_4$-OMe | CH$_2$Cl | Ph | Ph | 0.0026 |
| Br | 1 | OCHPh$_2$ | CH$_2$-S-(thiadiazole)-CH$_3$ | p-Cl.C$_6$H$_4$ | p-Cl.C$_6$H$_4$ | 0.041 |

The compounds tested were as follows:
Benzhydryl-7α-chloro-2-spiro(2',2'-diphenyl)cyclopropyl-3-methyl-3-cephem-4-carboxylate-1,1-dioxide.
Benzhydryl-7α-bromo-2-spiro(2',2'-diphenyl)cyclopropyl-3-me thyl-3-cephem-4-carboxylate-1,1-dioxide.
Benzhydryl-7,7-dihydro-2-spiro(2',2'-diphenyl)cyclopropyl-3-methyl-3-cephem-4-carboxylate-1,1-dioxide.
t-Butyl 7α-bromo-2-spiro(2',2'-diphenyl)cyclopropyl-3-methyl-3-cephem-4-carboxylate-1,1-dioxide.
Benzhydryl-7α-bromo-2-spiro[2',2'-(4',4'-dichloro)-diphenyl] cyclopropyl-3-methyl-3-cephem-4-carboxylate-1,1-dioxide.
Benzhydryl-7α-bromo-2-spiro[2',2'-(4',4'-difluoro)-diphenyl] cyclopropyl-3-methyl-3-cephem-4-carboxylate-1,1-dioxide.
t-Butyl-7α-chloro-2-spiro(2',2'-diphenyl)cyclopropyl-3-acet oxymethyl-3-cephem-4-carboxylate-1,1-dioxide.
Benzhydryl-7α-bromo-2-spiro(2'-ethoxycarbonyl)cyclopropyl-3 methyl-3-cephem-4-carboxylate-1,1-dioxide.
Benzhydryl-7α-bromo-2-spiro(2'-phenyl-2'-methyl)cyclopropyl -3-methyl-3-cephem-4-carboxylate-1,1-dioxide.
Benzhydryl-7α-bromo-2-spiro(2'-phenyl)cyclopropyl-3-methyl-3-cephem-4-carboxylate-1,1-dioxide.
7α-Bromo-2-spiro(2',2'-diphenyl)cyclopropyl-3-methyl-3-cephem-4-pyrrolidine carboxamide-1,1-dioxide.
7α-methoxy-2-spiro(2',2'-diphenyl)cyclopropyl-3-methyl-3-cephem-4-pyrrolidine carboxamide-1,1-dioxide.
2,2,2-Trichloroethyl-7α-ethoxy-2-spiro(2',2'-diphenyl) cyclopropyl-3-methyl-3-cephem-4-carboxylate-1,1-dioxide.
Benzhydryl-7'-methoxy-2-spiro(2',2'-diphenyl)cyclopropyl-3-methyl-3-cephem-4-carboxylate-1,1-dioxide. 2,2,2-Trichloroethyl-7α-methoxy-2-spiro(2',2'- diphenyl) cyclopropyl-3-methyl-3-cephem-4-carboxylate-1,1-dioxide. 7α-Methoxy-2-spiro(2',2'-diphenyl)cyclopropyl-3-methyl-3-cephem-4-piperidine carboxamide-1,1-dioxide. p-Methoxybenzyl 7α-bromo-2-spiro(2',2'-diphenyl) cyclopropyl-3-chloromethyl-3-cephem-4- carboxylate-1, 1-dioxide. Benzhydryl-7α-bromo-2-spiro[2',2'-(4',4'-dichloro)diphenyl]-cyclopropyl-3-[(5-methyl-1,3,4-thiadiazol-2-yl)thiomethyl]-3-cephem-4-carboxylate-1-oxide.

some of these compounds were further tested against various proteases and the $IC_{50}$ values are shown in Table II herebelow.

TABLE II
SELECTIVITY OF 2-SPIROCYCLOPROPYL CEPHALOSPORIN SULFONES AGAINST VARIOUS PROTEASES $IC_{50}$ ($\mu g\ ml^{-1}$)

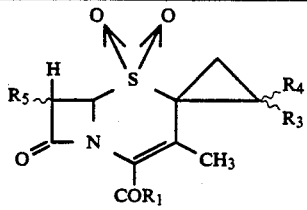

| $R_5$ | $R_1$ | $R_3$(or $R_4$) | $R_4$(or $R_3$) | TRY | THR | PTH | CTC | ATM | CTG | CTD | PPE |
|---|---|---|---|---|---|---|---|---|---|---|---|
| Br | $OCHPh_2$ | Ph | Ph | >24.2 | >26.2 | 2.1 | >25.2 | >26.2 | >10.6 | >32.7 | 0.012 |
| Cl | $OCHPh_2$ | Ph | Ph | >36.6 | >24.4 | 2.2 | >36.6 | >36.6 | 12.2 | >30.5 | 0.020 |
| Br | $OBu^t$ | Ph | Ph | >21.8 | >22.8 | 3.0 | >21.8 | >21.8 | 21.8 | >27.2 | 0.051 |
| Br | $OCHPh_2$ | H | COOet | 0.333 | >23 | 6.32 | >23 | >23 | 7.47 | >28.7 | 0.018 |
| Br | $OCHPh_2$ | $p\text{-}Cl.C_6H_4$ | $p\text{-}Cl.C_6H_4$ | 40 | >40 | 1.6 | >40 | >40 | 14.0 | >33.4 | 0.17 |
| Br | $OCHph_2$ | $p\text{-}F.C_6H_4$ | $p\text{-}F.C_6H_4$ | >27.6 | >27.6 | 2.2 | >27.6 | >27.6 | 13.1 | >34.5 | 0.044 |
| Br | $OCHPh_2$ | Ph | $CH_3$ | 0.087 | >23.7 | 3.26 | >23.7 | >23.7 | 23.7 · | >27.6 | 0.033 |
| Br | —N⟨⟩ (5-ring) | Ph | Ph | >21.1 | >21.1 | >21.1 | >5.29 | >5.29 | >21.1 | >5.29 | 0.11 |
| $CH_3O$ | —N⟨⟩ (5-ring) | Ph | Ph | >17.7 | >19.7 | >19.7 | >4.92 | >19.7 | >15.2 | >4.91 | 0.041 |
| EtO | $OCH_2CCl_3$ | Ph | Ph | >5.85 | >5.85 | >5.85 | >5.85 | >5.85 | 0.187 | >5.85 | 0.0094 |
| $CH_3O$ | $OCHPh_2$ | Ph | Ph | >6.06 | >6.06 | 5.33 | >6.06 | >6.06 | >6.06 | >5.06 | 0.033 |
| $CH_3O$ | $OCH_2CCl_3$ | Ph | Ph | 0.37 | >5.70 | 0.742 | >5.70 | >5.70 | 0.23 | >5.70 | 0.013 |
| $CH_3O$ | —N⟨⟩ (6-ring) | Ph | Ph | >5.07 | >20.2 | >5.07 | >5.07 | >5.07 | >5.07 | 0.016 | |

HLE, CTG, PPE and CTD were tested at 30° C. and the others were tested at 22° C.
TRY, trypsin; THR, thrombin; PTH, plasmin; CTC, cathepsin C; ATM, aminopeptidase M; CTG, cathespin G; CTD, cathespin D; PPE, porcine pancreatic elastase.

PROTOCOL

Enzyme Assay for Inhibition of HLE:
Enzyme: Purified elastase from human white blood cells.
Substrate: MeO-succinyl-L-alanyl-L-alanyl-L-prolyl-L-valine-p-nitro-anilide (NA).
Reaction Mixture: 10 mM phosphate buffer (pH 7.6), 500 mM NaCl, 10% dimethylsulfoxide (DMSO), 0.35 mM substrate.

The enzyme activity was determined by monitoring the increase in absorbance at 410 nm caused by the hydrolysis of chromogenic substrates. Inhibition of enzyme by the compounds described were determined after a 10 minute preincubation with the enzyme in reaction mixture minus substrate. Reaction was initiated by the addition of substrate. The concentration of human leukocyte elastase used for assay was at 10 nM.

In order to demonstrate the specificity of the compounds of formula I against human leukocyte elastase,

PROTOCOL

Porcine pancreatic Elastase (PPE)
Enzyme: Purified elastase from porcine pancreas
Substrate: MeO-succinyl-L-alanyl-L-alanyl-L-prolyl-L-valine-pNA
Reaction mixture: 50 mM Tris[Tris(hydroxymethyl) aminomethane]. HCl buffer (pH 8.9), 500 mM NaCl, 10% DMSO, 1.4 mM Substrate.
Cathepsin G (CTG)
Enzyme: Purified Cathepsin G from human white blood cells
Substrate: N-succinyl-L-alanyl-L-alanyl-L-phenylalanyl-L-phenylalanine -p-NA.
Reaction mixture: 10 mM Phosphate buffer (pH 7.5), 500 mM NaCl, 10% DMSO, 2.0 mM Substrate.
Trypsin (TRY)
Enzyme: Purified trypsin from bovine pancreas
Substrate: Bz-L-arginine-p-NA
Reaction mixture: 50 mM Tricine[N-Tris(hydroxymethyl)methylglycine]-NaOH buffer (pH 8.8) 150 mM NaCl, 10% DMSO 1.0 mM Substrate.
Thrombin (THR)
Enzyme: Purified thrombin from human plasma Substrate: Tosyl-glycyl-L-prolyl-L-arginine-p-NA acetate
Reaction mixture: 50 mM Tricine-NaOH buffer (pH 8.6), 500 mM NaCl, 0.1% Polyethyleneglycol 8000, 10% DMSO, 0.5 mM Substrate.
Plasmin (PLM)
Enzyme: Purified plasmin from human plasma Substrate: Tosyl-glyclyl-L-prolyl-L-lysine-pNA acetate
Reaction mixture: 50 mM Tris-HCl buffer (pH 8.9), 500 mM NaCl, 5% DMSO, 0.5 mM Substrate.
Cathepsin C (CTC)
Enzyme: Purified cathepsin C from bovine spleen
Substrate: Glycyl-L-phenylalanine-pNA
Reaction mixture: 50 mM Citrate buffer (pH 5.4), 5 mM B-Mercaptoethanol, 150 mM NaCl, 10% DMSO, 20 mM Substrate.
Aminopeptidase M (APM)
Enzyme: Purified aminopeptidase M from porcine kidney
Substrate: L-Leucine-pNA
Reaction Mixture: 50 mM Tricine buffer (pH 7.5), 500 mM NaCl, 10% DMSO, 2.0 mM Substrate.
Cathepsin D (CTD)
Enzyme: Purified cathepsin D from bovine spleen
Substrate: Hemoglobin (bovine)
Reaction mixture: 250 mM Glycine buffer (pH 3.2), 10% DMSO.

Except for Cathepsin D, the enzyme activities were determined by monitoring the increase in absorbance at 410 nm caused by the hydrolysis of chromogenic substrates. The activity of Cathepsin D was determined by monitoring the absorbance of 5% trichloroacetic acid-soluble material at 280 nm.

Inhibition of enzymes by the compounds described were determined after a 10 minute preincubation with enzymes in reaction mixtures minus substrate. Reactions were initiated by the addition of substrates. The concentration used for assays were porcine pancreatic elastase at 240 nM and human Cathepsin G at 50 nM. Cathepsin D was used at the concentration that produced approximately 0.15 O.D. increase per 20 min at 280 nm under the standard conditions. All other proteases were assayed at the concentrations that produced approximately 0.1 O.D. change per minute at 410 nm under the standard conditions.

The compounds which had an $IC_{50}$ value of less than 0.104M for HLE were tested against serine proteases (pancreatic elastase, leukocyte cathepsin G, trypsin, thrombin and plasmin), a cysteine protease (cathepsin C), metalloprotease (aminopeptidase M) and an aspartyl protease (cathepsin D). The results clearly demonstrate the highly selective nature of the inhibition of human leukocyte elastase by these compounds. The specificity of the compounds indicate that they should have little side effects caused by non-specific inhibition of proteases other than HLE when used in the treatment of various ailments in which HLE is the major causative agent.

For therapeutic administration, a compound having the structural formula I is used in the form of conventional pharmaceutical preparation which contains said compounds as an active ingredient in admixture with a pharmaceutically acceptable carrier such as an organic or inorganic solid or liquid excipient which is suitable for oral, parenteral or external administration. The pharmaceutical preparations may be in solid form such as capsule, tablet, ointment, etc. or in liquid form such as solution, suspension or emulsion. There may be included in the above preparation auxiliary substances, stabilizing agents, wetting or emulsifying agents, buffers and the other commonly used additives.

In general, a daily dose of between 0.2 mg and 150 mg or even more per kilogram of body weight per day may be administered to a patient. However, the dose level may vary and will depend upon a variety of factors such as the activity of the specific compound employed, the age, body weight, sex, diet, time of administration, route of administration, etc.

The following examples are provided to demonstrate the operability of the present invention. The structures of the compounds were established by the modes of synthesis, by infrared spectroscopy, and by extensive high field nuclear magnetic resonance spectral techniques and x-ray analysis.

EXAMPLE 1

Benzhydryl 7α-chloro-2-spiro(2',2'-diphenyl) cyclopropyl-3-methyl-3-cephem-4-carboxylate-1,1-dioxide STEP A: Preparation of 7α-chloro-3-methyl-3-cephem-4-carboxylic acid A mixture of 7-ADCA (25 g, 0.117 mol), ethanol (700 ml), water (163 ml) and concentrated hydrochloric acid (163 ml) was cooled to 5° C. Sodium nitrite (11.5 g, 0.167 mol) was added in small portions over 25 minutes and the mixture was stirred for 3.5 hours at 0°-5° C.; 300 ml of brine was added and the reaction mixture was extracted with methylene chloride. The organic extract was washed with water, brine, dried over sodium sulfate and concentrated (16.1 g, 58.9%). This crude acid was directly used for the next step without further purification.

STEP B: Preparation of benzhydryl 7α-chloro-3-methyl-3-cephem-4 carboxylate

The 7α-chloro-3-methyl-3-cephem-4-carboxylic acid (10.0 g, 0.0428 mol) was dissolved in methylene chloride (200 ml), and diphenyldiazomethane (10.8 g, 0.0557 mol) dissolved in methylene chloride (50 ml) was added dropwise over 30 minutes. The mixture was stirred at room temperature for two hours. Solvent was removed under reduced pressure and the product was purified over silica column using hexane-ethyl acetate mixture to yield benzhydryl 7α-chloro-3-methyl-3-cephem-4-carboxylate (7.8 g, 45.6%).

NMR (CDCl$_3$) δ 2.1 (s, 3H, CH$_3$), 3.25 (bs, 2H, H-2), 4.70 (bs, 1H), 4.75 (bs, 1H), 7.0 (s, 1H, CHPh$_2$), 7.3-7.7 (m, 10H, aromatic).

STEP C: Preparation of benzhydryl 7α-chloro-3-methyl-3- cephem-4 carboxylate 1,1-dioxide Benzhydryl 7α-chloro-3-methyl-3-cephem-4-carboxylate (7.6 g, 0.019 mol) was dissolved in methylene chloride (50 ml) and peracetic acid (13.0 g, 0.171 mol),was added dropwise over 15-20 minutes with ice-cooling. The mixture was stirred for 72 hours at room temperature and was then washed successively with portions of water, saturated sodium bicarbonate solution, and water. Drying over sodium sulfate, filtration, removal of the solvent under reduced pressure and filtration of the residue through a small column of silica gel using methylene chloride as eluant gave 9.3 g of benzhydryl 7α-chloro-3-methyl-3-cephem-4-carboxylate 1,1-dioxide as a white foam.

NMR (CDCl$_3$) δ 2.1 (s, 3H, CH$_3$), 3.8 (bs, 2H, H-2), 4.75 (bs, 1H), 5.3 (bs, 1H), 7.0 (s, 1H, CHPh$_2$), 7.4 (bs, 1OH, aromatic).

STEP D: Preparation of benzhydryl 7α-chloro-2-methylene-3-methyl-3-cephem-4-carboxylate 1,1-dioxide Benzhydryl 7α-chloro-3-methyl-3-cephem-4-carboxylate 1,1-dioxide (9.3 g, 0.0215 mol) was dissolved in methylene chloride (35 ml), dimethylamine hydrochloride (4.9 g, 0.0645 mol), formaldehyde solution (2.25 g, 0.075 mol) and t-butyl alcohol (300 ml) were added and the mixture was heated to reflux at 95° C. for 4 hours. After removing the solvent under reduced pressure the residue was redissolved in methylene chloride, washed successively with water, dried over sodium sulfate and concentrated. The product was purified over a silica column using hexane-ethyl acetate mixture as the eluant to yield benzhydryl 7α-chloro-2-methylene-3-methyl-3-cephem-4-carboxylate 1,1-dioxide (3.6 g, 40%) as a white foam. IR (Nujol) $\nu$ max 1723, 1800 cm$-1$.

NMR (CDCl$_3$) $\delta$ 2.01 (s, 3H, CH$_3$), 4.82 (d, 1H, J=1.5 Hz), 5.3 (d, 1H, J=1.5 Hz), 6.12 (d, 1H, exomethylene, J=2.0 Hz), 6.62 (d, 1H, exomethylene, J=2.0 Hz), 6.93 (s, 1H, CHPh$_2$), 7.25–7.39 (m, 10H, aromatic).

STEP E: Preparation of benzhydryl 7α-chloro-2-spiro (2',2'-diphenyl)cyclopropyl-3-methyl-3-cephem-4-carboxylate 1,1-dioxide Benzhydryl 7α-chloro-2-methylene-3-methyl-3-cephem-4-carboxylate 1,1-dioxide (1.0 g, 0.00225 mol) was dissolved in methylene chloride (70 ml) and cooled to $-15°$ C. To this solution diphenyldiazomethane (0.44 g, 0.00225 mol) was added and the mixture was stirred at room temperature for 2 hours, after removing the solvent under reduced pressure the crude product was purified over silica column using gradient elution with hexane-ethyl acetate mixture. IR (Nujol) $\nu$ max 1726, 1791 cm$-1$;

NMR (CDCl$_3$) $\delta$ 1.02 (s,3H, CH$_3$), 2.37 (d, 1H, cyclopropyl, J=7 Hz), 2.97 (d, 1H, cyclopropyl, J=7 Hz), 5.01 (d, 1H, J=1.8 Hz), 5.22 (d, 1H, J=1.8 Hz), 7.0 (s, 1H, CHPh$_2$), 7.28–7.48 (m, 20H, aromatic).

EXAMPLE 2

STEP A: Preparation of 7α-bromo-3-methyl-3-cephem-4-carboxylic acid

To an ice-cooled mixture of 7-ADCA (10.0 g, 0.4667 mol), ethanol (270 ml), water (83 ml) and hydrobromic acid (48%, 56.7 ml), sodium nitrite (4.67 g, 0.6769 mol) was added in small portions over 25 minutes and the mixture was stirred for 2.5 hours at ice-temperature. Ethanol was removed under reduced pressure and the residual mass was diluted with methylene chloride, washed with water. The aqueous washings were saturated with brine and re-extracted with methylene chloride. The combined organic layer was washed with brine, dried over anhydrous sodium sulfate and concentrated to give 9.8 g (75.5%) of 7α-bromo-3-methyl -3-cephem-4-carboxylic acid. This crude acid was directly used for the next step without further purification.

STEP B: Preparation of benzhydryl 7α-bromo-3-methyl-3-cephem-4-carboxylate

To a stirred solution of 7α-bromo-3-methyl-3-cephem-4-carboxylic acid (9.8 g, 0.0353 mol) in 50 ml of dry methylene chloride was added dropwise a solution of diphenyldiazomethane (8.21 g, 0.04228 mol) dissolved in 50 ml of methylene chloride. The mixture was stirred at room temperature for 3 hours, washed with sodium bicarbonate solution, water, brine and concentrated to give 11.91 g (76%) of the crude product as a brown foam.

The above crude product was purified over a silica column with a mixture of hexane-ethyl acetate (85:15) to give 8.02 g (51.2%) of pure benzhydryl 7α-bromo-3-methyl-3-cephem-4-carboxylate.

NMR(CDCl$_3$) $\delta$ 2.15(s, 3H, CH$_3$), 3.29 (bs, 2H, H-2), 4.72(d, 1H), 4.87(d, 1H), 6.99 (s, 1H, CHPh$_2$), 7.25–7.55(m, 10H, aromatic).

STEP C: Preparation of benzhydryl 7α-bromo-3-methyl-3-cephem-4-carboxylate-1,1-dioxide Benzhydryl 7α-bromo-3-methyl-3-cephem-4-carboxylate (16.0 g, 0.036 mol) was dissolved in methylene chloride (75 ml), peracetic acid (24.6 g, 0.324 mol) was added slowly and the mixture was stirred for 72 hours at room temperature, the mixture was washed successively with water, sodium bicarbonate solution and water. Drying over sodium sulfate, filtration, removal of solvent under reduced pressure and purification of the residue over a silica column using methylene chloride as eluant gave benzhydryl 7α-bromo-3-methyl-3-cephem-4-carboxylate 1,1-dioxide (6.7 g, 40%) as a pale yellow foam.

NMR (CDCl$_3$) $\delta$ 2.1(s, 3H, CH$_3$), 3.8(bs, 2H, H-2), 4.8(bs, 1H), 5.25(bs, 1H), 6.95(s, 1H, CHPh$_2$), 7.2–7.6(m, 10H, aromatic).

STEP D: Preparation of benzhydryl 7α-bromo-2-methylene-3-methyl-3-cephem-4-carboxylate-1,1-dioxide To a stirred solution of benzhydryl 7α-bromo-3-methyl-3-cephem-4-carboxylate-1,1-dioxide (2.8 g, 0.0059 mol) in methylene chloride (12 ml) were added dimethylamine hydrochloride (1.44 g, 0.0176 mol), formaldehyde (0.61 g, 0.020 mol) and t-butyl alcohol (100 ml), the mixture was heated to reflux at 95° C. for 3 hours. Solvent was removed under reduced pressure and the residue was dissolved in methylene chloride, washed with water, dried over sodium sulfate and concentrated to dryness. The residue was purified by column chromatography with a solvent gradient of 10 to 25% ethyl acetate/hexane to afford benzhydryl 7α-bromo-2-methylene-3-methyl-3-cephem-4-carboxylate-1, 1-dioxide (2.0 g, 69.5%) as a white foam. IR (Nujol) $\nu$ max 1720, 1800 cm$-1$.

NMR (CDCl$_3$) $\delta$ 2.10 (s, 3H, CH$_3$), 4.93 (d, 1H, J=1.5 Hz), 5.33 (d, 1H, J=1.5 Hz), 6.20 (d, 1H, exomethylene, J=2 Hz), 6.70 (d, 1H, exomethylene, J=2 Hz), 6.98 (s, 1H, CHPh$_2$), 7.30–7.45 (m, 10H, aromatic).

STEP E: Preparation of benzhydryl 7α-bromo-2-spiro(2', 2'-diphenyl) cyclopropyl-3-methyl-3-cephem-4-carboxylate-1,1-dioxide Benzhydryl 7α-bromo-2-methylene-3-methyl-3-cephem-4-carboxylate-1,1-dioxide (0.6 g, 0.00123 mol) was dissolved in methylene chloride (50 ml) and cooled to $-15°$ C., diphenyl diazomethane (0.263 g, 0.00135 mol) was added to the solution and the mixture was stirred at room temperature for 3 hours. Evaporation of the solvent under reduced pressure gave a light pink foam which was purified by column chromatography with a solvent gradient of 10 to 30% ethyl acetate/hexane to afford benzhydryl 7α-bromo-2-spiro-(2',2'-diphenyl)cyclopropyl-3-methyl-3-cephem-4-carboxylate -1,1-dioxide. IR (Nujol) $\nu$ max 1728, 1790 cm$-1$;

NMR (CDCl$_3$) $\delta$ 1.03 (s, 3H, CH$_3$), 2.38 (d, 1H, cyclopropyl, J=7 Hz), 2.96 (d, 1H, cyclopropyl, J=7 Hz), 5.04 (d, 1H, J=1.8 Hz), 5.20 (d, 1H, J=1.8 Hz), 7.0 (s, 1H, CHPH$_2$), 7.22–7.47 (m, 20H, aromatic).

EXAMPLE 3 t-Butyl 7α-bromo-2-spiro(2',2'-diphenyl) cyclopropyl-3-methyl-3-cephem 4-carboxylate-1,1-dioxide STEP A: Preparation of t-butyl 7β-amino-3-methyl-3-cephem-4-carboxylate A mixture of 7-ADCA (10.0 g, 0.0467 mol), ethylene glycol dimethyl ether (80 ml), concentrated sulfuric acid (6.0 ml) and isobutylene (36.0 g, 0.6416 mol) in a pressure bottle was stirred at room temperature for 32 hours. Solvent was removed under reduced pressure. The residue was diluted with methylene chloride, washed with water, sodium bicarbonate solution, brine, dried over sodium sulfate and concentrated to give 4.18 g of t-butyl 7β-amino-3-methyl-3-cephem-4-carboxylate.

NMR (CDCl$_3$) δ 1.55 (s, 9H, t-butyl), 2.07 (s, 3H), 2.25 (bs, 2H, exchanged with D$_2$O), 3.12 (d, 1H, J=18.0 Hz), 3.59 (d, 1H, J=18.0 Hz), 4.70 (d, 1H, J=4.0 Hz), 4.95 (d, 1H, J=4.0 Hz).

STEP B: Preparation of t-butyl 7α-bromo-3-methyl-3-cephem-4-carboxylate

To an ice-cooled mixture of t-butyl 7β-amino-3-methyl-3-cephem-4-carboxylate (1.3 g, 0.0048 mol), ethanol (30 ml), water (8.5 ml), hydrobromic acid (48%, 5.83 ml), sodium nitrite (0.48 g, 0.00696 mol) was added portionwise over 15 minutes and the mixture was stirred at ice-temperature (−5° C.) for 3 hours, saturated with sodium chloride, extracted with ethyl acetate (3 times). The combined ethyl acetate extract was washed with water, brine, dried and concentrated to give 800 mg (50%) of pure t-butyl 7α-bromo-3-methyl-3-cephem-4-carboxylate.

NMR (CDCl$_3$) δ 1.54 (s, 9H, t-butyl), 2.10 (s, 3H), 3.20 (d, 1H, J=18.0 Hz), 3.60 (d, 1H, J=18.0 Hz), 4.71 (d, 1H), 4.85 (d, 1H).

STEP C: Preparation of t-butyl 7α-bromo-3-methyl-3-cephem-4-carboxylate-1,1-dioxide To a solution of t-butyl 7α-bromo-3-methyl-3-cephem-4-carboxylate (800 mg, 2.39 mmol) in methylene chloride (3 ml) was added peracetic acid (32%, 5.12 ml) and the mixture was stirred at room temperature for 48 hours, diluted with methylene chloride, washed with water, brine, dried and concentrated to give 700 mg (80%) of t-butyl 7α-bromo-3-methyl-3-cephem-4-carboxylate 1,1-dioxide. This product was directly used for the next step.

NMR (CDCl$_3$) δ 1.55 (s, 9H, t-butyl), 2.10 (s, 3H), 3.63 (d, 1H, J=18.0 Hz), 3.98 (d, 1H, J=18.0 Hz), 4.83 (d, 1H), 5.33 (d, 1H).

STEP D: Preparation of t-butyl 7α-bromo-2-methylene-3-methyl-3-cephem-4-carboxylate 1,1-dioxide A mixture of t-butyl 7α-bromo-3-methyl-3-cephem-4-carboxylate 1,1-dioxide (700 mg, 1.9 mmol), dimethylamine hydrochloride (460 mg, 5.7 mmol), methylene chloride (3 ml) and t-butyl alcohol (50 ml), formaldehyde (0.57 g, 37% w/v) was heated to reflux at 80°-90° C. for 20 hours. t-Butyl alcohol was removed under reduced pressure and the residue was dissolved in methylene chloride, washed with water, brine, dried and concentrated to give 200 mg of crude product which was purified over silica column using methylene chloride as eluant to give 40 mg of pure t-butyl 7α-bromo-2-methylene-3-methyl-3-cephem-4-carboxylate 1,1-dioxide.

NMR (CDCl$_3$) δ 1.55 (s, 9H, t-butyl), 2.15 (s, 3H), 4.95 (d, 1H), 5.32 (d, 1H), 6.21 (d, 1H), 6.70 (d, 1H).

STEP E: Preparation of t-butyl 7α-bromo-2-spiro(2',2'-diphenyl)-cyclopropyl-3-methyl-3-cephem-4-carboxylate-1,1-dioxide To a solution of t-butyl 7α-bromo-2-methylene-3-methyl-3-cephem-4-carboxylate 1,1-dioxide(40 mg) in 7 ml of methylene chloride was added diphenyldiazomethane (23 mg) and the mixture was stirred at ice-temperature for 3 hours, after removal of the solvent the crude product was purified by preparative tlc to give 30 mg of pure t-butyl 7α-bromo-2-spiro(2',2'-diphenyl)cyclopropyl-3-methyl-3-cephem-4-carboxylate-1,1-dioxide.

NMR (CDCl$_3$) δ 1.10 (s, 3H, CH$_3$), 1.55 (s, 9H, t-butyl), 2.37 (d, 1H, J=7 Hz), 2.96 (d, 1H, J=7 Hz), 5.03 (d, 1H, J=2 Hz), 5.18 (d, 1H, J=2 Hz), 7.23–7.48(m, 10H, aromatic).

EXAMPLE 4 t-Butyl 7α-chloro-2-spiro(2',2'-diphenyl)cyclopropyl-3-acetoxymethyl-3-cephem-4-carboxylate-1,1-dioxide STEP A: Preparation of t-butyl 7β-amino-3-acetoxymethyl-3-cephem-4-carboxylate Dry dioxane was freed from peroxide by passage through a column of neutral activated alumina. To 100 ml of this solvent was added, in turn, with ice-cooling 10 ml of concentrated H$_2$SO$_4$, 10.9 g of 7-ACA and 50 ml of liquid isobutylene. The mixture was sealed in a pressure bottle, stirred at 30° C. for 2 hours, poured into excess of ice-cold aqueous sodium bicarbonate solution. The solution was extracted with ethyl acetate. The combined ethyl acetate extract was washed with brine and dried over sodium sulfate. Evaporation of the filtrate under reduced pressure gave a light brown foam, 8.3 g (63%) of t-butyl 7β-amino-3-acetoxymethyl-3-cephem-4-carboxylate.

NMR (CDCl$_3$) δ 1.5 (s, 9H, t-butyl), 1.8 (bs, 2H, NH$_2$) 2.1 (s, 3H, OCOCH$_3$), 3.45 (ABq, 2H, H-2, J=18 Hz), 4.7–5.2 (m, 4H, H-6+H-7+CH$_2$OCOCH$_3$).

STEP B: Preparation of t-butyl 7β-chloro-3-acetoxymethyl-3-cephem-4-carboxylate

To an ice-cooled solution of t-butyl 7β-amino-3-acetoxymethyl-3-cephem-4-carboxylate (4.0 g, 0.0122 mol) in 75 ml of ethanol, 16.7 ml of water and 16.7 ml of concentrated hydrochloric acid and sodium nitrite (1.18 g, 0.017 mol) were added portionwise over 15–20 minutes. The reaction mixture was stirred at 0°–5° C. for 2.5 hours, saturated with sodium chloride, extracted with methylene chloride, washed with water, brine, dried (Na$_2$SO$_4$) and concentrated to give 3.1 g (73%) of t-butyl 7α-chloro-3-acetoxymethyl-3-cephem-4-carboxylate.

NMR(CDCl$_3$) δ 1.55 (s, 9H, t-butyl), 2.1(s, 3H, OCOCH$_3$), 3.5 (ABq, 2H, H-2, J=18 Hz), 4.6–5.1 (m, 4H, H-6+H-7+CH$_2$OCOCH$_3$).

STEP C: preparation of t-butyl 7α-chloro-3-acetoxymethyl-3-cephem-4-carboxylate-1,1-dioxide To a solution of t-butyl 7α-chloro-3-acetoxymethyl-3-cephem-4-carboxylate (3.1 g) in 50 ml of methylene chloride was added peracetic acid (22 ml) dropwise and the mixture was sitered at room temperature overnight. The reaction mixture was washed with water, sodium bicarbonate solution, brine, dried over anhydrous sodium sulfate, concentrated and the crude product was purified over silica column using hexane-ethyl acetate (3:1) to give 1.9 g (48%) of pure t-butyl 7α-chloro-3-acetoxymethyl-3-cephem-4-carboxylate-1,1-dioxide.

NMR (CDCl$_3$) δ 1.55 (s, 9H, t-butyl), 2.1 (s, 3H, OCOCH$_3$), 3.9 (ABq, 2H, H-2, J=18 Hz), 4.8 (bs, 1H), 4.95 (ABq, 2H, CH$_2$OCOCH$_3$, J=14 Hz), 5.3 (bs, 1H).

STEP D: Preparation of t-butyl 7α-chloro-2-methylene-3-acetoxymethyl-3-cephem-4-carboxylate-1,1-dioxide A mixture of t-butyl 7α-chloro-3-acetoxymethyl-3-cephem-4-carboxylate-1,1-dioxide (1.9 g), methylene chloride (3 ml), dimethylamine hydrochloride (0.817 g), t-butanol (80 ml) and formaldehyde solution (1.10 ml, 37% w/v in water) was heated to reflux at 90° C. for 3 hours. Solvent was removed under reduced pressure and the residue was dissolved in methylene chloride, washed with water, brine, dried and concentrated to give 1.6 g (81.6%) of t-butyl 7α-chloro-2-methylene-3-acetoxymethyl-3-cephem -4-carboxylate-1,1-dioxide, m.p. 148°–149° C. This product without further purification was used in the next step.

STEP E: Preparation of t-butyl 7α-chloro-2-spiro (2',2'-diphenyl)cyclopropyl-3-acetoxymethyl -3-cephem-4-carboxylate-1,1-dioxide To an ice-cooled solution of t-butyl 7α-chloro-2-methylene-3-acetoxymethyl-3-cephem-4-carboxylate-1,1-dioxide (200 mg, 0.51 mmol) in 15 ml of methylene chloride was added a solution of diphenyl diazomethane (109 mg) in 5 ml of methylene chloride and the mixture was stirred at room temperature for 2 hours. After removal of the solvent the crude product was purified by preparative tlc to afford pure t-butyl 7α-chloro-2-spiro-(2',2'-diphenyl)cyclopropyl-3-acetoxymethyl-3-cephem-4-carboxylate-1,1-dioxide (113 mg, 40%), mp. 163°–165° C.

NMR (CDCl$_3$) δ 1.55 (s, 9H, t-butyl), 2.01 (s, 3H, OCOCH$_3$), 2.37 (d, 1H, J=7 Hz), 3.03 (d, 1H, J=7 Hz), 3.12 and 4.08 (dd, 2H, CH$_2$OCOCH$_3$, J=13 Hz), 5.01 (d, 1H, J=2 Hz), 5.26 (d, 1H, J=2 Hz), 7.22–7.48 (m, 10H, aromatic).

EXAMPLE 5

Benzhydryl 7,7-dihydro-2-spiro(2',2'-diphenyl)cyclopropyl -3-methyl-3-cephem-4-carboxylate-1,1-dioxide Following substantially the same procedure as described in Example 1, step E, 0.6 g of benzhydryl 7,7-dihydro-2-methylene-3-methyl-3-cephem-4-carboxylate-1, 1-dioxide in 50 ml of methylene chloride was treated with diphenyldiazomethane to give 0.340 g (39.4%) of benzhydryl 7,7-dihydro-2-spiro(2',2'-diphenyl)cyclopropyl-3-methyl -3-cephem-4-carboxylate-1,1-dioxide. IR (Nujol) ν max 1735, 1786 cm−1.

NMR (CDCl$_3$) δ 1.02 (s, 3H, CH$_3$), 2.34 (d, 1H, cyclopropyl, J=7 Hz), 2.94 (d, 1H, cyclopropyl, J=7 Hz), 3.48 (ABX, 2H, H-7, J=2.5, 5.0, 16.0 Hz) 5.03 (dd, 1H, H-6, J=2.5, 5.0 Hz), 7.0 (s, 1H, CHPh$_2$),7.2–7.48 (m, 20H, aromatic).

EXAMPLE 6

7α Bromo-2-spiro(2',2'-diphenyl)cyclopropyl-3-methyl -3-cephem-4-pyrrolidine carboxamide-1,1-dioxide STEP A: Preparation of 7α-bromo-2-methylene-3-methyl-3-cephem-4-carboxylic acid-1,1-dioxide To an ice-cooled stirred solution of benzhydryl 7α-bromo-2-methylene-3-methyl-3-cephem-4-carboxylate-1, 1-dioxide (from step D, Example 2, 1.0 g, 2.047 mmol) in dry anisole (10 ml) was added trifluoroacetic acid (4.0 ml) and the mixture was stirred at ice-temperature for 1 hour; solvent was removed under reduced pressure to leave a yellow oil. Hexane was added directly to the yellow oil while a white solid was precipitated out which was collected by filtration (0.549 g, 83%).

NMR (CDCl$_3$+DMSO-d$_6$) δ 2.19 (s, 3H, CH$_3$), 5.13 (d, 1H), 5.4' (d,1H), 6.27 (d, 1H), 6.69 (d, 1H).

STEP B: Preparation of 7α-bromo-2-methylene-3-methyl -3-cephem-4-pyrrolidine carboxamide-1,1-dioxide 7α-Bromo-2-methylene-3-methyl-3-cephem-4-carboxylic acid 1,1-dioxide (440 mg, 1.366 mmol) was dissolved in 5 ml of methylene chloride and cooled to −20° C.; to this solution phosphorus oxychloride (0.133 ml, 1.434 mmol) was added over 10 minutes and the mixture was stirred at −20° C. for 30 minutes. Pyrrolidine (0.456 ml, 5.464 mmol) was added and the mixture was stirred at −20° C. for 2 hours. To the mixture ice-water was added and was stirred for 15 minutes, methylene chloride layer was separated out and the aqueous layer was re-extracted with methylene chloride, the combined methylene chloride layer was washed with water, citric acid, brine, dried over anhydrous sodium sulfate and concentrated to give 400 mg (78%) of brown solid which was purified over silica column using ethyl acetate-acetonitrile (9:1) as eluant; Pure product (89 mg, 17.4%) was isolated as white solid.

NMR (CDCl$_3$) δ 1.92 (s, 3H, CH$_3$), 1.85–2.1 (m, 4H, pyrrolidine), 3.42–3.73 (m, 4H, pyrrolidine), 4.98 (d, 1H, J=1.6 Hz), 5.37 (d, 1H, J=1.6 Hz), 6.0 (d, 1H, J=1.8 Hz), 6.54 (d, 1H, J=1.8 Hz).

STEP C: Preparation of 7α-bromo-2-spiro(2',2'-diphenyl cyclopropyl-3-methyl-3-cephem-4-pyrrolidine carboxamide-1,1-dioxide To an ice-cooled solution of 7α-bromo-2-methylene-3-methyl-3-cephem-4-pyrrolidine carboxamide-1,1-dioxide (60 mg, 0.1599 mmol) in 3 ml of methylene chloride was added diphenyl diazomethane (31 mg, 0.1599 mmol). The reaction mixture was stirred at ice-temperature for 1.5 hours and then concentrated to give 80 mg of the crude product which was purified by preparative tlc (30 mg, 35%).

NMR (CDCl$_3$) δ 0.93 (s, 3H, CH$_3$), 1.86–2.0 (m, 4H, pyrrolidine), 2.275 (d, 1H, J=7.0 Hz, cyclopropyl), 2.94 (d, 1H, J=7.0 Hz, cyclopropyl), 3.42–3.68 (m, 4H, pyrrolidine), 5.03 (d, 1H, J=1.6 Hz), 5.20(d, 1H, J=1.6 Hz), 7.18–7.49 (m, 10H, aromatic).

EXAMPLE 7

2,2,2-Trichloroethyl-7α-ethoxy-2-spiro(2',2'-diphenyl)-cyclo -propyl-3-methyl-3-cephem-4-carboxylate-1,1-dioxide STEP A: Preparation of 2,2,2-trichloroethyl-6α-ethoxy-2, 2-dimethyl penicillanate To an ice-cooled solution of 6-diazopenicillanate (5.0 g, 0.01395 mol) in a mixture of ethanol (10 ml) and methylene chloride (20 ml) was added boron trifluoroetherate (4 drops). The mixture was stirred at ice-temperature for 3 hours, washed with water, brine, dried and concentrated to give 4.56 g (87%) of crude product which was purified over silica column using hexane-ethyl acetate (4:1) as eluant. The yield of pure product was 3.4 g (54.1%).

NMR (CDCl$_3$) δ 1.25 (t, 3H), 1.55 (s, 3H), 1.6 (s, 3H), 3.75 (q, 2H), 4.65 (s, 2H), 4.8 (s, 2H), 5.30 (s, 1H).

STEP B: Preparation of 2,2,2-trichloroethyl-6α-ethoxy-2, 2-dimethyl penicillanate 1-oxide To an ice-cooled solution of 2,2,2-trichloroethyl-6α-ethoxy-2, 2-dimethyl penicillanate (3.4 g, 9.026 mmol) in 40 ml of methylene chloride was added m-chloroperbenzoic acid (80%, 1.95 g, 9.026 mmol) portionwise over 30 minutes. The mixture was stirred at ice-temperature until tlc indicates that all starting material has been consumed. The reaction mixture was washed with sodium bicarbonate solution, water, brine, dried and concentrated to give 4.0 g of crude product which was purified over silica column using methylene chloride as eluant (3.0 g, 84%).

NMR (CDCl$_3$) δ 1.3 (t, 3H), 1.34 (s, 3H), 1.80 (s, 3H), 2.85 (q, 2H) 4.65 (s, 1H), 4.80 (s, 1H), 5.02 (s, 3H).

STEP C: Preparation of 2,2,2-trichloroethyl-7α-ethoxy-3-methyl-3-cephem-4-carboxylate A solution of 2,2,2-trichloroethyl-6α-ethoxy-2, 2-dimethylpenicillanate 1-oxide (1.0 g, 2.546 mmol) in a mixture of DMF (10 ml) and acetic anhydride (0.659 ml) was heated to reflux at 125°-1300° C. for 1.5 hours. Solvent was removed under reduced pressure and the residual dark oil was diluted with methylene chloride and was washed successively with water, sodium bicarbonate solution, brine, dried and concentrated to give 910 mg of the crude product which was purified on a silica column using methylene chloride as eluant, yield (400 mg, 42%).

NMR (CDCl$_3$) δ 1.28 (t, 3H), 2.165 (s, 3H), 3.215 (d, 1H, J=17.3 Hz), 3.51 (d, 1H, J=17.3 Hz), 3.62-3.88 (m, 2H), 4.57 (d, 1H, J=1.4 Hz), 4.72 (d, 1H, J=1.4 Hz), 4.80 (d, 1H, J=12 Hz), 5.06 (d, 1H, J=12 Hz).

STEP D: Preparation of 2,2,2-trichloroethyl-7α-ethoxy-3-methyl-3-cephem-4-carboxylate-1,1-dioxide To an ice-cooled solution of 2,2,2-trichloroethyl -7α-ethoxy-3-methyl-3-cephem-4-carboxylate (340 mg, 0.9075 mmol) in methylene chloride (14 ml), peracetic acid (32%, 1.94 ml) was added dropwise and the mixture was stirred at room temperature for 24 hours; ice-cold water was added to the reaction mixture and the organic layer was separated out; the aqueous solution was saturated with solid sodium chloride and re-extracted with methylene chloride. The combined organic layer was washed with sodium bicarbonate solution, water, brine, dried over anhydrous sodium sulfate and concentrated to give 370 mg of the crude product which was purified over silica column using hexane-ethyl acetate (4:1) mixture, yield (300 mg, 81%).

NMR (CDCl$_3$) δ 1.29 (t, 3H), 2.16 (s, 3H), 3.68 (d, 1H, J=18.0 Hz), 3.92 (d, 1H, J=18 Hz), 3.67-3.96 (m, 2H), 4.67 (bs, 1H), 4.83 (d, 1H, J=11.7 Hz), 5.035 (d, 1H, J=11.7 Hz), 5.22 (d, 1H, J=1.4 Hz).

STEP E: Preparation of 2,2,2-trichloroethyl-7α-ethoxy -2-methylene-3-methyl-3-cephem-4-carboxylate -1,1-dioxide 2,2,2-Trichloroethyl 7α-ethoxy-3-methyl-3-cephem-4-carboxylate 1,1-dioxide (290 mg, 0.7131 mmol) was dissolved in methylene chloride (5 ml), dimethylamine hydrochloride (168 mg, 2.066 mmol), formaldehyde solution (0.19 ml, 2.375 mmol, 37% w/v) and t-butyl alcohol (3.3 ml) was heated to reflux at 70°-75° C. for 1.5 hours; solvent was removed under reduced pressure, the residue was diluted with methylene chloride and washed with water, brine, dried and concentrated to give 300 mg of white solid which was directly used for the next step without further purification.

NMR (CDCl$_3$) δ 1.30 (t, 3H), 2.19 (s, 3H), 3.67-3.89 (m, 2H), 4.805 (d, 1H, J=11.8 Hz), 5.12 (d, 1H, J=11.8 Hz), 4.86 (d, 1H), 5.32 (d, 1H), 6.17 (d, 1H, J=2.0 Hz), 6.68 (d, 1H, J=2.0 Hz).

STEP F: Preparation of 2,2,2-Trichloroethyl-7α-ethoxy-2-spiro(2',2'-diphenyl)cyclopropyl-3-methyl-3- cephem-4-carboxylate-1,1-dioxide To an ice-cooled solution of 2,2,2-trichloroethyl -7α-ethoxy-2-methylene-3-methyl-3-cephem-4-carboxylate 1,1-dioxide (100 mg, 0.2388 mmol) in methylene chloride (5 ml) was added diphenyldiazomethane (56 mg, 0.2866 mmol) and the mixture was stirred at ice-temperature for 2 hours; solvent was removed under reduced pressure and the crude product was purified over silica column using methylene chloride as eluant to give 68 mg of pure 2,2,2-trichloroethyl-7α-ethoxy-2-spiro (2',2'-diphenyl) cyclopropyl-3-methyl-3-cephem-4-carboxylate -1,1-dioxide.

NMR (CDCl$_3$) δ 1.16 (s, 3H, CH$_3$), 1.22 (t, 3H), 2.38 (d, 1H, J=7.0 Hz, cyclopropyl), 2.98 (d, 1H, J=7.0 Hz, cyclopropyl), 3.46-3.82 (m, 2H), 4.67 (d, 1H, J=11.7 Hz), 5.02 (d, 1H), 5.11 (d, 1H), 5.24 (d, 1H, J=11.7 Hz), 7.17-7.50 (m, 10H, aromatic).

EXAMPLE 8

2,2,2-Trichloroethyl-7α-methoxy-2-spiro(2',2'-diphenyl) cyclopropyl-3-methyl-3-cephem-4-carboxylate-1,1-dioxide STEP A: Preparation of 2,2,2-trichloroethyl-6α-methoxy-2, 2-dimethyl penicillanate To an ice-cooled solution of 6-diazopenicillanate (5.0 g, 0.01395 mol) in a mixture of methanol (25 ml) and methylene chloride (25 ml) was added boron trifluoro etherate (4-5 drops) and the mixture was stirred at ice-temperature for 2 hours, washed with water, brine dried and concentrated to give 3.4 g of crude product which was purified over silica column using hexane-ethyl acetate (3:2) as eluant to give 2.3 g of pure 2,2,2-trichloroethyl-6α-methoxy-2,2-dimethyl penicillanate.

NMR (CDCl$_3$) δ 1.55 (s, 3H), 1.61 (s, 3H), 3.55 (s, 3H, OCH$_3$), 4.625 (doublet overlapped with a singlet, 2H), 4.79 (d, 2H), 5.35 (d, 1H).

STEP B: Preparation of 2,2,2-trichloroethyl-6α-methoxy-2,2-dimethyl penicillanate-1-oxide To an ice-cooled solution of 2,2,2-trichloroethyl-6α-methoxy-2,2-dimethyl penicillanate (35.6 g, 0.09816 mol) in methylene chloride (350 ml) was added dropwise peracetic acid (15.4 ml, 32%). The mixture was stirred at ice-temperature for one hour, washed with water, sodium bicarbonate solution, brine, dried over anhydrous sodium sulfate and concentrated to give 26.0 g of 2,2,2-trichloroethyl-6α-methoxy-2,2-dimethyl penicillanate-1-oxide.

NMR (CDCl$_3$) δ 1.34 (s, 3H), 1.75 (s, 3H), 3.58 (s, 3H, OCH$_3$), 4.60 (s, 1H), 4.96 (s, 2H), 4.63 (d, 1H, J=12.0 Hz), 5.03 (d, 1H, J=12.0 Hz).

STEP C: Preparation of 2,2,2-trichloroethyl-2-(benzothiazol-2'-yldithio)-α-isopropenyl-4-oxo-3α-methoxy azetidine-1-acetate A mixture of 2,2,2-trichloroethyl-6α-methoxy-2, 2-dimethyl penicillanate-1-oxide (15.0 g, 0.0396 mol) and 2-mercaptobenzothiazole (7.44 g, 0.04357 mol) in 250 ml of dry toluene was heated to reflux for 2 hours using a Dean-Stark trap; solvent was removed under reduced pressure. The residual brown oil was dissolved in methylene chloride and precipitated with hexane under ice-cooling. The precipitated solid (18.4 g, 86%) was collected by filtration and used for the next step.

STEP D: Preparation of 2,2,2-trichloroethyl-6α-methoxy-2β-bromomethyl-2α-methyl penicillanate 2,2,2-Trichloroethyl-2-(benzothiazol-2'-yldithio)-α-isopropenyl-4-oxo-3α-methoxy azetidine-1-acetate (7.4 g, 0.01408 mol) was dissolved in methylene chloride (100 ml) and cooled to −30° C.; bromine (0.431 ml, 0.0084 mol) dissolved in methylene chloride was added dropwise to the above solution and the mixture was stirred at −30° C. for 40 minutes, the precipitated solid was filtered through a Celite pad. The filtrate was concentrated under reduced pressure. The residual mass was redissolved in ether and cooled, the precipitated solid was filtered off. The filtrate was concentrated to give a foam (6.0 gm). This product was used in the next step.

NMR (CDCl$_3$) δ 1.67 (s, 3H), 3.55 (s, 5H, OCH$_3$+CH$_2$Br), 4.67 (s, 1H), 4.80 (s, 2H), 5.30 (s, 1H), 5.45 (s, 1H).

STEP E: Preparation of 2,2,2-trichloroethyl-7α-methoxy -3-methyl-3-cephem-4-carboxylate The crude mass (6.0 gm) from Step D was dissolved in a mixture of dimethyl sulfoxide (100 ml) and pyridine (9.0 ml) and the reaction mixture was stirred at room temperature for 20 hours; solvent was removed under reduced pressure. The sticky mass was dissolved in methylene chloride, washed successively with water, dilute hydrochloric acid, brine, dried and concentrated to give a semi solid (5.0 g).

NMR (CDCl$_3$) δ 2.15 (s, 3H), 3.37 (d, 2H), 3.55 (s, 3H), 4.58 (s, 1H), 4.77 (s, 2H), 4.90 (s, 1H).

STEP F: Preparation of 2,2,2-trichloroethyl-7α-methoxy-3-methyl-3-cephem-4-carboxylate-1,1-dioxide 2,2,2-Trichloroethyl-7α-methoxy-3-methyl-3-cephem-4-carboxylate (8.7 g, 24.12 mmol) was dissolved in 100 ml of methylene chloride, peracetic acid (51.6 ml) was added dropwise and the mixture was stirred at room temperature for 18 hours. After the reaction, the reaction mixture was washed with water, sodium bicarbonate solution, brine, dried and concentrated to give a sticky solid. To the sticky mass a mixture of ether: hexane (1:1) was added with ice-cooling. The precipitated solid was collected by filtration (9.33 g, 98.5%). NMR (CDCl$_3$) δ 2.17 (s, 3H), 3.57 (s, 3H), 4.13 (d, 2H), 4.93 (s, 1H), 5.15 (d, 1H), 5.20 (s, 1H), 5.96 (d, 1H).

STEP G: Preparation of 2,2,2-trichloroethyl-7α-methoxy -2-methylene-3-methyl-3-cephem-4-carboxylate-1,1-dioxide A mixture of 2,2,2-trichloroethyl-7α-methoxy-3-methyl -3-cephem-4-carboxylate-1,1-dioxide (2.0 g, 5.094 mmol), dimethylamine hydrochloride (1.24 g, 15.28 mmol), t-BuOH (24 ml), methylene chloride (5 ml) and formaldehyde (1.43 ml, 37% w/v in water) was heated to reflux at 80° C. for 1.5 hours. The solvent was removed under reduced pressure and the residual mass was dissolved in methylene chloride, washed successively with water, dried and concentrated to give 1.78 gm (86.4%) of pure 2,2,2-trichloroethyl-7α-methoxy-2-methylene-3-methyl -3-cephem-4-carboxylate-1,1-dioxide as a white solid.

NMR (CDCl$_3$) δ 2.20 (s, 3H), 3.60 (s, 3H), 4.80 (d, 1H, J=14 Hz), 4.90 (bs, 1H), 5.20 (d, 1H, J=14 Hz), 5.30 (bs, 1H), 6.23 (d, 1H), 6.75 (d, 1H).

STEP H: Preparation of 2,2,2-trichloroethyl-7α-methoxy-2-spiro (2',2'-diphenyl) cyclopropyl-3-methyl-3-cephem-4-carboxylate 1,1-dioxide 2,2,2-Trichloroethyl-7α-methoxy-2-methylene-3-methyl-3-cephem-4-carboxylate-1,1-dioxide (1.78 g, 4.399 mmol) was dissolved in methylene chloride (70 ml). To this solution diphenyl diazomethane (0.940 g, 4.839 mmol) was added and the mixture was stirred at room temperature for 3 hours. After removal of the solvent the pink foam was purified over silica column using methylene chloride as eluant; 900 mg (35.8%).

NMR (CDCl$_3$) δ 2.16 (s, 3H), 2.40 (d, 1H, J=7.0 Hz), 3.0 (d, 1H, J=7.0 Hz), 3.47 (s, 3H), 4.68 (d, 1H, J=12 Hz), 5.02 (d, 1H), 5.07 (d, 1H), 5.23 (d, 1H, J=12 Hz).

EXAMPLE 9

Benzhydryl 7α-methoxy-2-spiro (2',2'-diphenyl) cyclopropyl-3-methyl-3-cephem-4- carboxylate-1,1-dioxide STEP A: Preparation of 7α-methoxy-2-spiro (2',2'-diphenyl) cyclopropyl-3-methyl-3-cephem-4-carboxylic acid-1,1-dioxide 2,2,2-Trichloroethyl 7α-methoxy-2-spiro (2',2'-diphenyl) cyclopropyl-3-methyl-3-cephem-4-carboxylate-1,1-dioxide (from Step H, Example 8, 2.39 g, 4.187 mmol) was dissolved in 50 ml of glacial acetic acid, zinc powder(7.0 g) was added and the mixture was stirred at room temperature for 1 hour, excess zinc was removed by filtration through a bed of Celite. The filtrate was concentrated under reduced pressure. The residue was dissolved in ethyl acetate, washed with water, brine, dried and concentrated to give 1.5 g (83%) of pure acid.

NMR (CDCl$_3$) δ 1.23 (s, 3H), 2.38 (d, 1H, J=6.8 Hz), 2.94 (d, 1H, J=6.8 Hz), 3.47 (s, 3H), 5.026 (bs, 1H), 5.054 (bs, 1H), 7.24–7.49 (m, 10 H, aromatic).

STEP B: Preparation of benzhydryl 7α-methoxy-2-spiro (2',2'-diphenyl)cyclopropyl-3-methyl-3-cephem-4-carboxylate-1,1-dioxide To a stirred solution of 7α-methoxy-2-spiro (2',2'-diphenyl)cyclopropyl-3-methyl-3-cephem-4-carboxylic acid-1,1-dioxide (830 mg, 1.889 mmol) in 20 ml of methylene chloride was added diphenyl diazomethane (367 mg, 1.889 mmol) and the mixture was stirred at room temperature for 3 hours, washed with dilute sodium bicarbonate solution, brine, dried and concentrated to give 1.3 g of the crude product which was purified over silica column using methylene chloride as eluant to give 362 mg of pure benzhydryl 7α-methoxy-2-spiro(2',2'-diphenyl)cyclopropyl-3-methyl-3-cephem-4-carboxylate-1,1-dioxide.

NMR (CDCl$_3$) δ 0.96 (s, 3H), 2.31 (d, 1H, J=6.9 Hz), 2.92 (d, 1H, J=6.9 Hz), 3.44 (s, 3H), 4.95 (d, 1H, J=1.5 Hz), 5.05 (d, 1H, J=1.5 Hz), 7.01 (s, 1H), 7.2–7.47 (m, 20 H, aromatic).

EXAMPLE 10

7α-Methoxy-2-spiro (2',2'-diphenyl)cyclopropyl-3-methyl-3-cephem-4-pyrrolidine carboxamide-1,1-dioxide 7α-Methoxy-2-spiro (2',2'-diphenyl)cyclopropyl-3-methyl-3-cephem-4-carboxylic acid-1,1-dioxide (1.84 g, 4.187 mmol, from Step A, Example 9) was dissolved in 45 ml of methylene chloride, oxalyl chloride (797 mg, 6.280 mmol) was added followed by a drop of N,N-dimethyl formamide. The mixture was stirred at room temperature for one hour. Solvent was removed under reduced pressure and the light brown solid was dried under high vacuum.

The solid was redissolved in dry methylene chloride (15 ml), cooled in an ice-bath, and a solution of pyrrolidine (596 mg, 8.374 mmol) in dry methylene chloride (8 ml) was added dropwise. The mixture was stirred at ice-temperature for 1 hour, washed with cold water, dilute hydrochloric acid, water, brine, dried and concentrated to give 1.57 g of the crude product which was purified over a silica column using hexane-ethyl acetate (1:1) as eluant to give pure, 1.04 (50.5%), 7α-methoxy-2-spiro(2',2'-diphenyl) cyclopropyl-3-methyl-3-cephem-4- pyrrolidinecarboxamide-1, 1-dioxide; crystallization from ether gave a pale yellow solid, mp. 222° C. (decomposed).

NMR (CDCl$_3$) δ 0.92 (s, 3H), 1.71-2.04 (m, 4H, pyrrolidine), 2.23 (d, 1H, J=6.7 Hz), 2.91 (d, 1H, J=6.7 Hz), 3.09-3.68 (m, 4H, pyrrolidine), 3.46 (s, 3H), 4.94 (d, 1H, J=1.5 Hz), 5.05 (d, 1H, J=1.5 Hz), 7.17-7.50 (m, 10H, aromatic).

EXAMPLE 11

7α-Methoxy-2-spiro (2',2'-diphenyl)cyclopropyl-3-methyl-3-cephem-4-piperidine carboxamide-1,1-dioxide 7α-Methoxy-2-spiro (2',2'-diphenyl)cyclopropyl-3-methyl-3-cephem-4-carboxylic acid-1,1-dioxide (1.0 g, 2.275 mmol, from Step A, Example 9) was dissolved in 5 ml of methylene chloride, oxalyl chloride (0.3 ml, 3.413 mmol) was added followed by a drop of N,N-dimethyl formamide. The mixture was stirred at room temperature for one hour. Solvent was removed under reduced pressure.

The light brown solid was redissolved in dry methylene chloride (5 ml), cooled in an ice-bath, piperidine (388 mg, 4.551 mmol) dissolved in 5 ml of dry methylene chloride was added dropwise and the reaction mixture was stirred at ice-temperature for 2 hours, washed with water, brine, dried and concentrated to give 980 mg of crude product which was purified on a silica column using hexane ethyl acetate (2:1) as eluant to give 491 mg (42.6%) of pure 7α-methoxy-2-spiro (2',2'-diphenyl)cyclopropyl-3-methyl -3-cephem-4-piperidine carboxamide-1,1-dioxide.

NMR (CDCl$_3$) δ 0.903 (s, 3H), 1.46-1.68 (m, 6H, piperidyl), 2.23 (d, 1H, J=6.8 Hz), 2.91 (d, 1H, J=6.8 Hz), 3.34-3.64 (m, 4H, piperidyl), 3.459 (s, 3H, OCH$_3$), 4.95 (d, 1H, J=1.5 Hz), 5.04 (d, 1H, J=1.5 Hz), 7.20-7.50 (m, 10H, aromatic).

EXAMPLE 12

Benzhydryl 7α-bromo-2-spiro [2',2'-(4',4'-dichloro) diphenyl]cyclopropyl-3-methyl-3-cephem-4-carboxylate-1,1-dioxide STEP A: Preparation of di(4-chlorophenyl)diazomethane To a stirred ice-cold solution of 4,4'-dichlorobenzophenone hydrazone (1.303 g) in dry methylene chloride (20 ml) was added magnesium sulfate (590 mg), silver oxide (1.196 g) was added in one portion followed by potassium carbonate (30 mg). The mixture was stirred at ice-temperature for 1 hour, then at room temperature for an additional hour, filtered through Celite to give a dark purple solution which was directly used for the cycloaddition reaction.

STEP B: Preparation of benzhydryl 7α-bromo-2-spiro [2',2'-(4',4'-dichloro)diphenyl] cyclopropyl-3-methyl-3-cephem-4-carboxylate-1,1-dioxide Benzhydryl 7α-bromo-2-methylene-3-methyl-3-cephem-4-carboxylate-1,1-dioxide (2.0 g, from Step D, Example 2) was dissolved in dry methylene chloride (30 ml) and cooled in an ice-bath. To this solution di(4-chlorophenyl) diazomethane (from Step A) was added and the mixture was stirred at ice-temperature for 1 hour. Evaporation of the solvent and purification over a silica column using hexane ethyl acetate mixture as eluant pure benzhydryl 7α-bromo-2-spiro [2',2'-(4',4'-dichloro)diphenyl] cyclopropyl-3-methyl-3-cephem-4-carboxylate-1,1-dioxide (1.2 g) was obtained, m.p. 202° C. (decomp.).

NMR (CDCl$_3$) δ 1.03 (s, 3H), 2.32 (d, 1H, J=7 Hz), 2.90 (d, 1H, J=7 Hz), 4.94 (d, 1 H, J=1,5 Hz), 5.23 (d, 1H, J=1.5 HZ), 7.03 (s, 1H, CHPh$_2$), 7.18-7.42 (m, 18H, aromatic).

EXAMPLE 13

Benzhydryl 7α-bromo-2-spiro[2',2'-(4',4'-difluoro)-diphenyl] cyclopropyl-3-methyl-3-cephem-4-carboxylate-1,1-dioxide STEP A: Preparation of di(4-fluorophenyl)diazomethane 4,4'-Difluorobenzophenone (1.0 g, 4.306 mmol) was dissolved in methylene chloride (9 ml) containing iodine (0.2 ml; 1% w/v) and 1,1,3,3-tetramethyl guanidine (2.1 ml). To this solution was added peracetic acid solution (1.23 ml, 6.459 mmol) at 0° C. over 20 minutes. The mixture was stirred at 0° C. for 1 hour, then washed with water until the washings were at pH 6. The methylene chloride layer was dried over anhydrous sodium sulfate and concentrated to give a deep purple oil (850 mg, 83.7%) which was directly utilized for the next reaction.

STEP B: Preparation of benzhydryl 7α-bromo-2-spiro [2',2'-(4',4'-difluoro)diphenyl]cyclopropyl -3-methyl-3-cephem-4-carboxylate-1,1-dioxide Benzhydryl 7α-bromo-2-methylene-3-methyl-3-cephem-4-carboxylate-1,1-dioxide (1.6 g, from step D, Example 2) was dissolved in dry methylene chloride (20 ml) and cooled in an ice-bath. To this solution di (4-fluorophenyl) diazomethane (from step A) was added and the mixture was stirred at ice-temperature for 1 hour. Evaporation of the solvent and purification over a silica column using hexaneethyl acetate mixture as eluant, pure benzhydryl 7α-bromo-2-spiro[2',2'-(4',4'-difluoro) diphenyl]cyclopropyl-3-methyl-3-cephem-4-carboxylate-1, 1-dioxide (0.8 g) was obtained.

NMR (CDCl$_3$) δ 1.04 (s, 3H), 2.33 (d, 1H, J=7.2 Hz), 2.92 (d, 1H, J=7.2 Hz), 4.92 (d, 1H, J=1.5 Hz), 5.22 (d, 1H, J=1.5 Hz), 6.88-7.44 (m, 18H, aromatic).

Following the procedure described in Example 13, Step B but starting with an appropriate diazo compound the following cyclopropyl derivatives were prepared:

(1) Benzhydryl 7α-bromo-2-spiro(2'-ethoxycarbonyl)cyclopropyl-3-methyl-3-cephem-4-carboxylate-1,1-dioxide, NMR (CDCl$_3$) δ 1.23 (t, 3H, COOCH$_2$CH$_3$), 1.80 (s, 3H, CH$_3$), 2.18 (d, 2H, cyclopropyl, J=8.5 Hz), 2.75 (t, 1H, CHCOOCH$_2$CH$_3$, J=8.5 Hz), 4.17 (q, 2H, COOCH$_2$CH$_3$), 5.08 (d, 1H, J=1.5 Hz), 5.26 (d, 1H, J=1.5 Hz), 6.98 (s, 1H, CHPh$_2$), 7.26-7.37 (m, 10 H, aromatic).

(2) Benzhydryl 7α-bromo-2-spiro(2'-phenyl-2'-methyl) cyclopropyl-3-methyl-3-cephem-4-carboxylate-1,1-dioxide.

NMR (CDCl$_3$) δ 0.92 (s, 3H, CH$_3$), 1.78 (s, 3H, CH$_3$), 2.23 (ABq, 2H, cyclopropyl, J=7 Hz), 5.03 (d, 1H, J=1.7 Hz), 5.34 (d, 1H, J=1.7 Hz), 6.9 (s, 1H, CHPh$_2$), 7.18-7.48 (m, 15H, aromatic).

(3) Benzhydryl 7α-bromo-2-spiro(2'-phenyl)cyclopropyl-3-methyl-3-cephem-4-carboxylate-1,1-dioxide.

NMR (CDCl$_3$) δ 1.07 (s, 3H, CH$_3$), 2.09 (dd, 1H, cyclopropyl, J=6.8 Hz and 8.0 Hz), 2.39 (dd, 1H, cyclopropyl, J=6.8 Hz and 8.0 Hz), 3.29 (dd, 1H, cyclopropyl, J=8.0 Hz and 10.0 Hz), 5.16 (d, 1H, J=1.4 Hz), 5.45 (d, 1 H, J=1.4 Hz), 6.90 (s, 1H, CHPh$_2$), 7.22-7.36 (m, 15H, aromatic).

EXAMPLE 14

Benzhydryl 7α-methoxy-2-spiro (2',2'-diphenyl) cyclopropyl 3-[(1, 2, 3-triazolyl)methyl]-3- cephem-4-carboxylate-1,1-dioxide STEP A: Preparation of 7β-amino-3-azidomethyl 3-cephem-4-carboxylic acid To 7β-amino-3-acetoxymethyl-3-cephem-4-carboxylic acid (27.2 g, 99.9 mmol) was added water (500 ml) and sodium bicarbonate (9.3 g, 111 mmol); the pH of the mixture was adjusted to 6.5 with 10% sodium hydroxide solution. Sodium azide (13.1 g, 201 mmol) was added to the mixture followed by acetone (350 ml). The mixture was heated at 60° C. for 6 h and left stirring at room temperature overnight. Acetone was removed under reduced pressure and the mixture was cooled in an ice-bath, acidified with concentrated hydrochloric acid to pH 3.5; the precipitated solid was filtered off, dried overnight over $P_2O_5$ to give 14.3 g (56%) of 7β-amino-3-azidomethyl-3-cephem-4-carboxylic acid. IR (Nujol) ν max 2095, 1796, 1732 cm−1.

STEP B: Preparation of benzhydryl 7β-amino-3-azidomethyl-3-cephem-4-carboxylate

To a suspension of 7β-amino-3-azidomethyl-3-cephem-4-carboxylic acid (20.7 g, 81 mmol) in a mixture of dichloromethane (250 ml) and dimethyl sulfoxide (250 ml) was added dropwise a solution of diphenyldiazomethane (17.53 g, 90 mmol) in dichloromethane (150 ml). The mixture was stirred at room temperature for 68 h, filtered, the filtrate was concentrated under reduced pressure. The residual sticky mass was taken in ethyl acetate (250 ml) and washed successively with saturated sodium bicarbonate solution, water, brine, dried over anhydrous sodium sulfate; solvent was removed under reduced pressure to give a residue which was purified over a silica column using dichloromethane-ethyl acetate (1:1) to give 18.4 g (54%) of a mixture of $\Delta^2$ and $\Delta^3$-cephems. The mixture was directly used for the next step without further separation.

STEP C: Preparation of benzhydrvl 7β-amino-3-azidomethyl-3-cephem-4-carboxylate-1, 1-dioxide To a stirred solution of the isomeric mixture of $\Delta^2$ and & $\Delta^3$-cephems (from the step B, Example 14) (16 g, 38 mmol) in ethyl acetate (500 ml) at 0° C. was added sodium tungstate dihydrate (1.254 g, 3.8 mmol) and hydrogen peroxide (30% solution, 17.5 ml). After stirring at 0° C. for 15 min, the mixture was stirred at room temperature for 2 h when another batch of hydrogen peroxide (4.4 ml) was added and the resulting mixture was stirred overnight. The mixture was cooled in an ice-bath and sodium bisulfite solution (13 g in 100 ml of water) was added dropwise and the mixture was stirred for 10 min. Sodium carbonate solution (4 g in 80 ml of water) was added and the mixture was stirred for 10 min. Ethyl acetate layer was separated out, the aqueous layer was re-extracted with two portions of ethyl acetate. The combined ethyl acetate layer was washed with brine, dried ($Na_2SO_4$) and concentrated under reduced pressure. To the residue hexane was added and the mixture was stirred with ice-cooling. The precipitated solid was collected by filtration to give 12.2 g (71%) of pure benzhydryl 7β-amino-3-azidomethyl-3-cephem-4-carboxylate-1, 1-dioxide. IR (Nujol) ν max 2085, 1783, 1715 cm−1.

NMR ($CDCl_3$) δ 2.35 (br, s, 2H), 3.7 and 4.01 (ABq, 2H, J=18 Hz), 4.25 (br, s, 2H), 4.8 (d, 1H, J=5 Hz), 4.95 (d, 1H, J=5 Hz), 7.05 (s, 1H,), 7.4–7.65 (m, 10 H)

STEP D: Preparation of benzhydryl 7α-methoxy-3-azidomethyl 3-cephem-4-carboxylate-1, 1-dioxide To an ice-cooled stirred solution of benzhydryl 7β-amino-3-azidomethyl-3-cephem-4-carboxylate-1, 1-dioxide (1.1 g, 2.43 mmol) in dichloromethane (15 ml) was added an ice-cold solution of sodium nitrite (184 mg, 2.67 mmol) in water (9 ml); 2.5 (N) sulfuric acid (1.1 ml) was added dropwise at such a rate that the temperature was below 0° C. The mixture was stirred at 0° C. for 1 h; the dichloromethane layer was separated out and the aqueous layer was re-extracted with dichloromethane (2×20 ml). The combined organic layer was washed with water (25 ml), brine (40 ml), dried ($Na_2SO_4$), filtered. To the filtrate, methanol (25 ml) was added and while stirring at room temperature, rhodium acetate dimer (12 mg) was added in one portion. After 1 h stirring at room temperature, the reaction mixture was filtered through Celite and solvent was removed under reduced pressure. The residue was purified by silica column using hexane-ethyl acetate mixture (3:2) as eluant to give 370 mg (33%) of pure benzhydryl 7α-methoxy-3-azidomethyl-3-cephem-4-carboxylate-1,1-dioxide, m.p. 160°–161° C. (from ether-hexane). IR (Nujol) ν max 2090, 1791, 1716 cm−1.

NMR ($CDCl_3$) δ 3.56 (s, 3H), 3.71 and 3.99 (ABq, 2H, J=18 Hz), 4.02 and 4.18 (ABq, 2H, J=14 Hz), 4.70 (d, 1H, J=1.5 Hz), 5.19 (d, 1H, J=1.5 Hz), 6.97 (s, 1H), 7.31–7.46 (m, 10 H).

STEP E: Preparation of benzhydryl 7α-methoxy-3-[(1, 2, 3-triazolyl) methyl]-3-cephem-4-carboxylate-1, 1-dioxide A solution of benzhydryl 7α-methoxy-3-azidomethyl-3-cephem-4-carboxylate-1,1-dioxide (3.1 g, 6.62 mmol) in ethylene glycol dimethyl ether (60 ml) was transferred to a steel bomb and cooled to −78° C.; the reaction vessel was flushed with nitrogen for 15 min; 14.0 g of acetylene was taken in the steel bomb and the reaction mixture was heated at 90° C. overnight. The steel bomb was cooled in an ice-bath and the excess acetylene was slowly allowed to evaporate at room temperature. Solvent was removed under reduced pressure. The crude product was purified on a silica column using hexane-ethyl acetate (1:1) as eluant to give a foamy product, 1.9 g (58%). Ether was added to the foam and solid separated out was filtered off, m.p. 123°–125° C. 1R (Nujol) ν max 1786, 1713 cm−1.

NMR ($CDCl_3$) δ 3.55 (s, 3H), 3.65 and 3.97 (ABq, 2H, J=18 Hz), 4.74 (s, 1H), 5.16 (s, 3H), 7.10 (s, 1H), 7.30–7.43 (m, 10 H), 7.51 (s, 1H), 7.67 (s, 1H).

STEP F: Preparation of benzhydryl 7α-methoxy-2 exomethylene-3-[(1,2, 3-triazolyl)methyl]-3-cephem-4-carboxylate-1, 1-dioxide To a solution of benzhydryl 7α-methoxy-3-[(1,2, 3-triazolyl) methyl]-3-cephem-4-carboxylate-1,1 dioxide (1.8 g, 3.85 mmol) in dichloromethane (30 ml) and t-butanol (70 ml) was added dimethylamine hydrochloride (940 mg, 11.54 mmol) and formaldehyde solution (37%, 410 mg, 13.5 mmol). The mixture was heated at 80° C. for 1.5 h and solvent was removed in vacuo. The residue was taken in dichloromethane (60 ml) and washed with cold water, brine, dried and concentrated. The residue was purified by silica column using hexane-ethyl acetate (1:2) as eluant to give benzhydryl 7α-methoxy-2-exomethylene-3-[(1, 2, 3-triazolyl)methyl]-3-cephem-4-carboxylate-1, 1-dioxide (910 mg, 49%); m.p. 177°–179° C., dec. (ethyl acetate-ether). IR (Nujol) ν max 1765, 1723 cm−1

NMR (CDCl$_3$) δ 3.57 (s, 3H), 4.87 (d, 1H, J=2 Hz), 5.01 and 5.47 (ABq, 2H, J=15 Hz), 5.29 (d, 1H, J=2 Hz), 6.55 (d, 1H, J=2.6 Hz), 6.64 (d, 1H, J=2.6 Hz), 7.06 (s, 1H), 7.3-7.37 (m, 10 H), 7.51 (s, 1H), 7.58 (s, 1H).

STEP G: Benzhydryl 7α-methoxy-2-spiro (2',2'-diphenyl) cyclopropyl-3-[(1,2,3-triazolyl) methyl]-3-cephem-4-carboxylate-1,1-dioxide To a stirred solution of benzhydryl 7α-methoxy -2-exomethylene-3-[(1,2,3-triazolyl) methyl] -3-cephem-4-carboxylate-1, 1-dioxide (840 mg, 1.66 mmol) in dichloromethane (20 ml) at room temperature was added diphenyldiazomethane (390 mg, 2.01 mmol). The reaction mixture was stirred at room temperature for 1 h, solvent was removed under reduced pressure. The residue was purified by silica column chromatography using ethyl acetate-hexane (1:1) as eluant to give 600 mg (54%) of pure benzhydryl 7α-methoxy-2-spiro-(2',2'-diphenyl) cyclopropyl-3-[(1,2,3-triazolyl) methyl]-3-cephem-4-carboxylate-1, 1-dioxide, m.p. 196°-198° C. dec. (ethyl acetate-hexane). IR (Nujol) ν max 1783, 1732 cm−1.

NMR (CDCl$_3$) δ 2.55 and 2.75 (ABq, 2H, J=7.6 Hz), 3.5 and 4.0 (ABq, 2H, J=15 Hz), 3.47 (s, 3H), 5.0 (d, 1H, J=2 Hz), 5.1 (d, 1H, J=2 Hz), 7.06 (s, 1H), 7.24-7.49 (m, 20 H), 7.63 (s, 1H), 7.9 (s, 1H).

EXAMPLE 15

7α-Methoxy-2-spiro(2',2'-diphenyl)cyclopropyl-3-[(1,2 3-triazolyl)methyl]-3-cephem-4-piperidine carboxamide-1,1-dioxide STEP A: Preparation of 7α-methoxy-2-spiro(2',2'-diphenyl) cyclopropyl-3-[(1,2,3-triazolyl)methyl]-3-cephem-4 carboxylic acid-1,1-dioxide Benzhydryl 7α-methoxy-2-spiro(2',2'-diphenyl) cyclopropyl-3-[(1,2,3-triazolyl)methyl]-3-cephem-4-carboxylate-1,1-dioxide (from Step G, Example 14, 220 mg, 0.327 mmol) was dissolved in a mixture of anisole (2 ml) and dichloromethane (1 ml) and cooled in an ice bath with stirring. After stirring at 0° C. for 10 min, trifluoroacetic acid (3 ml) was added. The resulting mixture was stirred at 0° C. for 1 h and solvent was removed to give an oil. A mixture of dry ether (5 ml) and hexane (5 ml) was added to the oil and the mixture was stirred with ice-cooling. The precipitated white solid was collected by filtration and dried over phosphorus pentoxide overnight to give 160 mg (97%) of 7α-methoxy-2-spiro(2',2'-diphenyl) cyclopropyl-3-[(1,2,3-triazolyl)methyl]-3-cephem-4-carboxylic acid-1,1-dioxide.

NMR(CDCl$_3$) δ 2.45 (d, 1H, J=7.6 Hz), 2.81 (d, 1H, J=7.6 Hz), 3.48 (s, 3H), 3.6 (d, 1H, J=15 Hz), 4.76 (d, 1H, J=15 Hz), 5.06 (d, 1H, J 1.8 Hz), 5.09 (d, 1H, J=1.8 Hz), 6.0 (br, S, 1H), 7.24-7.52 (m, 10 H), 7.77 (s, 1H), 8.10 (s, 1H).

STEP B: 7α-Methoxy-2-spiro(2',2'-diphenyl)cyclopropyl-3-[(1,2,3-triazolyl)methyl]-3-cephem-4-piperidine carboxamide-1,1-dioxide To an ice-cooled solution of 7α-methoxy-2-spiro-(2',2'-diphenyl)cyclopropyl-3-[(1,2,3-triazolyl) methyl]-3-cephem-4-carboxylic acid-1,1-dioxide (150 mg, 0.296 mmol) in dichloromethane (3 ml) was added oxalyl chloride (46 mg, 0.362 mmol) dissolved in dichloromethane (1 ml), dimethyl formamide (1 drop) was added and the reaction mixture was stirred at 0° C. for 15 min. followed by at room temperature for 15 min. Solvent was removed under reduced pressure and the residue was redissolved in dichloromethane (2 ml), cooled in an ice-bath, piperidine (58 mg, 0.68 mmol) in dichloromethane (1 ml) was added dropwise and the reddish brown solution was stirred at 0° C. for 1 h. Solvent was removed under reduced pressure to give a crude product (240 mg) which was purified on a silica column using ethyl acetate-acetonitrile (6:4) mixture as eluant to give pure 7α-methoxy-2-spiro-(2',2'-diphenyl) cyclopropyl-3-[(1,2,3 -triazolyl) methyl]-3-cephem-4-piperidine carboxamide-1,1-dioxide.

NMR(CDCl$_3$) δ 1.63-2.09 (m, 6H, piperidyl), 2.37 (d, 1H, J=7.2 Hz), 3.01 (d, 1H, J=7.2 Hz), 3.47-3.60 (m, 6H, piperidyl+3'-CH$_2$), 3.50 (s, 3H, OCH$_3$), 4.84 (d, 1H, J=1.3 Hz), 4.86 (d, 1H, J=1.3 Hz), 6.98-7.53 (m, 10 H, aromatic), 7.87 (s, 1H), 8.10 (s, 1H).

EXAMPLE 16 p-Methoxybenzyl 7α-methoxy-2-spiro(2',2'-diphenyl) cyclopropyl-3-[(1,2,3-triazolyl)methyl]-3-cephem-4-carboxylate-1,1-dioxide STEP A: Preparation of p-methoxybenzyl 7β-amino-3-azido-methyl-3-cephem-4-carboxylate p-Methoxybenzyl-7-amino-3-chloromethyl-3-cephem-4-carboxylate (30.5 g, 0.083 mol) was dissolved in N,N-dimethylformamide (160 ml). A solution of sodium azide (26.88 g, 0.414 mol) in water (75 ml) was added dropwise over a period of 15 min to the above solution and the dark brown reaction mixture was stirred at room temperature for 2.5 h. The reaction mixture was diluted with methylene chloride and the organic layer was separated, washed successively with water, brine, dried (Na$_2$SO$_4$) and concentrated in vacuo to give a dark brown residue (25 g) which was purified over silica column using a mixture of hexane-ethyl acetate (1:3) as eluant to give pure p-methoxybenzyl 7β-amino-3-azidomethyl-3-cephem-4-carboxylate (17.5 g, 55.3%). IR (Nujol) ν max 2105 cm−1.

NMR (CDCl$_3$) δ 1.80 (br, 2H, NH$_2$), 3.47 (ABq, 2H, J=18 Hz), 3.81 (s, 3H, OCH$_3$), 3.93 and 4.34 (ABq, 2H, J=13.7 Hz), 4.75 (d, 1H, J=5.1 Hz), 4.91 (d, 1H, J=5.1 Hz), 5.23 (s, 2H, —COOCH$_2$), 6.89 (d, 2H, aromatic), 7.35 (d, 2H, aromatic).

STEP B: Preparation of p-methoxybenzyl 7β-amino-3-azidomethyl-3-cephem-4-carboxylate-1,1-dioxide p-Methoxybenzyl 7β-amino-3-azidomethyl-3-cephem-4-carboxylate (17.15 g, 0.046 mol) in ethyl acetate was cooled to 15° C., sodium tungstate dihydrate (1.52 g, 0.0046 mol) was added followed by hydrogen peroxide (30%, 20.73 ml) in one portion and the stirring was continued at room temperature. After two hours an additional portion of hydrogen peroxide (5.18 ml) was added and the reaction mixture was stirred at room temperature for a total period of 18 h; the mixture was cooled to 10° C. and a solution of sodium sulphite (10%, 600 ml) was added while stirring. Organic layer was separated out, washed with aq. sodium bicarbonate solution, brine and dried (Na$_2$SO$_4$). Evaporation of the solvent in vacuo gave a foam (12 g) which was purified over a silica column using hexane-ethyl acetate (1:3) as eluant to give the pure product as a white foam (6.8 g, 36.5%). IR (Nujol) ν max 2083 cm−1.

NMR (CDCl$_3$) δ 2.23 (br s, 2H, NH$_2$), 3.71 and 3.92 (ABq, 2H, J=18 Hz, CH$_2$N$_3$), 3.81 (s, 3H, OCH$_3$), 4.11 and 4.34 (ABq, 2H, J=14 Hz), 4.72 (d, 1H, J=4 Hz), 4.89 (d, 1H, J=4 Hz), 5.24 (s, 2H, —COOCH$_2$), 6.90 (d, 2H, aromatic), 7.39 (d, 2H, aromatic).

STEP C: Preparation of p-methoxybenzyl 7β-amino-3-[(1,2, 3-triazolyl) methyl]-3-cephem-4-carboxylate-1,1-dioxide p-Methoxybenzyl 7β-amino-3-azidomethyl-3-cephem-4-carboxylate-1,1-dioxide (2.7 g, 0.0066 mol) was dissolved in ethylene glycol dimethyl ether (100 ml) and placed in a steel bomb. The reaction vessel was cooled to −60° C. and charged with 3.0 g of acetylene. The steel bomb was heated at 90° C. over a period of 8 h. Excess acetylene was carefully vented out at 0° C. and the solvent was removed in vacuo to give a crude mass (2.0 g) which was purified on a silica column using hexane-ethyl acetate (3:7) as eluant to give pure p-methoxybenzyl-7β-amino-3-[(1,2,3-triazolyl)-methyl]-3-cephem-4-carboxylate-1,1-dioxide (1.45 g, 50.52%).

NMR(CDCl$_3$) δ 2.04 (br, 2H, NH$_2$), 3.59 and 3.95 (ABq, 2H, J=18.3 Hz), 3.80 (s, 3H, OCH$_3$), 4.64 (br, s, 1H), 4.87 (br, s, 1H), 5.04-5.36 (m, 4H), 6.89 (d, 2H, aromatic), 7.31 (d, 2H, aromatic), 7.68 (s, 2H, triazole).

STEP D: Preparation of p-methoxybenzyl-7α-methoxy-3-[(1,2,3-triazolyl)methyl]-3-cephem-4-carboxylate-1,1-dioxide A solution of p-methoxybenzyl-7β-amino-3-[(1,2,3-triazolyl)methyl]-3-cephem-4-carboxylate-1,1-dioxide (800 mg, 0.00185 mol) in dry ethyl acetate was cooled to 10° C. under nitrogen. Isopropyl nitrite (0.247 g, 0.0028 mol) was added to the above solution followed by 3 drops of trifluoroacetic acid. The reaction mixture was further stirred at 10° C. for 1 h and cooled to −5° C. Rhodium octanoate dimer (18 mg) was dissolved in a mixture of ethyl acetate (10 ml) and anhydrous methanol (2 ml) and the mixture was stirred under nitrogen at 0° C. After stirring for 30 min, 5 drops of triethylamine was added (the color changes from light green to purple) and the solution was further cooled to −5° C.

The above two solutions were mixed together at −5° C. and stirred for 2 h. The reaction mixture was diluted with 50 ml of ethylacetate, made acidic with glacial acetic acid, the reaction mixture was washed with cold water, brine, dried over anhydrous sodium sulfate. Evaporation of the solvent gave a dark brown foam which was purified over silica column using hexane-ethyl acetate (1:1) as eluant to give the desired product, p-methoxybenzyl-7α-methoxy-3-[(1,2,3-triazolyl)methyl]-3-cephem-4 carboxylate-1,1-dioxide, 140 mg (20%).

NMR(CDCl$_3$) δ 3.54 (s, 3H, OCH$_3$), 3.65 and 3.93 (ABq, 2H, J=18 Hz), 3 82 (s, 3H, OCH$_3$), 4.70 (d, 1H, J=1.1 Hz), 5.08-5.40 (m, 5H), 6.91 (d, 2H, aromatic), 7.37 (d, 2H, aromatic), 7.73 (s, 2H, triazole).

STEP E: Preparation of p-methoxybenzyl-7α-methoxy-2 exomethylene-3-[(1,2,3-triazolyl)methyl]-3-cephem 4-carboxylate-1,1-dioxide To a solution of p-methoxybenzyl-7α-methoxy-3-[(1,2,3-triazolyl)methyl]-3-cephem-4-carboxylate-1,1-dioxide (1.27 g, 0.0028 mol) in dry dichloromethane (8 ml) was added successively dimethylamine hydrochloride (0.692 g), formaldehyde (0.804 ml) solution and t-butanol (35 ml). The reaction mixture was heated with stirring at 75° C. for 2.5 h; solvent was removed under reduced pressure. The residue was dissolved in methylene chloride, washed with water, brine, dried (Na$_2$SO$_4$) and evaporated to give a gummy mass which was purified over a silica column using a mixture of hexane-ethyl acetate (1:1) as eluant to give p-methoxybenzyl-2-exomethylene-7α-methoxy-3-[ (1,2,3-triazolyl)methyl]-3-cephem- 4-carboxylate-1,1-dioxide.

NMR(CDCl$_3$) δ 3.57 (s, 3H, OCH$_3$), 3.81 (s, 3H, OCH$_3$), 4.81 (d, 1H, J=1.48 Hz), 5.17-5.54 (m, 5H), 6.56 (d, 1H, J=2.6 Hz), 6.63 (d, 1H, J=2.6 Hz), 6.90 (d, 2H, aromatic), 7.35 (d, 2H, aromatic), 7.66 (s, 1H, triazole), 7.76 (s, 1H, triazole).

STEP F: Preparation of p-methoxybenzyl-2-spiro(2',2'-diphenyl)cyclopropyl-7α-methoxy-3-[(1,2,3-triazolyl)methyl]-3-cephem-4-carboxylate-1,1-dioxide To a stirred solution of p-methoxybenzyl-2-exomethylene-7α-methoxy-3-[(1,2,3-triazolyl)methyl]-3-cephem-4-carboxylate-1,1-dioxide (300 mg, 0.00065 mol) in methylene chloride (20 ml) was added diphenyldiazomethane (164 mg, 0.00085 mol) and the reaction mixture was stirred at room temperature for 12 h, the mixture was diluted with methylene chloride, washed with brine, dried (Na$_2$SO$_4$) and evaporated to give a pink foam (380 mg) which was purified over a silica column using a mixture of hexane-ethyl acetate (1:1) as eluant to give the desired product, p-methoxybenzyl-2-spiro(2',2'-diphenyl)-7α-methoxy-3-[(1,2,3-triazolyl)methyl]3-cephem-4-carboxylate-1,1-dioxide (295 mg, 73%).

NMR(CDCl$_3$) δ 2.57 (d, 1H, J=7.8 Hz), 2.77 (d, 1H, J=7.8 Hz), 3.47 (s, 3H, OCH$_3$), 3.84 (s, 3H, OCH$_3$), 3.57 and 4.34 (ABq, 2H, J=15.3 Hz), 4.98 (d, 1H, J=2 Hz), 5.07 (d, 1H, J=2 Hz), 5.23 and 5.35 (ABq, 2H, J=11.6 Hz), 6.87-7.47 (m, 14 H, aromatic), 7.67 (s, 1H, triazole), 7.93 (s, 1H, triazole).

EXAMPLE 17

7α-Methoxy-2-spiro(2',2'-diphenyl)cyclopropyl-3-methyl-3-cephem-4-[2-(S)-t-butoxycarbonyl pyrrolidine carboxamide[-1,1-dioxide 7α-Methoxy-2-spiro (2',2'-diphenyl)cyclopropyl-3-methyl-3-cephem-4-carboxylic acid-1,1-dioxide (0.41 g, from Step A, Example 9) was dissolved in 5 ml of dichloromethane, oxalyl chloride (0.1 ml) was added followed by two drops of N,N-dimethyl formamide. The reaction mixture was stirred at ice-temperature for 15 min. and then at room temperature for 15 min. Solvent was removed under reduced pressure. The crude mass was redissolved in dry dichloromethane (5 ml), cooled in an ice-bath, 2-(S)-t-butoxycarbonyl pyrrolidine (0.31 g) was added in one portion and the mixture was stirred at ice-temperature for 1 h. The reaction mixture was diluted with dichloromethane, washed successively with water, dil. hydrochloric acid and brine; dried (Na$_2$SO$_4$) and concentrated to give a light brown foam (0.42 g) which was purified on column using hexane-ethyl acetate mixture as eluant to give pure 7α-methoxy-2-spiro(2',2'-diphenyl)-cyclopropyl-3-methyl-3-cephem-4-[2-(S)-t-butoxycarbonyl pyrrolidine carboxamide]-1,1-dioxide as a white foam (0.011 g).

NMR(CDCl$_3$) δ 1.28 (s, 3H, CH$_3$) 1.42 (s, 9H, t-butyl), 1.92-2.20 (m, 4H, pyrrolidinyl), 2.26 (d, 1H, J=7.0 Hz), 2.80 (d, 1H, J=6.92 Hz), 3.40-3.49 (m, 1H, pyrrolidinyl), 3.43 (s, 3H, OCH$_3$), 3.61-3.71 (m, 1H, pyrrolidinyl), 4.41-4.46 (br, dd, 1H, pyrrolidinyl), 4.53 (d, 1H, J=1.85 Hz), 4.74 (d, 1H, J=1.87 Hz), 7.15-7.48 (m, 10 H, aromatic).

EXAMPLE 18

7α-Methoxy-2-spiro(2',2'-diphenyl)cyclopropyl-3-methyl-3-cephem-4-[2-(S)-carboxy pyrrolidine carboxamide[-1,1-dioxide A solution of 7α-methoxy-2-spiro(2',2'-diphenyl)cyclopropyl-3-methyl-3-cephem-4-[2-(S)-t-butoxycarbonyl pyrrolidine carboxamide]-1,1-dioxide (150 mg, 0.25 mmol) in anhydrous formic acid (15 ml) was stirred at room temperature for 2 hours. After the completion of the reaction, the reaction mixture was freeze-dried to give a white solid which was washed repeatedly with a mixture of hexane-ether (4:1), air dried (131 mg, 96.32%).

$^1$H NMR (200 MHz, CDCl$_3$): δ 1.13 and 1.21 (2s, 3H), 2.02–2.23 (m, 4H, pyrrolidinyl), 2.32 (d, 1H, J=7.0 Hz), 2.78 (d, 1H, J=7.0 Hz), 3.40 (s, 1H, pyrrolidinyl), 3.44 (s, 3H), 3.47–3.62 (m, 1H, pyrrolidinyl), 4.31–4.44 (m, 1H, pyrrolidinyl), 4.75 (br, s, 1H), 4.89 (br, s, 1H), 7.20–7.41 (m, 10H), 12.41 (br, s, 1H).

EXAMPLE 19

7α-Methoxy-2-spiro(2',2'-diphenyl)cyclopropyl-3-methyl-3-cephem-4-[4-t-butoxycarbonyl piperidine carboxamide[-1,1-dioxide 7α-Methoxy-2-spiro(2',2'-diphenyl)cyclopropyl-3-methyl-3-cephem-4-carboxylic acid-1,1-dioxide (2.87 g. 6.53 mmol) was taken in dry methylene chloride (40 ml), oxalyl chloride (1.10 g) was added followed by two drops of dimethyl formamide. The reaction mixture was stirred at ice-temperature for 15 min and then at room temperature for 1 hour. Solvent was removed under reduced pressure, the residue was dissolved in methylene chloride (50 ml) and evaporated again in vacuo. The residue was redissolved in methylene chloride (50 ml), cooled to 0° C.; a solution of t-butyl isonipecotinate (1.21 g, 6.53 mmol) in dry methylene chloride (50 ml) was added followed by triethylamine (0.667 g, 6.53 mmol). The reaction mixture was stirred at 0° C. for 30 min and at room temperature for 2.5 hours. After the reaction was complete, the reaction mixture was diluted with methylene chloride (100 ml) and washed successively with water, 1(N) HCl acid, water, aq. NaHCO$_3$ solution, brine, dried over anhydrous Na$_2$SO$_4$. Evaporation of the solvent under reduced pressure gave a foam (4.1 g) which was purified over a silica gel column using hexane-ethyl acetate mixture (1:1) as eluant to give a white foam (3.29 g, 83.09%).

$^1$H NMR (200 MHz, CDCl$_3$): δ 0.89 and 0.92 (2s, 3H), 1.42 and 1.44 (2s, 9H), 1.51–2.03 (m, 4H, piperidyl), 2.24 (d, 1H, J=7.0 Hz), 2.37–2.47 (m, 1H, piperidyl), 2.91 (d, 1H, J=7.0 Hz), 2.97–3.11 (m, 2H, piperidyl), 3.45 (s, 3H), 3.64–3.79 (m, 1H, piperidyl), 4.34–4.41 (m, 1H, piperidyl), 4.96 (br, s, 1H), 5.03–5.06 (m, 1H), 7.17–7.50 (m, 10H).

EXAMPLE 20

7α-Methoxy-2-spiro(2',2'-diphenyl)cyclopropyl-3-methyl-3-cephem-4-[4-carboxy piperidine carboxamide]-1,1-dioxide A solution of 7α-methoxy-2-spiro(2'2'-diphenyl) cyclopropyl-3-methyl-3-cephem-4-[4-t-butoxycarbonyl piperidine carboxamide]-1,1-dioxide (4.4 g, 7.3 mmol) in anhydrous formic acid (70 ml) was stirred at room temperature for 2 hours. After the completion of the reaction the reaction mixture was freeze-dried to give a white solid which was washed thoroughly with a mixture of hexane-ether (4:1), the solid was collected by filtration and air dried (3.78 g, 94.74%).

$^1$H NMR (200 MHz, CDCl$_3$+DMSO-d$_6$): δ 0.87 and 0.90 (2s, 3H), 1.58–2.05 (m, 4H, piperidyl), 2.26 (d, 1H, J=6.70 Hz), 2.49–2.51 (m, 1H, piperidyl), 2.90 (d, 1H, J=6.70 Hz), 3.03–3.14 (m, 2H, piperidyl), 3.46 (s, 3H), 3.63–3.82 (m, 1H, piperidyl), 5.00 (br, s, 1H), 5.04 (br s, 1H), 7.21–7.48 (m, 10H), 11.90 (br s, 1H).

EXAMPLE 21

7α-Methoxy-2-spiro (2',2'-diphenyl) cyclopropyl-3-methyl-3-cephem-4-[2-{N-(t-butylpropionate-2-yl) carboxamido}] pyrrolidine carboxamide 1,1-dioxide.

To a stirred and ice cooled solution of 7α-methoxy-2-spiro (2',2'-diphenyl) cyclopropyl-3-methyl-3-cephem-4-carboxylic acid 1,1-dioxide (365 mg, 0.83 mmol) in methylene chloride (15 ml) was added oxalyl chloride (140 mg, 1.08 mmol) followed by two drops of DMF. The suspension became clear within 5 minutes. The reaction mixture was stirred at ice-temperature for 15 min and at room temp. for 30 min. Then it was evaporated in vacuo to give a pink colored solid. The solid was redissolved in DCM and evaporated in vacuo. The solid thus obtained was dissolved in DCM (10 ml) and cooled to 0° C. under nitrogen atmosphere. A solution of Pro-Ala-tert-butyl ester (201 mg, 0.83 mmol) in DCM (3 ml) was added to the above reaction mixture followed by triethylamine (85 mg. 0.83 mmol) dissolved in 2 ml of DCM. The above reaction mixture was stirred at 0° C. for 15 min and at room temp. for 3 hours. The reaction mixture was diluted with 100 ml of DCM and washed successively with cold water, aq. NaHCO$_3$ solution, brine, dried over anhydrous Na$_2$SO$_4$ and evaporated to give a light green colored foam (480 mg) which was purified over a silica gel column using a mixture of hexane-ethyl acetate (1:1) as eluant. The compound obtained (310 mg) was further purified by preparative tlc using a mixture of methylene chloride-ethyl acetate (8:2) as developing solvent. The purified product was used in Example 22.

EXAMPLE 22

7α-Methoxy-2-spiro (2',2'-diphenyl) cyclopropyl-3-methyl-3-cephem-4-[2-{N-(α-methylacetic acid) carboxamido}] pyrrolidine carboxamide 1,1-dioxide A solution of 7α-methoxy-2-spiro (2',2'-diphenyl) cyclopropyl-3-methyl-3-cephem-4[2-{N-(t-butyl propionate-2-yl) carboxamido}] pyrrolidine carboxamide 1,1-dioxide (104 mg, 0.16 mmol) in anhydrous formic acid (9 ml) was stirred at room temp. for 2 hours and freeze dried (93 mg).

$^1$H NMR (200 MHz, CDCl$_3$): δ 0.90 (s, 3H, CH$_3$), 1.49 (d, 3H, J=1.33 Hz), 1.81–2.19 (m, 2H, pyrrolidinyl), 2.22–2.28 (m, 3H, cyclopropyl+pyrrolidinyl), 2.95 (d, 1H, J=6.94 Hz, cyclopropyl), 3.35–3.58 (m, 5H, CH$_3$O+pyrrolidinyl), 4.52–4.65 (m, 2H, pyrrolidinyl), 5.11 (d, 1H, J=1.96 Hz), 5.13 (d, 1H, J=1.96 Hz), 7.19–7.52 (m, 11H, aromatic+COOH), 7.90 (d, 1H, J=7.28 Hz, NH).

EXAMPLE 23

7α-Methoxy-2-spiro (2',2'-diphenyl) cyclopropyl-3-methyl-3-cephem-4-{N-(1-t-butyloxycarbonyl-3-methyl-butane-1-yl)} carboxamido-1, 1-dioxide To a stirred and ice-cooled solution of 7α-methoxy-2-spiro (2',2'-diphenyl)cyclopropyl-3-methyl-3-cephem-4-carboxylic acid 1,1-dioxide (685 mg, 1.56 mmol) in methylene chloride (50 ml) was added oxalyl chloride (263 mg, 2.03 mmol) followed by two drops of DMF. The reaction mixture was stirred at 10° C. for 15 min and at room temperature for 45 min and then it was evaporated in vacuo. The residue thus obtained was redissolved in methylene chloride and evaporated again in vacuo. The residue was finally dissolved in anhydrous methylene chloride (50 ml) and cooled to 5° C. under N$_2$, to the above solution a solution of leucine-t- butyl ester (307 mg, 1.64 mmol) in methylene chloride (2 ml) was added followed by a solution of triethylamine (175 mg, 1.72 mmol) in methylene chloride (1 ml). The reaction mixture was stirred at 5° C. for 15 min, then at room temperature for 3 hours, diluted with methylene chloride (100 ml) and washed successively with water, 1(N) HCl acid, water, aq. $NaHCO_3$ solution, brine, and dried over anhydrous $Na_2SO_4$ and evaporated in vacuo to give a yellow colored foam (800 mg) which was purified over a silica gel column using a mixture of hexane-ethyl acetate (3:2) to give the product as a white solid (590 mg, 62.17%).

$^1$H NMR (200 MHz, $CDCl_3$): δ 0.95 (d, 6H, J=6.13 Hz), 1.07 (s, 3H), 1.49 (s, 9H), 1.57–1.80 (m, 3H), 2.31 (d, 1H, J=7.0 Hz), 2.92 (d, 1H, J=7.0 Hz), 3.46 (s, 3H), 4.6 (q, 1H), 4.92 (d, 1H, J=2.0 Hz), 5.03 (d, 1H, J=2.0 Hz), 6.44 (d, 1H, J=8.1 Hz), 7.21–7.47 (m, 10H).

EXAMPLE 24

7α-Methoxy-2-spiro (2′,2′-diphenyl) cyclopropyl-3-methyl-3-cephem-4-{N-(1-carboxy-3-methyl-butane-1-yl)} carboxamido-1,1-dioxide A solution of 7α-methoxy-2-spiro (2′,2′-diphenyl) cyclopropyl-3-methyl-3-cephem-4-{N-(1-t-butoxycarbonyl-3-methyl-butane-1-yl)} carboxamido-1,1-dioxide (170 mg, 0.28 mmol) in anhydrous formic acid (15 ml) was stirred at room temperature for 2 hours. The progress of the reaction was followed by tlc; when all the starting material was completely disappeared, the reaction mixture was freezedried to give a white solid which was washed thoroughly with a mixture of hexane-ether (9:1). The solid was collected by filtration and air dried (153 mg, 99.35%).

$^1$H NMR (200 MHz, $CDCl_3$): δ 0.95 (d, 6H, J=1.41 Hz), 1.07 (s, 3H), 1.75 (br, s, 3H), 2.33 (d, 1H, J=7.0 Hz), 2.93 (d, 1H, J=7.0 Hz), 3.46 (s, 3H), 4.74 (br m, 1H), 4.97 (br s, 1H), 5.04 (br s, 1H), 6.71 (br d, 1H), 7.26–7.47 m, 10H).

EXAMPLE 25

7α-Methoxy-2-spiro(2′,2′-diphenyl)cyclopropyl-3-methyl-3-cephem-4-((N-methyl piperazine carboxamide)-1,1-dioxide To a stirred and ice-cooled solution of 7α-methoxy-2-spiro(2′,2′-diphenyl)cyclopropyl-3-methyl-3-cephem-4-carboxylic acid -1,1-dioxide (0.439 g, from Step A, Example 9), in dry dichloromethane (5 ml) was added oxalyl chloride (0.1 ml) followed by two drops of N,N-dimethyl formamide, the reaction mixture was stirred at ice-temperature for 15 min and at room temperature for 15 min. Solvent was removed under reduced pressure. The residue was redissolved in dry dichloromethane (5 ml), cooled in an ice-bath, N-methyl piperazine (0.22 ml) was added in one portion and the reaction mixture was stirred at ice-temp. for 1 h. The reaction mixture was diluted with methylene chloride, washed with ice-cold water, dil. hydrochloric acid and finally with brine, dried ($Na_2SO_4$) and concentrated to give a brown foam which was purified on silica gel column using hexane-ethyl acetate mixture as eluant to give 0.32 g of pure product which was crystallized from ether to give a pale yellow solid (0.192 g), m.p. 202°–204° C.

NMR($CDCl_3$): δ 0.89 (s, 3H, $CH_3$), 2.24 (d, 1H, J=7.07 Hz), 2.28 (s, 3H, N—$CH_3$), 2.36–2.54 (m, 4H, piperazinyl), 2.91 (d, 1H, J=7.07 Hz), 3.46 (s, 3H, $OCH_3$), 3.49–3.62 (m, 3H, piperazinyl), 3.77–3.85 (m, 1H, piperazinyl), 4.95 (d, 1H, J=2.05 Hz), 5.05 (d, 1H, J=2.09 Hz), 7.17–7.50 (m, 10H, aromatic).

EXAMPLE 26

7α-Methoxy-2-spiro (2′,2′-diphenyl) cyclopropyl-3-methyl-3-cephem-4-(4-tert-butoxycarbonyl)piperazine carboxamide-1,1-dioxide To a stirred and ice cooled suspension of 7α-methoxy-2-spiro (2′,2′-diphenyl) cyclopropyl-3-methyl-3-cephem-4-carboxylic acid 1,1-dioxide (1.0 g, 2.28 mmol) in methylene chloride (50 ml) was added oxalyl chloride (0.347 g, 2.74 mmol) followed by two drops of DMF. The suspension became clear after a few minutes. The reaction mixture was stirred at ice-bath temperature for 10 min and at room temperature for 1.5 h at Which time the solvent was removed in vacuo. The residue was redissolved in methylene chloride (40 mL) and solvent was removed in vacuo. The last step was repeated with another 40 mL of methylene chloride and then the flask was placed on the pump to remove any residual oxalyl chloride. The solid obtained was dissolved in methylene chloride (40 mL) and cooled to 0° C. under nitrogen atmosphere. A solution of t-butoxycarbonyl piperazine (0.51 g, 2.74 mmol) in methylene chloride (10 mL) was added to the above reaction mixture followed by triethylamine (0.277 g, 2.74 mmol). After stirring at ice-bath temperature for 10 min, the mixture was stirred at room temperature for 2.5 h. Methylene chloride (50 mL) was added to the reaction mixture and washed successively with aqueous sodium bicarbonate (5%, 20 mL) solution; water and brine. The methylene chloride solution was dried ($Na_2SO_4$) and solvent was removed in vacuo to give a foam (1.6 g) which was purified over a silica gel column using a mixture of hexane-ethyl acetate (1:2) as eluant to give 1.0 (72%) of product.

$^1$H NMR (200 MHz, $CDCl_3$): δ 0.89 (s, 3H, $CH_3$); 1.44 (s, 9H, t-butyl); 2.24 (d, 1H, J=7.0 Hz, cyclopropyl); 2.92 (d, 1H, J=7.0 Hz, cyclopropyl); 3.38–3.82 (m, 8H, piperazine); 3.46 (s, 3H, $OCH_3$); 4.96 (d, 1H, J=1.9 Hz); 5.04 (d, 1H, J=1.9 Hz); 7.21–7.49 (m, 10H, aromatic).

IR (Nujol): ν max 1777, 1685, 1642 $cm^{-1}$

EXAMPLE 27

7α-Methoxy-2-spiro (2′,2′-diphenyl) cyclopropyl-3-methyl-3-cephem-4-piperazine carboxamide-1,1-dioxide A solution of 7α-methoxy-2-spiro (2′,2′-diphenyl) cyclopropyl-3-methyl-3-cephem-4-[4-tert-butoxycarbonyl] piperazine carboxamide-1,1-dioxide (100 mg, 0.16 mmol) in anhydrous formic acid (3 mL) was stirred in a warm water bath (35° C.) for 1.5 h and freeze dried to give 100 mg of crude product. The residue was purified on a silica gel column eluting with a solvent gradient of hexane-ethyl acetate (1:3), ethyl acetate and finally with ethyl acetate-methanol (4:1) to give 60 mg (72%) of a solid. The solid was dissolved in a minimum amount of methylene chloride and hexane was added to give 20 mg of pure product.

$^1$H NMR (200 MHz, $CDCl_3$): δ 0.90 (s, 3H, $CH_3$); 1.93 (br, s, piperazine); 2.24 (d, 1H, J=7.0 Hz, cyclopropyl); 2.91 (d, 1H, J=7.0 Hz, cyclopropyl); 2.7–3.05 (m, 3H, piperazine); 3.46 (s, 3H, $OCH_3$); 3.3–3.85 (m, 5H, piperazine); 4.96 (d, 1H, J=2 Hz); 5.04 (d, 1H, J=2 Hz); 7.21–7.5 (m, 10H, aromatic).

IR (Nujol): ν max 1778, 1636 $cm^{-1}$

EXAMPLE 28

7α-Methoxy-2-spiro (2',2'-diphenyl) cyclopropyl-3-methyl-3-cephem-4-[4-tert-butoxy carbonyl methyl] piperazine carboxamide-1,1-dioxide To a stirred and ice cooled suspension of 7α-methoxy-2-spiro (2',2'-diphenyl) cyclopropyl-3-methyl-3-cephem-4-carboxylic acid 1,1-dioxide (400 mg, 0.91 mmol) in methylene chloride (20 mL) was added oxalyl chloride (139 mg, 1.09 mmol) followed by two drops of DMF. The reaction mixture was stirred at ice-bath temperature for 10 min and at room temperature for 1.5 h during which time the carboxylic acid dissolved completely. The solvent was removed in vacuo and the resulting solid was redissolved twice in methylene chloride (2×20 mL) and solvent was removed in vacuo each time. The residue was placed on the pump for 40 minutes to remove any remaining oxalyl chloride. The solid obtained was dissolved in methylene chloride (20 mL) and cooled to 0° C. under a nitrogen atmosphere. A solution of t-butoxy-carbonyl methyl piperazine (220 mg, 1.09 mmol) in methylene chloride (15 mL) was added followed by triethylamine (111 mg. 1.09 mmol). After stirring at ice-bath temperature for 10 mins, the reaction mixture was stirred at room temperature for 2 h. Methylene chloride (50 mL) was added to the reaction mixture and then washed successively with dilute HCl [0.5 (N), 15 mL], NaHCO$_3$ (5%, 15 mL) solution, water and brine. The methylene chloride solution was dried (Na$_2$SO$_4$) and solvent was removed in vacuo to give 0.65 g of foam. Purification on a silica gel column using hexane-ethyl acetate (1:2, v/v) as eluant gave 350 mg (56%) of product.

$^1$H NMR (200 MHz, CDCl$_3$): δ 0.89 (s, 3H, CH$_3$); 1.45 (s, 9H, t-butyl); 2.24 (d, 1H, J=7.0 Hz, cyclopropyl), 2.91 (d, 1H, J=7.0 Hz, cyclopropyl); 2.54–2.63 (m, 4H, piperazine); 3.12 (s, 2H, CH$_2$); 3.46 (s, 3H, OCH$_3$); 3.12–3.61 (m, 3H, piperazine); 3.86–3.92 (m, 1H, piperazine); 4.95 (d, 1H, J=1.9 Hz); 5.03 (d, 1H, J=1.9 Hz); 7.17–7.49 (m, 10H, aromatic).

EXAMPLE 29

7α-Methoxy-2-spiro (2',2'-diphenyl) cyclopropyl-3-methyl-3-cephem-4-[4-N-acetic acid] piperazine carboxamide-1,1-dioxide A stirred solution of 7α-methoxy-2-spiro (2',2'-diphenyl) cyclopropyl-3-methyl-3-cephem-4-[4-tert-butoxy carbonyl methyl] piperazine carboxamide-1,1-dioxide (190 mg, 0.305 mmol) in anhydrous formic acid (30 mL) was placed in a warm water bath (40° C.). The mixture was stirred overnight during which time the temperature was allowed to drop to room temperature. The resulting mixture was freeze dried and the solid obtained was dissolved in a minimum amount of dichloromethane. Ether and hexane were added to precipitate 35 mg of pure product.

$^1$H NMR (200 MHz, CDCl$_3$): δ 0.89 (s, 3H, CH$_3$); 2.25 (d, 1H, J=7.0 Hz, cyclopropyl); 2.92 (d, 1H, J=7.0 Hz, cyclopropyl); 2.72–2.80 (m, 4H, piperazine); 3.26 (s, 2H, CH$_2$); 3.46 (s, 3H, OCH$_3$); 3.43–4.03 (m, 5H, piperazine+COOH); 4.96 (d, 1H, J=1.9 Hz); 5.03 (d, 1H, J=1.9 Hz); 7.22–7.49 (m, 10H, aromatic).

SUPPLEMENTAL EXAMPLES

SUPPLEMENTAL EXAMPLE 1

Benzhydryl 7α-chloro-2-spiro(2',2'-diphenyl)cyclopropyl-3-methyl-3-cephem-4-carboxylate-1,1-dioxide
and
Benzhydryl 7α-chloro-2-spiro(3',3'-diphenyl)cyclopropyl-3-methyl-3-cephem-4-carboxylate-1,1-dioxide STEP A: Preparation of 7α-chloro-3-methyl-3-cephem-4-carboxylic acid A mixture of 7-ADCA (25 g, 0.117 mol), ethanol (700 ml), water (163 ml) and concentrated hydrochloric acid (163 ml) was cooled to 5° C. Sodium nitrite (11.5 g, 0.167 mol) was added in small portions over 25 minutes and the mixture was stirred for 3.5 hours at 0° C.–5° C.; 300 ml of brine was added and the reaction mixture was extracted with methylene chloride. The organic extract was washed with water, brine, dried over sodium sulfate and concentrated (16.1 g, 58.9%). This crude acid was directly used for the next step without further purification.

STEP B: Preparation of benzhydryl 7α-chloro-3-methyl-3-cephem-4-carboxylate

The 7α-chloro-3-methyl-3-cephem-4-carboxylic acid (10.0 g, 0.0428 mol) was dissolved in methylene chloride (200 ml), and diphenyldiazomethane (10.8 g, 0.0557 mol) dissolved in methylene chloride (50 ml) was added dropwise over 30 minutes. The mixture was stirred at room temperature for two hours. Solvent was removed under reduced pressure and the product was purified over silica column using hexane-ethyl acetate mixture to yield benzhydryl 7α-chloro-3-methyl-3-cephem-4-carboxylate (7.8 g, 45.6%). NMR (CDCl$_3$) δ 2.1 (s, 3H, CH$_3$), 3.25 (bs, 2H, H-2), 4.70 (bs, 1H), 4.75 (bs, 1H), 7.0 (s, 1H, CHPh$_2$), 7.3–7.7 (m, 10H, aromatic).

STEP C: Preparation of benzhydryl 7α-chloro-3-methyl-3-cephem-4-carboxylate 1,1-dioxide Benzhydryl 7α-chloro-3-methyl-3-cephem-4-carboxylate (7.6 g, 0.019 mol) was dissolved in methylene chloride (50 ml) and peracetic acid (13.0 g, 0.171 mol) was added dropwise over 15–20 minutes with ice-cooling. The mixture was stirred for 72 hours at room temperature and was then washed successively with portions of water, saturated sodium bicarbonate solution, and water. Drying over sodium sulfate, filtration, removal of the solvent under reduced pressure and filtration of the residue through a small column of silica gel using methylene chloride gave 9.3 g of benzhydryl 7α-chloro-3-methyl-3-cephem-4-carboxylate 1,1-dioxide as a white foam.

NMR (CDCl$_3$) δ 2.1 (s, 3H, CH$_3$), 3.8 (bs, 2H, H-2), 4.75 (bs, 1H), 5.3 (bs, 1H), 7.0 (s, 1H, CHPh$_2$), 7.4 (bs, 10H, aromatic).

STEP D: Preparation of benzhydryl 7α-chloro-2-methylene-3-methyl-3-cephem-4-carboxylate 1,1-dioxide Benzhydryl 7α-chloro-3-methyl-3-cephem-4-carboxylate 1,1-dioxide (9.3 g, 0.0215 mol) was dissolved in methylene chloride (35 ml), dimethylamine hydrochloride (4.9 g, 0.0645 mol), formaldehyde solution (2.25 g, 0.075 mol) and t-butyl alcohol (300 ml) were added and the mixture was heated to reflux at 95° C. for 4 hours. After removing the solvent under reduced pressure the residue was redissolved in methylene chloride, washed successively with water, dried over sodium sulfate and concentrated. The product was purified over a silica column using hexane-ethyl acetate mixture as the eluant to yield benzhydryl 7α-chloro-2-methylene-3-methyl-3-cephem-4-carboxylate 1,1-dioxide (3.6 g, 40%) as a white foam. IR (Nujol) ν max 1723, 1800 cm$^{-1}$.

NMR (CDCl$_3$) δ 2.01 (s, 3H, CH$_3$), 4.82 (d, 1H, J=1.5 Hz), 5.3 (d, 1H, J=1.5 Hz), 6.12 (d, 1H, exomethylene, J=2.0 Hz), 6.62 (d, 1H, exomethylene, J=2.0 Hz), 6.93 (s, 1H, CHPh$_2$), 7.25-7.39 (m, 10H, aromatic).

STEP E: Preparation of benzhydryl 7α-chloro-2-spiro(2',2'-diphenyl)cyclopropyl-3-methyl-3-cephem-4-carboxylate 1,1-dioxide and Benzhydryl 7α-chloro-2-spiro(3',3'-diphenyl)cyclopropyl-3-methyl-3-cephem-4-carboxylate-1,1-dioxide Benzhydryl 7α-chloro-2-methylene-3-methyl-3-cephem-4-carboxylate 1,1-dioxide (1.0 g, 0.00225 mol) was dissolved in methylene chloride (70 ml) and cooled to −15° C. To this solution diphenyldiazomethane (0.44 g, 0.00225 mol) was added and the mixture was stirred at room temperature for 2 hours, after removing the solvent under reduced pressure the crude product was purified over silica column using gradient elution with hexane-ethyl acetate mixture. The fast moving component was the minor isomer, benzhydryl 7α-chloro-2-spiro(2',2'-diphenyl)cyclopropyl-3-methyl-3-cephem-4-carboxylate 1,1-dioxide.

NMR (CDCl$_3$) δ 1.63 (s, 3H, CH$_3$), 2.37 (d, 1H, cyclopropyl, J=7 Hz), 2.82 (d, 1H, cyclopropyl, J=7 Hz), 4.72 (d, 1H, J=1.8 Hz), 4.87 (d, 1H, J=1.8 Hz), 6.93 (s, 1H, CHPh$_2$), 7.15-7.54 (m, 20H, aromatic).

The major isomer was benzhydryl 7α-chloro-2-spiro(3',3'-diphenyl)cyclopropyl-3-methyl-3-cephem-4-carboxylate-1,1-dioxide. IR (Nujol) ν max 1726, 1791 cm$^{-1}$.

NMR (CDCl$_3$) 1.02 (s, 3H, CH$_3$), 2.37 (d, 1H, cyclopropyl, J=7 Hz), 2.97 (d, 1H, cyclopropyl, J=7 Hz), 5.01 (d, 1H, J=1.8 Hz), 5.22 (d, 1H, J=1.8 Hz), 7.0 (s, 1H, CHPh$_2$), 7.28-7.48 (m, 20H, aromatic).

NOTE: Subsequent analysis has revealed that the fastmoving component is actually benzhydryl 7α-chloro-2-spiro(3',3'-diphenyl)cyclopropyl-3-methyl-3-cephem-4-carboxylate 1,1-dioxide, and the slow moving component is actually benzhydryl 7α-chloro-2-spiro(2',2'-diphenyl)cyclopropyl-3-methyl-3-cephem-4-carboxylate-1,1-dioxide.

SUPPLEMENTAL EXAMPLE 2

Benzhydryl 7α-bromo-2-spiro(2',2'-diphenyl)cyclopropyl-3-methyl-3-cephem-4-carboxylate-1,1-dioxide and Benzhydryl-7α-bromo-2-spiro(3',3'-diphenyl)cyclopropyl-3-methyl-3-cephem-4-carboxylate-1,1-dioxide STEP A: Preparation of benzhydryl 7α-bromo-3-methyl-3-cephem-4-carboxylate-1,1-dioxide Benzhydryl 7α-bromo-3-methyl-3-cephem-4-carboxylate (16.0 g, 0.036 mol) was dissolved in methylene chloride (75 ml, peracetic acid (24.6 g, 0.324 mol) was added slowly and the mixture was stirred for 72 hours at room temperature, the mixture was washed successively with water, sodium bicarbonate solution and water. Drying over sodium sulfate, filtration, removal of solvent under reduced pressure and purification of the residue over a silica column using methylene chloride as eluant gave benzhydryl 7α-bromo-3-methyl-3-cephem-4-carboxylate 1,1-dioxide (6.7 g, 40%) as a pale yellow foam.

NMR (CDCl$_3$) δ 2.1 (s, 3H, CH$_3$), 3.8 (bs, 2H, H-2), 4.8 (bs, 1H), 5.25 (bs, 1H), 6.95 (s, 1H, CHPh$_2$), 7.2-7.6 (m, 10H, aromatic).

STEP B: Preparation of benzhydryl 7α-bromo-2-methylene-3-methyl-3-cephem-4-carboxylate-1,1-dioxide To a stirred solution of benzhydryl 7α-bromo-3-methyl-3-cephem-4-carboxylate-1,1-dioxide (2.8 g, 0.0059 mol) in methylene chloride (12 ml) were added dimethylamine hydrochloride (1.44 g, 0.0176 mol), formaldehyde (0.61 g, 0.020 mol) and t-butyl alcohol (100 ml), the mixture was heated to reflux at 95° C. for 3 hours. Solvent was removed under reduced pressure and the residue was dissolved in methylene chloride, washed with water, dried over sodium sulfate and concentrated to dryness. The residue was purified by column chromatography with a solvent gradient of 10 to 25% ethyl acetate/hexane to afford benzhydryl 7α-bromo-2-methylene-3-methyl-3-cephem-4-carboxylate-1,1-dioxide (2.0 g, 69.5%) as a white foam.

IR (Nujol) ν$_{max}$ 1720, 1800 cm$^{-1}$.

NMR (CDCl$_3$) 2.10 (s, 3H, CH$_3$), 4.93 (d, 1H, J=1.5 Hz), 5.33 (d, 1H, J=1.5 Hz), 6.20 (d, 1H, exomethylene, J=2 Hz), 6.70 (d, 1H, exomethylene, J=2 Hz), 6.98 (s, 1H, CHPh$_2$), 7.30-7.45 (m, 10H, aromatic).

STEP C: Preparation of benzhydryl 7α-bromo-2-spiro(2',2'-diphenyl)cyclopropyl-3-methyl-3-cephem-4-carboxylate-1,1-dioxide and Benzhydryl 7αbromo-2-spiro(3',3'-diphenyl)cyclopropyl-3-methyl-3-cephem-4-carboxylate-1,1-dioxide Benzhydryl 7α-bromo-2-methylene-3-methyl-3-cephem-4-carboxylate-1,1-dioxide (0.6 g, 0.00123 mol) was dissolved in methylene chloride (50 ml) and cooled to −15° C., diphenyl diazomethane (0.263 g, 0.00135 mol) was added to the solution and the mixture was stirred at room temperature for 3 hours. Evaporation of the solvent under reduced pressure gave a light pink foam consisting of a 4:1 ratio of regio isomers (by NMR) of benzhydryl 7α-bromo-2-spiro[3',3'-(and 2',2')diphenyl]cyclopropyl-3-methyl-3-cephem-4-carboxylate-1,1-dioxide. Two isomers were separated by column chromatography with a solvent gradient of 10 to 30% ethyl acetate/hexane. The fast moving fraction was the minor isomer, benzhydryl 7α-bromo-2-spiro(2',2'-diphenyl)-cyclopropyl-3-methyl-3-cephem-4-carboxylate-1,1-dioxide.

NMR (CDCl$_3$) δ 1.62 (s, 3H, CH$_3$), 2.37 (d, 1H, cyclopropyl, J=7 Hz), 2.82 (d, 1H, cyclopropyl, J=7 Hz), 4.80 (d, 1H, J=1.4 Hz), 4.87 (d, 1H, J=1.4 Hz), 6.92 (s, 1H, CHPh$_2$), 7.15-7.55 (m, 20H, aromatic).

The major isomer was benzhydryl 7α-bromo-2-spiro(3',3'-diphenyl)cyclopropyl-3-methyl-3-cephem-4-carboxylate-1,1-dioxide.

IR (Nujol) ν$_{max}$ 1728, 1790 cm$^{-1}$.

NMR (CDCl$_3$) δ 1.03 (s, 3H, CH$_3$), 2.38 (d, 1H, cyclopropyl, J=7 Hz), 2.96 (d, 1H, cyclopropyl, J=7 Hz), 5.04 (d, 1H, J=1.8 Hz), 5.20 (d, 1H, J=1.8 Hz), 7.0 (s, 1H, CHPh$_2$), 7.22-7.47 (m, 20H, aromatic).

NOTE: Subsequent analysis has revealed that the major isomer is actually benzhydryl 7α-bromo-2-spiro(2',2'-diphenyl)cyclopropyl-3-methyl-3-cephem-4-carboxylate 1,1-dioxide, and the fast moving component is actually the minor isomer, benzhydryl 7α-bromo-2-spiro(3',3'-diphenyl)cyclopropyl-3-methyl-3-cephem-4-carboxylate-1,1-dioxide.

SUPPLEMENTAL EXAMPLE 3

Benzhydryl 7,7-dihydro-2-spiro(3',3'-diphenyl)cyclopropyl-3-methyl-3-cephem-4-carboxylate-1,1-dioxide Following substantially the same procedure as described in Example 1, step E, 0.6 gm of benzhydryl 7,7-dihydro-2-methylene-3-methyl-3-cephem-4-carboxylate-1,1-dioxide in 50 ml of methylene chloride was treated with diphenyldiazomethane to give 0.340 gm (39.4%) of benzhydryl 7,7-dihydro-2-spiro(3',3'-diphenyl(cyclopropyl-3-methyl-3-cephem-4-carboxylate-1,1-dioxide as the major isomer.

IR (Nujol) $\nu_{max}$ 1735, 1786 cm$^{-1}$.

NMR (CDCl$_3$) δ 1.02 (s, 3H, CH$_3$), 2.34 (d, 1H, cyclopropyl, J=7 Hz), 2.94 (d, 1H, cyclopropyl, J=7 Hz), 3.48 (ABX, 2H, H-7, J=2.5, 5.0, 16.0 Hz), 5.03 (dd, 1H, H-6, J=2.5, 5.0 Hz), 7.0 (s, 1H, CHPh$_2$), 7.2–7.48 (m, 20H, aromatic).

NOTE: Subsequent analysis has revealed that the major isomer is actually benzhydryl 7,7-dihydro-2-spiro(2',2'-diphenyl)cyclopropyl-3-methyl-3-cephem-4-carboxylate 1,1-dioxide.

SUPPLEMENTAL EXAMPLE 4 t-Butyl 7α-bromo-2-spiro(3',3'-diphenyl)cyclopropyl-3-methyl-3-cephem-4-carboxylate-1,1-dioxide Following substantially the same procedure as described in Example 1, Step E, 40 mg of t-butyl 7α-bromo-2-methylene-3-methyl-3-cephem-4-carboxylate-1,1-dioxide in 7 ml of methylene chloride was treated with diphenyldiazomethane to give 30 mg (35%) of t-butyl 7α-bromo-2-spiro( 3',3'-diphenyl)cyclopropyl-3-methyl-3-cephem-4-carboxylate-1,1-dioxide as a white foam.

NMR (CDCl$_3$) δ 1.10 (s, 3H, CH$_3$), 1.55 (s, 9H, t-butyl), 2.37 (d, 1H, cyclopropyl, J=7 Hz), 2.96 (d, 1H, cyclopropyl, J=7 Hz), 5.03 (d, 1H, J=2 Hz), 5.18 (d, 1H, J=2 Hz), 7.23–7.48 (m, 10H, aromatic).

NOTE: Subsequent analysis has revealed that the white foam product is actually t-butyl 7α-bromo-2-spiro(2',2'-diphenyl)cyclopropyl-3-methyl-3-cephem-4-carboxylate 1,1-dioxide.

SUPPLEMENTAL EXAMPLE 5

Benzhydryl 7α-bromo-2-spiro[2',2'-(4',4'-dichloro)diphenyl]cyclopropyl-3-methyl-3-cephem-4-carboxylate-1,1-dioxide and Benzhydryl 7α-bromo-2-spiro[3',3'-(4',4'-dichloro)diphenyl]cyclopropyl-3-methyl-3-cephem-4-carboxylate-1,1-dioxide STEP A: Preparation of di(4-chlorophenyl)diazomethane To a stirred ice-cold solution of 4,4'-dichlorobenzophenone hydrazone (1.303 g) in dry methylene chloride (20 ml) was added magnesium sulfate (590 mg), Silver oxide (1.196 g) was added in one portion followed by potassium carbonate (30 mg). The mixture was stirred at ice-temperature for 1 hour, thin at room temperature for an additional hour, filtered through Celite to give a dark purple solution which was directly used for the next reaction.

STEP B: Preparation of benzhydryl 7α-bromo-2-spiro[2',2'-(4',4'-dichloro)diphenyl]cyclopropyl and [3',3'-(4',4'-dichloro)diphenyl]cyclopropyl-3-methyl-3-cephem-4-carboxylate-1,1-dioxide Following substantially the same procedure as described in Example 1, Step E, but substituting for the diphenyldiazomethane used therein, di(4-chlorophenyl)diazomethane there was obtained from 2.0 g of benzhydryl 7α-bromo-2-methylene-3-methyl-3-cephem-4-carboxylate-1,1-dioxide, 1.2 g of pure benzhydryl 7α-bromo-2-spiro[3',3'-(4',4'-dichloro)diphenyl]cyclopropyl-3-methyl-3-cephem-4-carboxylate-1,1-dioxide, m.p. 202° C. (decomp.).

NMR (CDCl$_3$) δ 1.03 (s, 3H, CH$_3$), 2.32 (d, 1H, cyclopropyl, J=7 Hz), 2.90 (d, 1H, cyclopropyl, J=7 Hz), 4.94 (d, 1H, J=1.5 Hz), 5.23 (d, 1H, J=1.5 Hz), 7.03 (s, 1H, CHPh$_2$), 7.18–7.42 (m, 18H, aromatic).

Furthermore, 0.307 g of pure benzhydryl 7α-bromo-2-spiro-2',2'-(4',4'-dichloro)diphenyl]cyclopropyl-3-methyl-3-cephem-4-carboxylate-1,1-dioxide was obtained as the minor isomer.

NMR (CDCl$_3$) δ 1.65 (s, 3H, CH$_3$), 2.31 (d, 1H, cyclopropyl, J=7 Hz), 2.77 (d, 1H, cyclopropyl, J=7 Hz), 4.80 (s, 2H, H-6+H-7), 7.0 (s, 1H, CHPh$_2$), 7.12–7.53 (m, 18H, aromatic).

NOTE: Subsequent analysis has revealed that the major isomer is actually benzhydryl 7α-bromo-2-spiro[2',2'-(4',4'-dichloro)diphenyl]cyclopropyl-3-methyl-3-cephem-4-carboxylate 1,1-dioxide, and the minor isomer is actually benzhydryl 7α-bromo-2-spiro[3',3'-(4',4'-dichloro-diphenyl)cyclopropyl-3-methyl-3-cephem-4-carboxylate-1,1-dioxide.

SUPPLEMENTAL EXAMPLE 6

Benzhydryl 7α-bromo-2-spiro[2',2'-(4',4'-difluoro)diphenyl]cyclopropyl-3-methyl-3-cephem-4-carboxylate-1,1-dioxide and Benzhydryl 7α-bromo-2-spiro[3',3'-(4',4'-difluoro(diphenyl[cyclopropyl-3-methyl-3-cephem-4-carboxylate-1,1-dioxide STEP A: Preparation of di(4-fluorophenyl)diazomethane 4,4'-Difluorobenzophenone (1.0 g, 4.306 mmol) was dissolved in methylene chloride (9 ml) containing iodine (0.2 ml; 1% w/v) and 1,1,3,3-tetramethyl guanidine (2.1 ml). To this solution was added peracetic acid solution (1.23 ml, 6.459 mmol) at 0° C. over 20 minutes. The mixture was stirred at 0° C. for 1 hour, then washed with water until the washings were at pH 6. The methylene chloride layer was dried over anhydrous sodium sulfate and concentrated to give a deep purple oil (850 mg, 83.7%) which was directly utilized for the next reaction.

STEP B: Preparation of benzhydryl 7α-bromo-2-spiro[2',2'-(4',4'-difluoro)diphenyl]cyclopropyl and [3',3'-(4',4'-difluoro)diphenyl]cyclopropyl-3-methyl-3-cephem-4-carboxylate-1,1-dioxide Following substantially the same procedure as described in Example 1, Step E, but substituting for the diphenyldiazomethane used therein, di(4-fluorophenyl)diazomethane there was obtained from 1.6 g of benzhydryl 7α-bromo-2-methylene-3-methyl-3-cephem-4-carboxylate-1,1-dioxide 0.80 g of pure benzhydryl 7α-bromo-2-spiro[3',3'-(4',4'-difluoro)diphenyl]cyclopropyl-3-methyl-3-cephem-4-carboxylate-1,1-dioxide as the major isomer.

NMR (CDCl$_3$) δ 1.04 (s, 3H, CH$_3$), 2.33 (d, 1H, cyclopropyl, J=7.2 Hz), 2.92 (d, 1H, cyclopropyl, J=7.2 Hz), 4.92 (d, 1H, J=1.5 Hz), 5.22 (d, 1H, J=1.5 Hz), 6.88–7.44 (m, 18H, aromatic).

Furthermore 0.20 g of pure benzhydryl 7α-bromo-2spiro[2', 2'-(4',4'-difluoro)diphenyl]cyclopropyl-3-methyl-3-cephem-4-carboxylate-1,1-dioxide was obtained as the minor isomer.

NMR (CDCl$_3$) δ 1.65 (s, 3H, CH$_3$), 2.33 (d, 1H, cyclopropyl, J=7.3 Hz), 2.78 (d, 1H, cyclopropyl, J=7.3 Hz), 4.8 (s, 2H, H-6+H-7), 6.82–7.54 (m, 18H, aromatic).

NOTE: Subsequent analysis has revealed that the major isomer is actually benzhydryl 7α-bromo-2-spiro[2',2'-(4',4'-difluoro) diphenyl]cyclopropyl-3- methyl-3-cephem-4-carboxylate 1,1-dioxide, and the minor isomer is actually benzhydryl 7α-bromo-2-spiro[3',3'-(4',4'-difluoro)diphenyl]cyclopropyl-3-methyl-3-cephem-4-carboxylate-1,1-dioxide.

SUPPLEMENTAL EXAMPLE 7 t-Butyl 7α-chloro-2-spiro(3',3'-diphenyl)cyclopropyl-3-acetoxymethyl-3-cephem-4-carboxylate-1,1-dioxide Dry dioxane was freed from peroxide by passage through a column of neutral activated alumina. To 100 ml of this solvent was added, in turn, with ice-cooling 10 ml of conc. sulfuric acid, 10.9 g of 7-ACA and 50 ml of liquid isobutylene. The mixture was sealed in a pressure bottle, stirred at 30° C. for 2 hours, poured into excess of ice-cold aqueous sodium bicarbonate solution. The solution was extracted with ethyl acetate. The combined ethyl acetate extract was washed with brine and dried over sodium sulfate. Evaporation of the filtrate under reduced pressure gave a light brown foam, 8.3 g (63%) of t-butyl-7β-amino-3-acetoxymethyl-3-cephem-4-carboxylate.

NMR (CDCl$_3$) δ 1.5 (s, 9H, 5-butyl), 1.8 (bs, 2H, NH$_2$), 2.1 (s, 3H, OCOCH$_3$), 3.45 (ABq, 2H, H-2, J=18 Hz), 4.7–5.2 (m, 4H, H-6+H-7+CH$_2$OCOCH$_3$).

Following substantially the same procedure as described in Example 1, Step A, 4.0 gm of t-butyl-7β-amino-3-acetoxymethyl-3-cephem-4-carboxylate was converted to t-butyl 7α-chloro-3-acetoxymethyl-3-cephem-4-carboxylate (3.1 g, 73%). NMR (CDCl$_3$) δ 1.55 (s, 9H, t-butyl), 2.1 (s, 3H, OCOCH$_3$), 3.5 (ABq, 2H, H-2, J=18 Hz), 4.6–5.1 (m, 4H, H-6+H-7+CH$_2$OCOCH$_3$).

Following substantially the same procedure as described in Example 1, Step C, 3.1 gm of t-butyl 7α-chloro-3-acetoxymethyl-3-cephem-4-carboxylate in 50 ml of methylene chloride was oxidized to give 1.0 gm (30%) of t-butyl 7α-chloro-3-acetoxymethyl-3-cephem-4-carboxylate-1,1-dioxide.

NMR (CDCl$_3$) δ 1.55 (s, 9H, t-butyl), 2.1 (s, 3H, OCOCH$_3$), 3.9 (ABq, 2H, H-2, J=18 Hz), 4.8 (bs, 1H), 4.95 (ABq, 2H, CH$_2$OCOCH$_3$, J=14 Hz), 5.3 (bs, 1H).

Furthermore, 0.9 g of the t-butyl 7α-chloro-3-acetoxymethyl-3-cephem-4-carboxylate-1,1-dioxide obtained above was converted as in Example 1, Step D to the corresponding 2-methylene derivative (0.43 g, 46%), m.p. 148° C.–149° C. followed by treatment with diphenyldiazomethane to afford t-butyl 7α-chloro-2-spiro(3',3'-diphenyl)cyclopropyl-3-acetoxymethyl-3-cephem-4-carboxylate-1,1-dioxide, m.p. 163° C.–165° C.

NMR (CDCl$_3$) δ 1.55 (s, 9H, t-butyl), 2.01 (s, 3H, OCOCH$_3$), 2.37 (d, 1H, cyclopropyl, J=7 Hz), 3.03 (d, 1H, cyclopropyl, J=7 Hz), 3.12 and 4.08 (dd, 2H, CH$_2$OCOCH$_3$, J=13 Hz), 5.01 (d, 1H, J=2 Hz), 5.26 (d, 1H, J=2 HZ), 7.22–7.48 (m, 10H, aromatic).

NOTE: Subsequent analysis has revealed that this product is actually t-butyl 7α-chloro-2-spiro(2',2'-(diphenyl)cyclopropyl-3-acetoxymethyl-3-cephem-4-carboxylate 1,1-dioxide.

Following the procedures described in (1) Example 5, Step A and (2) Example 6, Step A but starting with an appropriate hydrazone and treating the resulting diazo compound with benzhydryl 7α-bromo-2-methylene-3-methyl-3-cephem-4-carboxylate-1,1-dioxide the following cyclopropyl derivatives were prepared.

(1) Benzhydryl 7α-bromo-2-spiro(3'-ethoxycarbonyl)cyclopropyl-3-methyl-3-cephem-4-carboxylate-1,1-dioxide.

NMR (CDCl$_3$) δ 1.23 (t, 3H, COOCH$_2$CH$_3$), 1.80 (s, 3H, CH$_3$), 2.18 (d, 2H, cyclopropyl, J=8.5 Hz), 2.75 (t, 1H, CHCOOCH$_2$CH$_3$, J=8.5 Hz), 4.17 (q, 2H, COOCH$_2$CH$_3$), 5.08 (d, 1H, J=1.5 Hz), 5.26 (d, 1H, J=1.5 Hz), 6.98 (s, 1H, CHPh$_2$), 7.26–7.37 (m, 10H, aromatic).

NOTE: Subsequent analysis has revealed that this product is actually benzhydryl 7α-bromo-2-spiro(2'-ethoxycarbonyl)cyclopropyl- 3-methyl-3-cephem-4-carboxylate 1,1-dioxide.

(2) Benzhydryl 7α-bromo-2-spiro(2'-ethoxycarbonyl)cyclopropyl-3-methyl-3-cephem-4-carboxylate-1,1-dioxide.

NMR (CDCl$_3$) δ 1.26 (t, 3H, COOCH$_2$CH$_3$), 2.0–2.14 (m, 2H, cyclopropyl), 2.36 (s, 3H, CH$_3$), 2.78 (q, 1H, CHCOOCH$_2$CH$_3$), 4.06 (q, 2H, COOCH$_2$CH$_3$), 4.72 (d, 1H, J=1.5 Hz), 5.29 (d, 1H, J=1.5 Hz), 6.88 (s, 1H, CHPh$_2$), 7.25–7.47 (m, 10H, aromatic).

NOTE: Subsequent analysis has revealed that this product is actually benzhydryl 7α-bromo-2-spiro(3'-ethoxycarbonyl)cyclopropyl-3-methyl-3-cephem-4-carboxylate 1,1-dioxide.

(3) Benzhydryl 7α-bromo-2-spiro[3'-spiro(9-fluorenyl)]cyclopropyl-3-methyl-3-cephem-4-carboxylate-1,1-dioxide.

NMR (CDCl$_3$) δ 2.56 (s, 3H, CH$_3$), 2.73 (d, 1H, cyclopropyl, J=8 Hz), 3.13 (d, 1H, cyclopropyl, J=8 Hz), 3.38 (d, 1H, J=2 Hz), 4.37 (d, 1H, J=2 Hz), 6.7 (s, 1H, CHPh$_2$), 6.73–7.84 (m, 18H, aromatic).

(4) Benzhydryl 7α-bromo-2-spiro(3'-phenyl-3'- methyl)cyclopropyl-3-methyl-3-cephem-4-carboxylate-1,1-dioxide. NMR (CDCl$_3$) δ 0.92 (s, 3H, CH$_3$), 1.78 (s, 3H, CH$_3$), 2.23 (ABq, 2H, cyclopropyl, J=7 Hz), 5.03 (d, 1H, J=1.7 Hz), 5.34 (d, 1H, J=1.7 Hz), 6.9 (s, 1H, CHPh$_2$), 7.18–7.48 (m, 15H, aromatic).

NOTE: Subsequent analysis has revealed that this product is actually benzhydryl 7α-bromo-2-spiro(2'-phenyl-2'-methyl) cyclopropyl-3-methyl-3-cephem-4-carboxylate 1,1-dioxide.

(5) Benzhydryl 7α-bromo-2-spiro(2'-phenyl-2'-methyl)cyclopropyl-3-methyl-3-cephem-4-carboxylate-1,1-dioxide. NMR (CDCl$_3$) δ 1.58 (s, 3H, CH$_3$), 1.85 (s, 3H, CH$_3$), 2.13 (d, 1H, cyclopropyl, J=7 Hz), 2.25 (d, 1H, cyclopropyl, J=7 Hz), 4.86 (d, 1H, J=2 Hz), 5.24 (d, 1H, J=2 Hz), 6.81 (s, 1H, CHPh$_2$), 7.21–7.46 (m, 15H, aromatic).

NOTE Subsequent analysis has revealed that this product is actually benzhydryl 7α-bromo-2-spiro(3'-phenyl-3'-methyl) cyclopropyl-3-methyl-3-cephem-4-carboxylate 1,1-dioxide.

(6) Benzhydryl 7α-bromo-2-spiro(3'-phenyl)cyclopropyl-3-methyl-3-cephem-4-carboxylate-1,1-dioxide.

NMR (CDCl$_3$) δ 1.07 (s, 3H, CH$_3$), 2.09 (dd, 1H, cyclopropyl, J=6.8 Hz and 8.0 Hz), 2.39 (dd, 1H, cyclopropyl, J=6.8 Hz and 8.0 Hz), 3.29 (dd, 1H, cyclopropyl, J=8.0 Hz and 10.0 Hz), 5.16 (d, 1H, J=1.4 Hz), 5.45 (d, 1H, J=1.4 Hz), 6.90 (s, 1H, CHPh$_2$), 7.22–7.36 (m, 15H, aromatic).

NOTE: Subsequent analysis has revealed that this product is actually benzhydryl 7α-bromo-2-spiro(2'-phenyl)cyclopropyl-3-methyl-3-cephem-4-carboxylate 1,1-dioxide.

(7) Benzhydryl 7α-bromo-2-spiro(2'-phenyl)cyclopropyl-3-methyl-3-cephem-4-carboxylate-1,1-dioxide.

NMR (CDCl$_3$) δ 1.93–2.01 (m, overlapping α and ν, 4H, CH$_3$+cyclopropyl), 2.58 (dd, 1H, cyclopropyl, J=6.6 Hz and 8.9 Hz), 3.05 (t, 1H, cyclopropyl, J=9.0

Hz), 4.49 (d, 1H, J=1.4 Hz), 5.12 (d, 1H, J=1.4 Hz), 6.96 (s, 1H, CHPh₂), 7.26–7.49 (m, 15H, aromatic).

NOTE: Subsequent analysis has revealed that this product is actually benzhydryl 7α-bromo-2-spiro(3'-phenyl)cyclopropyl-3-methyl-3-cephem-4-carboxylate 1,1-dioxide.

The compounds of the present invention in which $R_5$ possesses an alpha-orientation at the 7-position of the cephem ring are preferred over their counterpart compounds wherein $R_5$ has a beta-orientation due to higher activity against human leukocyte elastase. Similarly, spirocyclopropyl derivatives which have a 2',2'-structure (i.e. $R_3$ and $R_4$ are located on the 2'-carbon atom of the spirocyclopropyl structure) are preferred over corresponding derivatives which have a 3',3'-spirocyclopropyl structure.

What is claimed is:

1. A 2-spirocyclopropyl cephalosporin sulfone compound of formula I:

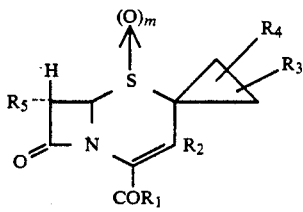

wherein $R_1$ is $NR_7R_8$;

$R_2$ is hydrogen, halogen, hydroxy, $C_{1-6}$ alkyl, $C_{1-6}$ alkoxy, $C_{2-6}$ alkenyl, $C_{2-6}$ alkynyl, $C_{3-8}$ cycloalkyl, or $CH_2 X$, wherein X is hydrogen, halogen, acetate, a triazoyl group, a quaternary ammonium group selected from the group consisting of pyridinium group, N-methyl pyrrolidinium group, and N-methyl piperidinium group, or $CH_2 YR_9$, wherein Y is oxygen, sulfur or nitrogen, and when Y is oxygen, $R_9$ is hydrogen or a $C_{1-6}$ alkyl group, when Y is sulfur, $R_9$ is a phenyl group or a 5 to 6 membered heterocyclic group containing 1 to 4 nitrogen atoms, with or without sulfur or oxygen, wherein the heterocyclic ring can be further substituted with a methyl group, a hydroxy group, a carboxy group, or $CH_2COOH$ group, and when Y is nitrogen, $R_9$ is H, $C_{1-6}$ alkyl, or phenyl;

$R_3$ and $R_4$, which are the same or different, are hydrogen, $C_{1-6}$ alkyl group, halo $C_{1-6}$ alkyl, $C_{6-10}$ aryl, halo $C_{6-10}$ aryl, $C_{3-8}$ cycloalkyl, hydroxy $C_{1-6}$ alkyl, $C_{1-6}$ alkanoyloxy $C_{1-6}$ alkyl, a $-CH_2COOH$ group, a $-COOH$ group, a $COOC_{1-6}$ alkyl group, a $-CH_2COOC_{1-6}$ alkyl group, or a 5 to 6 membered heterocyclic group containing at least one heteroatom selected from the group consisting of O, S, and N;

$R_5$ is hydrogen, halogen, methoxy, ethoxy, methylsulfonamido, trifluoromethyl sulfonamido, methanesulfonyloxy, or trifluoromethane sulfonyloxy;

$R_7$ is hydrogen, $C_{1-6}$ alkyl, $C_{2-6}$ alkenyl, $C_{2-6}$ alkynyl, $C_{1-6}$ alkanoyl $C_{1-6}$ alkyl, $C_{1-6}$ alkanoyloxy $C_{1-6}$ alkyl, $C_{1-6}$ alkoxy $C_{1-6}$ alkyl, $C_{3-6}$ cycloalkyl, halogenated $C_{1-6}$ alkyl, $-CH_2COOH$, a phenyl, $CH_2$(phenyl), or $-CH$(phenyl)₂, wherein the phenyl group may be substituted with at least one of $C_{1-6}$ alkyl, $C_{1-6}$ alkoxy, $C_{1-6}$ alkylthio, $C_{1-6}$ alkanoyl, $C_{1-6}$ alkanoyloxy, carboxy, nitro, $C_{1-6}$ alkylamino, amino, halogen, trifluoromethyl, $C_{1-6}$ alkylsulfinyl and $C_{1-6}$ alkylsulfonyl;

$R_8$ is hydrogen, $C_{1-6}$ alkyl, $C_{2-6}$ alkenyl, $C_{2-6}$ alkynyl, $C_{1-6}$ alkanoyl $C_{1-6}$ alkyl, $C_{1-6}$ alkanoyloxy $C_{1-6}$ alkyl, $C_{1-6}$ alkoxy $C_{1-6}$ alkyl, $C_{3-6}$ cycloalkyl, halogenated $C_{1-6}$ alkyl, $-CH_2COOH$, phenyl, $-CH_2$(phenyl), or $-CH$(phenyl)₂, wherein the phenyl may be substituted with at least one of $C_{1-6}$ alkyl, $C_{1-6}$ alkoxy, $C_{1-6}$ alkylthio, $C_{1-6}$ alkanoyl, $C_{1-6}$ alkanoyloxy, nitro, $C_{1-6}$ alkylamino, amino, halogen, trifluoromethyl, $C_{1-6}$ alkylsulfinyl and $C_{1-6}$ alkylsulfonyl, or $R_7$ and $R_8$ may form part of a heterocyclic ring containing 3–7 carbon atoms with the N to which they are bound, wherein the heterocyclic ring may contain one or more additional heteroatoms selected from the group of consisting of S, O, and N, and wherein the ring is unsubstituted or substituted at a carbon atom or at a nitrogen atom with one or more members of the group consisting of $C_{1-6}$ alkyl, $COOC_{1-6}$ alkyl, $-COOH$, $CH_2COOC_{1-6}$ alkyl, and $CH_2COOH$;

m is 1 or 2;

or a pharmaceutically or veterinarily acceptable salt or ester thereof.

2. A compound according to claim 1, wherein $R_1$ is

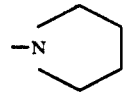

, $R_2$ is methyl, $R_3$ and $R_4$ are 2'-phenyl, $R_5$ is $OCH_3$ and m=2.

3. A compound according to claim 1, wherein $R_1$ is

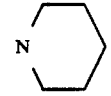

, $R_2$ is methyl, $R_3$ and $R_4$ are R'-phenyl, $R_5$ is $OCH_3$ and m=2.

4. A pharmaceutical composition for controlling inflammatory or degenerative conditions in a mammal comprising an effective amount of a compound of claim 1 in admixture with a pharmaceutically acceptable carrier.

5. A method of controlling inflammatory or degenerative conditions in a mammal, which comprises administering to a mammal in need of such treatment an effective amount of a compound according to claim 1.

6. A method of treating an elastase-mediated pathological condition in humans which comprises administering a physiologically acceptable form of the compound of claim 1.

7. The compound of claim 1, wherein $R_3$ and $R_4$ are both bonded to the 2'-carbon atom of the spirocyclopropyl structure.

8. The compound of claim 1, wherein $R_5$ possesses an alpha-orientation.

9. A pharmaceutical composition for controlling inflammatory or degenerative conditions in a mammal comprising an effective amount of a compound of claim 2 in admixture with a pharmaceutically acceptable carrier.

10. A method of controlling inflammatory or degenerative conditions in a mammal, which comprises administering to a mammal in need of such treatment an effective amount of a compound according to claim 2, 11. A method of treating an elastase-mediated pathological condition in humans which comprises administering a physiologically acceptable form of the compound of claim 2.

12. A pharmaceutical composition for controlling inflammatory or degenerative conditions in a mammal comprising an effective amount of a compound of claim 3 in admixture with a pharmaceutically acceptable carrier.

13. A method of controlling inflammatory or degenerative conditions in a mammal, which comprises administering to a mammal in need of such treatment an effective amount of a compound according to claim 3.

14. A method of treating an elastase-mediated pathological condition in humans which comprises administering a physiologically acceptable form of the compound of claim 3.

15. A compound according to claim 1 which is selected from the group consisting of: 7α-bromo-2-spiro (2',2'-diphenyl)cyclopropyl-3-methyl-3-cephem-4-pyrrolidine carboxamide-1,1-dioxide; 7α-methoxy-2-spiro (2',2'-diphenyl)cyclopropyl-3-methyl-3-cephem4-pyrrolidine carboxamide-1,1-dioxide; and 7α-methoxy-2-spiro (2',2'-diphenyl)cyclopropyl-3-methyl-3-cephem-4-piperidine carboxamide-1,1-dioxide.

16. A compound according to claim 1 which is selected from the group consisting of:

7α-methoxy-2-spiro (2',2'-diphenyl)cyclopropyl-3-[(1,2,3-triazolyl) methyl]-3-cephem-4-piperidine carboxamide-1,1-dioxide;

7α-methoxy-2-spiro (2',2'-diphenyl)cyclopropyl-3-methyl-3-cephem-4-[2-(S)-t-butoxycarbonyl pyrrolidine carboxamide]-1,1-dioxide;

7α-methoxy-2-spiro (2',2'-diphenyl)cyclopropyl-3-methyl-3-cephem-4-(N-methyl piperazine carboxamide)-1,1-dioxide;

7α-methoxy-2-spiro (2',2'-diphenyl)cyclopropyl-3-methyl-3-cephem-4-[4-t-butoxycarbonyl piperidine carboxamide]-1,1-dioxide;

7α-methoxy-2-spiro (2',2'-diphenyl)cyclopropyl-3-methyl-3-cephem-4-[4-carboxy piperidine carboxamide]-1,1-dioxide;

7α-methoxy-2-spiro (2',2'-diphenyl)cyclopropyl-3-methyl-3-cephem-4-[2-{N-t-butylpropionate-2-yl) carboxamido{] pyrrolidine carboxamide-1,1-dioxide;

7α-methoxy-2-spiro (2',2'-diphenyl)cyclopropyl-3-methyl-3-cephem-4-[2-{N-(α-methylacetic acid) carboxamido}]pyrrolidine carboxamide 1,1-dioxide;

7α-methoxy-2-spiro (2',2'-diphenyl)cyclopropyl-3-methyl-3-cephem-4-{N-(1-t-butoxycarbonyl-3-methyl-butane-1-yl)} carboxamide-1,1-dioxide;

7α-methoxy-2-spiro (2',2'-diphenyl)cyclopropyl-3-methyl-3-cephem-4-{N-(1-carboxy-3-methyl-butane-1-yl)} carboxamido-1,1-dioxide;

7α-methoxy-2-spiro (2',2'-diphenyl)cyclopropyl-3-methyl-3-cephem-4-[2-(S) carboxy pyrrolidine carboxamide]-1,1-dioxide;

7α-methoxy-2-spiro (2',2'-diphenyl)cyclopropyl-3-methyl-3-cephem-4-(4-tert-butoxycarbonyl) piperazine carboxamide 1,1-dioxide;

7α-methoxy-2-spiro (2',2'-diphenyl)cyclopropyl-3-methyl-3-cephem-4-piperazine carboxamide-1,1-dioxide;

7α-methoxy-2-spiro (2',2'-diphenyl)cyclopropyl-3-methyl-3-cephem-4-[4-tert-butoxy carbonyl methyl]-piperazine carboxamide-1,1-dioxide; and 7α-methoxy-2-spiro (2',2'-diphenyl)cyclopropyl-3-methyl-3-cephem-4-[4-N-acetic acid] piperazine carboxamide-1,1-dioxide.

* * * * *